United States Patent
Blum et al.

(10) Patent No.: US 11,344,634 B2
(45) Date of Patent: May 31, 2022

(54) ACTIVITY BASED PROBE AND USES THEREOF FOR IMAGING

(71) Applicant: Yissum Research Development Company of the Hebrew University of Jerusalem Ltd., Jerusalem (IL)

(72) Inventors: Galia Blum, Maccabim (IL); Darya Tsivrkun, Rishon Letzion (IL); Hanmant Gaikwad, Pandharpur MH (IN)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 620 days.

(21) Appl. No.: 16/077,879

(22) PCT Filed: Feb. 16, 2017

(86) PCT No.: PCT/IL2017/050207
§ 371 (c)(1),
(2) Date: Aug. 14, 2018

(87) PCT Pub. No.: WO2017/141251
PCT Pub. Date: Aug. 24, 2017

(65) Prior Publication Data
US 2019/0054193 A1 Feb. 21, 2019

Related U.S. Application Data

(60) Provisional application No. 62/296,655, filed on Feb. 18, 2016.

(51) Int. Cl.
*A61K 49/04* (2006.01)
*A61B 6/03* (2006.01)
*A61B 6/00* (2006.01)

(52) U.S. Cl.
CPC .......... *A61K 49/0428* (2013.01); *A61B 6/032* (2013.01); *A61B 6/508* (2013.01); *A61K 49/0438* (2013.01); *A61K 49/0442* (2013.01); *A61B 6/481* (2013.01)

(58) Field of Classification Search
CPC .... A61K 49/00; A61K 49/04; A61K 49/0428; A61K 49/0438; A61K 49/0442; A61K 2123/00; A61K 2121/00; A61B 6/032; A61B 6/508; A61B 6/481

USPC ...... 424/1.11, 1.49, 1.65, 1.69, 9.1, 9.2, 9.3, 424/9.4, 9.5, 9.6; 977/773
See application file for complete search history.

(56) References Cited

U.S. PATENT DOCUMENTS

| | | | |
|---|---|---|---|
| 8,968,700 B2 | 3/2015 | Bogyo et al. | |
| 10,919,089 B2 * | 2/2021 | Kircher | A61K 9/5115 |
| 2009/0203877 A1 | 8/2009 | Heckl et al. | |
| 2009/0252677 A1 | 10/2009 | Bogyo et al. | |

FOREIGN PATENT DOCUMENTS

WO  2012/175223 A1  12/2012

OTHER PUBLICATIONS

Chen et al., "Therapeutic nanomedicine based on dual-intelligent functionalized gold nanoparticles for cancer imaging and therapy in vivo", Biomaterials, vol. 34, No. 34, pp. 8798-8807, (2013).
Edem et al., "Synthesis and Evaluation of Radioiodinated Acyloxymethyl Ketones as Activity-Based Probes for Cathepsin B", J. Med. Chem., vol. 57, No. 22, pp. 9564-9577, (2014).
Edem, "Molecular Imaging Agents for Cathepsin B: Design, Synthesis, and Evaluation of Molecular Imaging Probes for Cathepsin B", Ph.D. Thesis—Patricia Edem; McMaster University—Chemistry & Chemical Biology, Dec. 1, 2015.
Fu et al., "Dendritic Iodinated Contrast Agents with PEG-Cores for CT Imaging: Synthesis and Preliminary Characterization", Bioconjugate Chem., vol. 17, No. 4, pp. 1043-1056, (2006).
Razgulin et al., "Strategies for in vivo imaging of enzyme activity: an overview and recent advances", Chem. Soc. Rev., vol. 40, No. 7, pp. 4186-4216, (2011).
Sun et al., "Tumor-Targeting Gold Particles for Dual Computed Tomography/Optical Cancer Imaging", Angew. Chem. Int. Ed., vol. 50, No. 40, pp. 9348-9351, (2011).
Yordavon et al., "Novel Iodinated Dendritic Nanoparticles for Computed Tomography (CT) Imaging", Nano Letters, vol. 2, No. 6, pp. 595-599, (2002).

* cited by examiner

*Primary Examiner* — D. L. Jones
(74) *Attorney, Agent, or Firm* — Vorys, Sater, Seymour and Pease LLP; Anthony Venturing

(57) ABSTRACT

Provided is a compound including at least one carrier moiety associated with a plurality of CT imaging moieties, and with at least one enzyme interacting moiety as well as uses thereof in diagnosis.

8 Claims, 22 Drawing Sheets

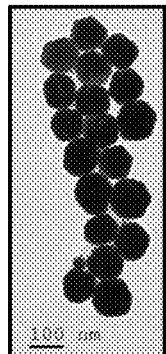
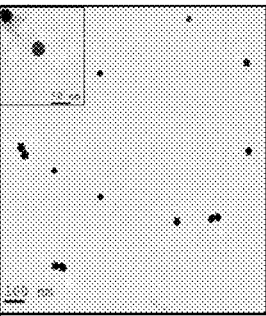
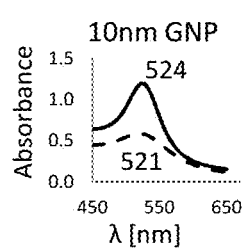
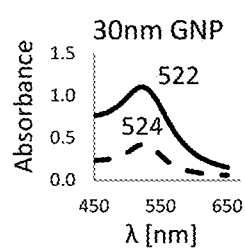
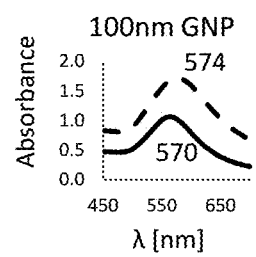
Figure 1D            Figure 1E            Figure 1F ~COOH : ~OMe
5kDa : 5kDa (i)
10%

~COOH : ~OMe
5kDa : 5kDa (ii)
50%

~COOH
5kDa (iii)
or
SH-PEG-GB111
100%

~COOH : ~OMe
3kDa : 5kDa (iv)
10%

~COOH : ~OMe
3kDa : 5kDa (v)
50%

~COOH
3kDa (vi)
100% control - NT (vii)

- GB111
- Gold nanoparticle
  - 10 nm
  - 30 nm
  - 100 nm

Fig. 5A
Fig. 5B
Fig. 5C
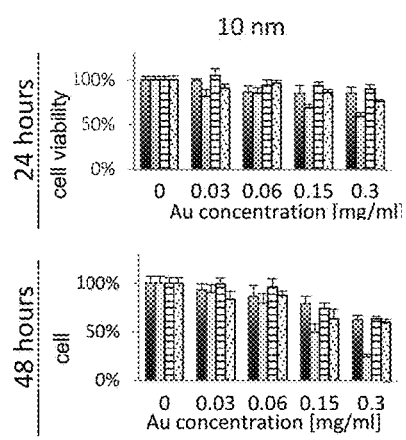
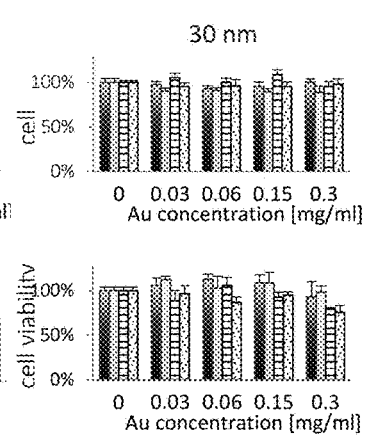
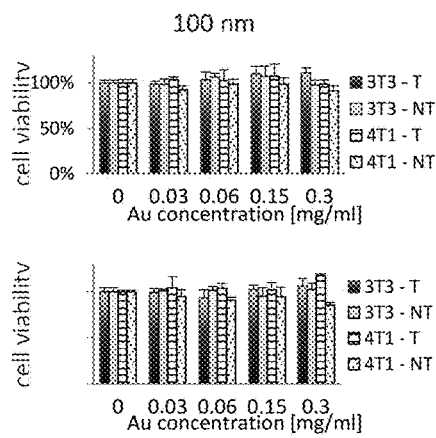
Fig. 5D
Fig. 5E
Fig. 5F
Fig. 6A
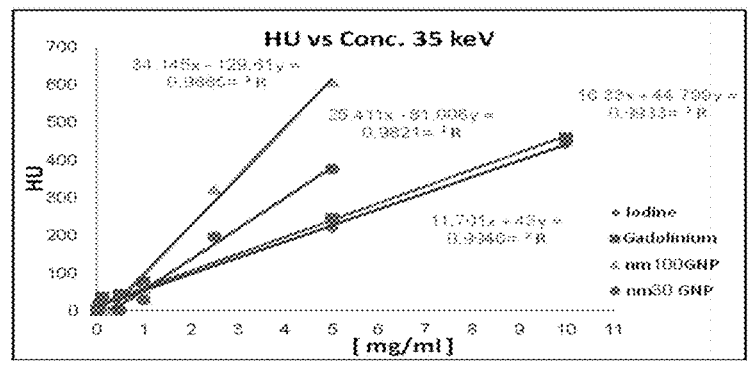

Fig. 7G
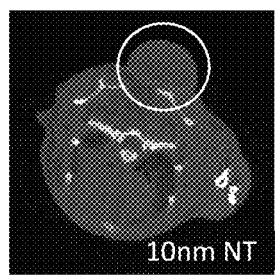
10nm NT
Fig. 7H
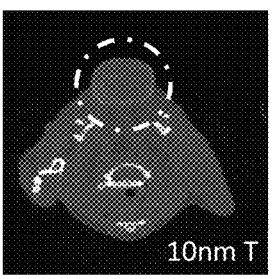
10nm T
Fig. 7I
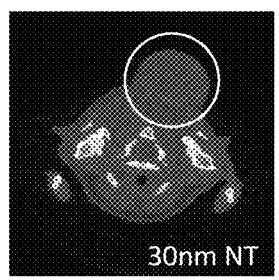
30nm NT
Fig. 7J
30nm T
Fig. 7K
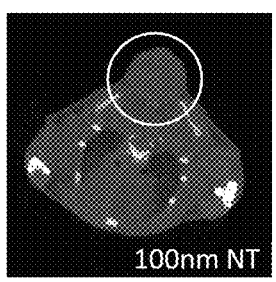
100nm NT
Fig. 7L
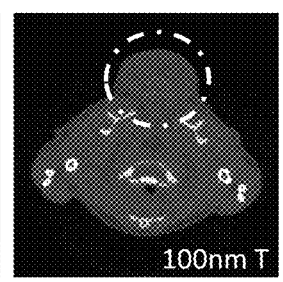
100nm T Fig. 8A
10 nm
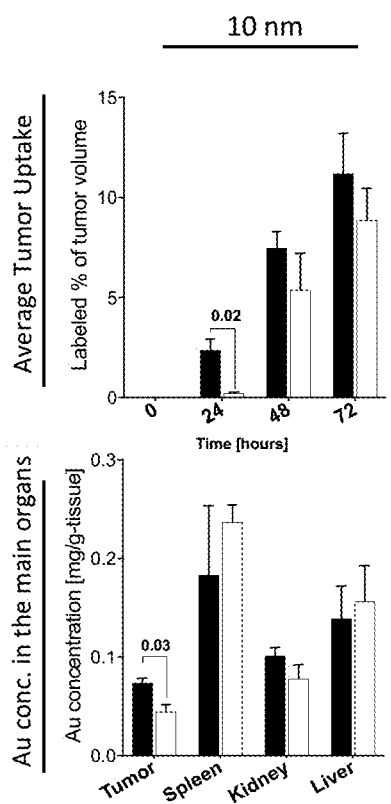
Fig. 8B
30 nm
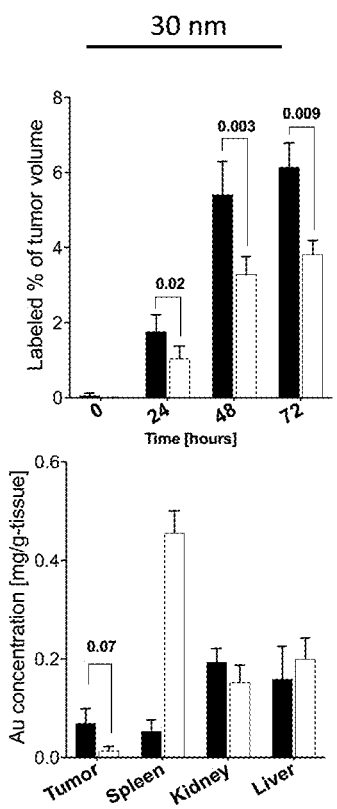
Fig. 8C
100 nm
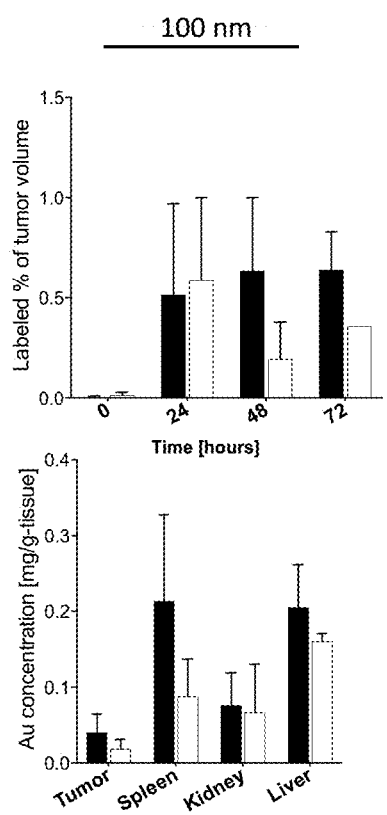
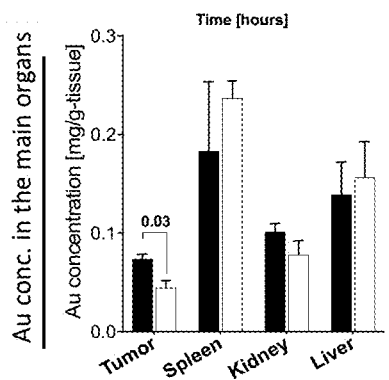
Fig. 8D
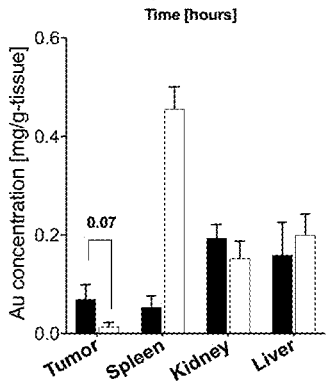
Fig. 8E
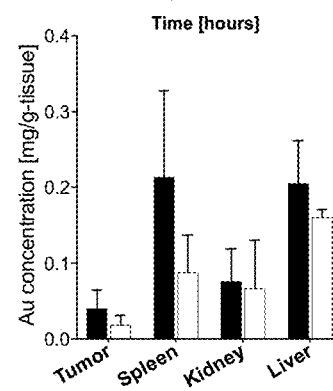
Fig. 8F Fig. 10A 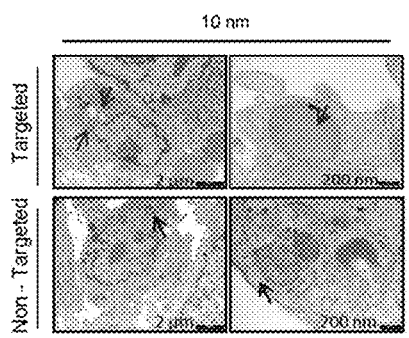 Fig. 10B 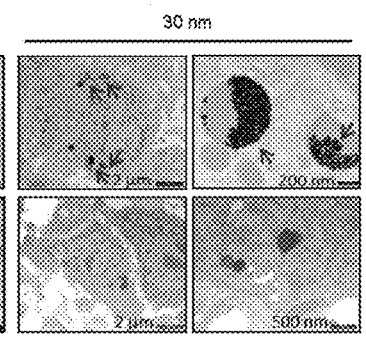 Fig. 10C 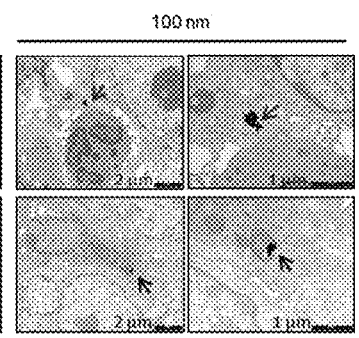
Fig. 10D  Fig. 10E  Fig. 10F
Fig. 11A
Fig. 11B Fig. 11D
Fig. 11E Fig. 14A 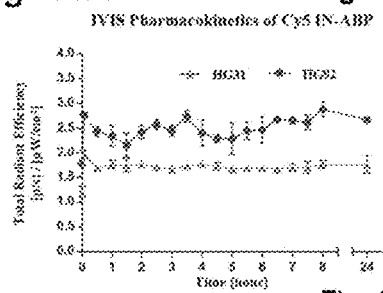 Fig. 14B 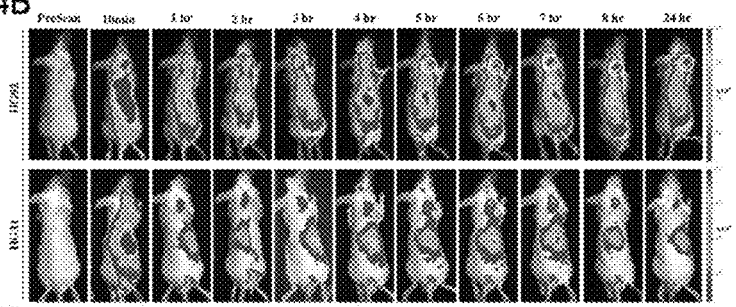
Fig. 14C 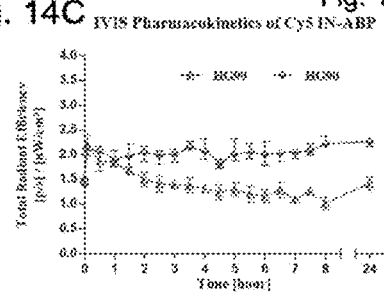 Fig. 14D 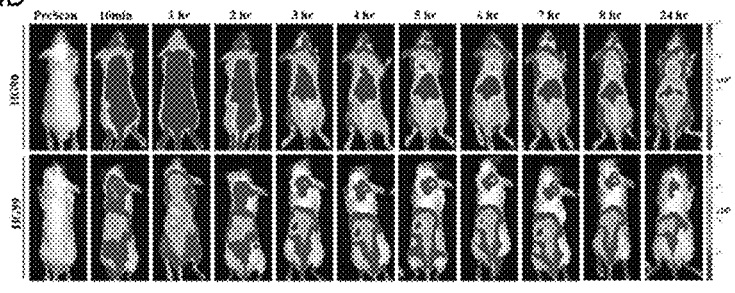
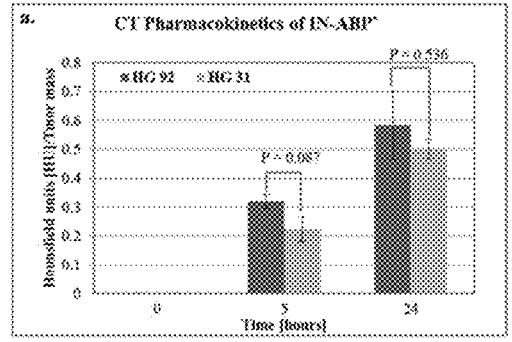 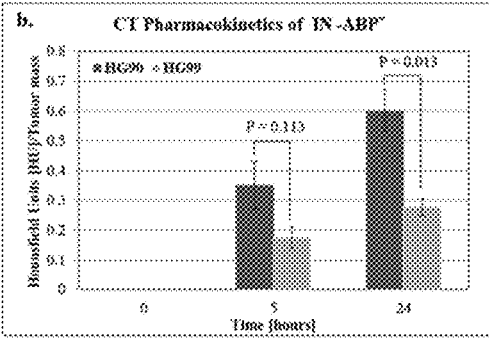
Fig. 15A     Fig. 15B

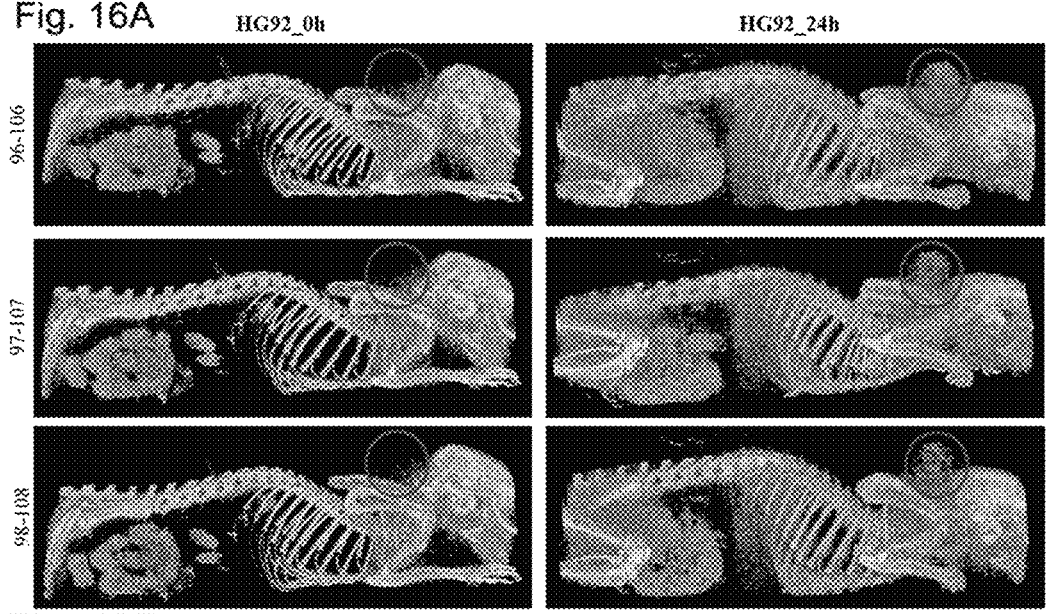
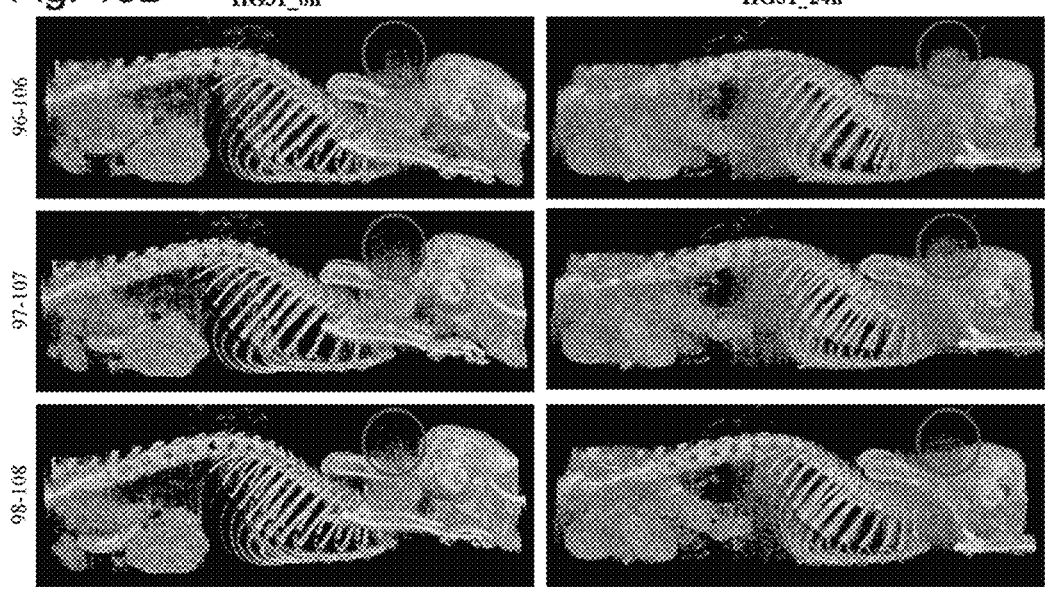

~COOH (vi)
3kDa
100%

● GB111

ACTIVITY BASED PROBE AND USES THEREOF FOR IMAGING

The work leading to this invention has received funding from the European Research Council under the European Union's Seventh Framework Programme (FP7/2007-2013)/ERC grant agreement no [337238].

TECHNOLOGICAL FIELD

The present disclosure relates to imaging agents and methods of using same in X-ray computed tomography (CT) imaging.

BACKGROUND

Activity based probes are small molecules that modify a defined set of enzyme targets based on their ability to form specific bonds with key catalytic residues. Since this labeling reaction is mechanism-based and requires enzyme activity, extent of probe modification serves as an indirect readout of activity levels within a given sample. Probes can be designed to target a number of different classes of enzymes through optimization of both reactive functional groups and the scaffolds used to carry the reporter tag.

A number of classes of such probes have been developed and used to dissect the function of various enzyme families. The most well-established and heavily used probes are those that target proteolytic enzymes. These probes that target serine and cysteine proteases, such as cathepsin, have been applied to studies of protease function in processes such as parasite invasion, prohormone processing, transcriptional regulation, cataract formation, natural killer cell function and cancer progression.

WO 2012/175223 [1] discloses cathepsin-binding compounds, bound to a carrier and comprising a diagnostic moiety, for use in the diagnosis of inflammatory diseases, and/or for use in the diagnosis of neoplastic diseases.

BACKGROUND ART

[1] WO 2012/175223

GENERAL DESCRIPTION

The present disclosure is based on the design and development of compounds that comprise an X-ray computed tomography (CT)-imaging moiety that specifically and selectively recognizes and binds a target enzyme, for example a protease.

In order to overcome the intrinsic low sensitivity associated with CT, the inventors have developed novel chemical routes for the synthesis of such novel compounds that involve solid and solution phase chemistries, that provides the means for increasing the number of imaging moieties on a single compound, and that achieve an informative and accurate CT signal. Since compounds of the invention are intended for in vivo detection, the inventors have carefully tuned the size and number of imaging moieties to eventually enable, on one hand, penetration of the compounds into cells and, on the other hand, to enable detection of the CT signal.

Compounds of the invention selectively recognize a target enzyme, present either within a cell or secreted from cells, for example a protease of interest, and undergo interaction with the target enzyme, e.g., by bond cleavage and/or chemical association or conjugation thereto (e.g., by covalent bonding). By conjugation or otherwise association to the enzyme at locations of high enzyme expression, a sufficient CT signal (above normal tissue background) from multiple imaging moieties may be detected, enabling accurate localization of the target enzyme. The enzyme localities are typically indicative of a condition associated with increased expression of the enzyme, e.g., a protease such as cathepsin. As demonstrated herein, such accumulation of compounds of the invention in such locations results in an amplified imaging signal, which, when detected, provides an indication of or may hint to the presence of a pathology.

Without wishing to be bound by theory, it is suggested that compounds of the invention bind to an enzyme of interest (for example a protease, such as cathepsin) in a 1:1 ratio and since the activity and localization of these enzymes is increased (overexpressed) in certain pathologies, detection of such pathologies is possible.

Thus, compounds of the invention may be described as "activity based probes (ABP)", engineered to target and associate, conjugate or bind to a target enzyme, and thereby produce a signal. The ABP compounds are typically engineered to covalently modify enzyme targets in an activity-dependent manner. As shown hereinbelow, ABP compounds may be cell permeable materials that specifically and selectively recognize and settle at sites with increased active enzyme expression, such as cathepsins, and may thus assist in diagnosis of pathologies associated with increased enzyme expression in tissues.

The ABP compounds of the invention differ from substrate-based probes primarily in their mechanism of action. Rather than acting as substrates that are processed by the protease, ABPs act as direct covalent inhibitors of the protease. As such, the ABPs, upon interaction with the protease, become covalently bound to it. Such a covalent binding permits dynamic studies of enzyme activation and localization. Covalent binding maintains the ABP with its imaging moiety in place, for a longer duration and permits its accumulation in site over time.

Thus, in accordance with a first aspect, the present disclosure provides a compound (ABP) comprising at least one carrier moiety associated with a plurality of CT imaging moieties, and with at least one enzyme interacting moiety. Compounds of the invention may be characterized by (i) at least one carrier moiety that is selected from a macromolecule, a polymer, an oligomer, a dendrimer, a nanoparticle, a liposome, a lipoplex, a polymersome, a micell, a mesoporous silica particle and a nanotube and (ii) a plurality of CT imaging moieties selected from iodine-based moieties, lanthanide-based contrast agents and gold-based moieties.

The invention further provides an activity based probe comprising at least one CT imaging moiety and at least one enzyme interacting moiety, said moieties being each covalently associated with a carrier moiety.

The invention further provides an activity based probe selected to undergo interaction with at least one enzyme, the activity based probe having at least one enzyme recognition moiety selected to undergo covalent interaction with a target enzyme and at least one CT imaging moiety that enables detection of the activity based probe by CT.

The carrier moiety is used in accordance with the present invention to associate the enzyme interacting moiety and multiple CT imaging moieties, and optionally other diagnostically active or non-active moieties, around a common center or core. Such an association is required in order to increase sensitivity and allow detection of a target enzyme. Thus, the carrier moiety is selected based on its ability to bind the various moieties and, at the same time, in case the enzyme is localized within the cells allow cell penetration.

The carrier moieties may be any such material capable of multi-site (at least two) chemical association.

Non-limiting examples of carrier moieties include a macromolecule, a polymer, an oligomer, a dendrimer, a nanoparticle, a nanotube, a liposome, a lipoplex, a polymersome, a micell, a mesoporous silica particle and others.

In some embodiments, the carrier moiety is a macromolecule, such as a polyamine. In some embodiments, the carrier moiety comprises at least one macromolecular polyamine, being in some embodiments, in dendrimer form.

In some embodiments, the carrier moiety is a dendrimer, that is optionally amine-based.

As known in the art, dendrimers are repetitively branched molecules having a core with multiple branching generations extending therefrom. The dendrimers may be symmetric or non-symmetric around the core and often adopt a spherical three-dimensional morphology. Dendrimers utilized in accordance with the invention, may be of any generation (G) and may optionally have a skeleton that is amine based. In some embodiments, the dendrimers are selected amongst a first generation (G-1), a second generation (G-2), a third generation (G-3), a fourth generation (G-4), a fifth generation (G-5) or higher generation dendrimers.

In some embodiments, the amine skeleton is a polyamine. In some embodiments, the carrier moiety is a dendritic polyamine. In some embodiments, the polyamine is poly (amidoamine) (PAMAM).

In some embodiments, the carrier moiety carrying the enzyme interacting moiety and the multiple CT imaging moieties and optionally other diagnostically active or non-active moieties is PAMAM, selected in a dendritic form.

As known in the art, the PAMAM core is a diamine (commonly ethylenediamine), which is reacted with methyl acrylate and then another ethylenediamine to make PAMAM of generation-0, designated G-0. Successive reactions yield higher generations.

In some embodiments, the carrier moiety used in accordance with the invention is a first generation PAMAM (G-1), a second generation PAMAM (G-2), a third generation PAMAM (G-3), a fourth generation PAMAM (0-4) or a fifth generation PAMAM (G-5).

In some other embodiments, the carrier moiety used in accordance with the invention is a first generation PAMAM (G-1) or a third generation PAMAM (G-3). In some other embodiments, the carrier moiety is a first generation PAMAM (G-1). In some other embodiments, the carrier moiety is a third generation PAMAM (G-3).

In some embodiments, the carrier moiety comprises at least one oligomer (having between 2 and 10 repeating units) or polymer (having 11 or more repeating units). In some embodiments, the oligomer or polymer is an oligopeptide or a poly amino acid sequence.

In some embodiments, the carrier moiety is at least one oligo-ether or poly-ether. In some embodiments, the carrier moiety is of the general Formula (CM):

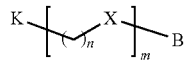

wherein
K is a point of connectivity to a CT imaging moiety;
B is a point of connectivity to an enzyme interacting moiety;
X is a heteroatom;
n is an integer from 1 to 20; and
m is an integer from 1 to 150.

In some embodiments, m is between 10 and 20, 10 and 30, 10 and 40, 10 and 50, 10 and 60, 10 and 70, 10 and 80, 10 and 90, 10 and 100, 10 and 110, 10 and 120, 10 and 130, 10 and 140, 10 and 150, 50 and 60, 50 and 70, 50 and 80, 50 and 90, 50 and 100, 50 and 110, 50 and 120, 50 and 130, 50 and 140, 50 and 150, 100 and 150, 100 and 140, 100 and 130, 100 and 120 or 100 and 110.

In some embodiments, m is between 60 and 120, 60 and 150, 50 and 70, 100 and 120 or 110 and 115.

In some embodiments, m is between 65 and 70.

In some embodiments, K being a point of connectivity to a CT imaging moiety, may be selected from —O—, —NH—, —S—. In some other embodiments, K is —S—.

In some embodiments, B being a point of connectivity to an enzyme interacting moiety, may be selected from —C(O)O—, —C(O)—, —$C_1$-$C_{10}$alkylene-C(O)O, —$C_1$-$C_{10}$alkylene-C(O)—, —C(O)—$C_1$-$C_{10}$alkylene-C(O)—, —C(O)—$C_1$-$C_{10}$alkylene-C(O)O—.

In some embodiments, the —$C_1$-$C_{10}$alkylene-used in any one of the variable groups herein is —$C_2$-alkylene, —$C_3$-alkylene, —$C_4$-alkylene, —$C_5$-alkylene, —$C_6$-alkylene, —$C_7$-alkylene, —$C_8$-alkylene, —$C_9$-alkylene or —$C_{10}$-alkylene.

In some embodiments, B is selected from —$C_1$-$C_5$alkylene-C(O)O—; —$C_1$-$C_5$alkylene-C(O)—, —C(O)—$C_1$-$C_5$alkylene-C(O)— and —C(O)—$C_1$-$C_5$alkylene-C(O)O—.

In some embodiments, B is selected from —C(O)O—, —C(O)—, -ethylene-C(O), -ethylene-C(O)—, —C(O)-ethylene-C(O)— and —C(O)-ethylene-C(O)O—.

In some embodiments, B is -ethylene-C(O)O— or -ethylene-C(O)—.

In some embodiments, X is selected from —NH—, O and S. In some other embodiments, X is an oxygen.

In some embodiments, K is —S—, B is -ethylene-C(O)— and X is an oxygen.

In some embodiments, K is a point of connectivity to the an enzyme interacting moiety.

In some embodiments, B is a point of connectivity to the an enzyme interacting moiety.

In some embodiments, K is a point of connectivity to the CT imaging moiety.

In some embodiments, B is a point of connectivity to CT imaging moiety.

In some embodiments, X is oxygen and n=2.

In some embodiments, each of n and m is an integer, such that n is 2 and m is between 2 and 150.

In some embodiments, the point of connectivity to the a CT imaging moiety, being either K or B is selected from —O—, —NH— and —S—. In some embodiments, the point of connectivity to the a CT imaging moiety, being either K or B, is —S—.

In some embodiments, the point of connectivity to the an enzyme interacting moiety, being either K or B is selected from —C(O)O—, —C(O)—, —$C_1$-$C_{10}$alkylene-C(O)O—, —$C_1$-$C_{10}$alkylene-C(O)—, —C(O)—$C_1$-$C_{10}$alkylene-C(O)— and —C(O)—$C_1$-$C_{10}$alkylene-C(O)O.

In some embodiments, —$C_1$-$C_{10}$alkylene- is —$C_2$-alkylene, —$C_3$-alkylene, —$C_4$-alkylene, —$C_5$-alkylene, —$C_6$-alkylene, —$C_7$-alkylene, —$C_8$-alkylene, —$C_9$-alkylene or —$C_{10}$-alkylene. In some embodiments, the point of connectivity to the an enzyme interacting moiety, being either K or B is selected from —$C_1$-$C_5$alkylene-C(O)O—, —$C_1$-$C_5$alkylene-C(O)—, —C(O)—$C_1$-$C_5$alkylene-C(O)— and —C(O)—$C_1$-$C_5$alkylene-C(O)O—. In some embodiments, the point of connectivity to the an enzyme interacting moiety, being either K or B, is selected from —C(O)O—, —C(O)—, -ethylene-C(O)O—, -ethylene-C(O)—, —C(O)-ethylene-C(O)— and —C(O)-ethylene-C(O)O—. In some embodiments, the point of connectivity to the an enzyme interacting moiety, being either K or B, is -ethylene-C(O)O— or -ethylene-C(O)—.

In some other embodiments, each of K and B, independently of the other, are exemplary points of connectivity to an enzyme interacting moiety and a CT imaging moieties, and may be selected from —O—, —O—CH$_3$—, —NH—, —S—, —SO$_2$—, —SO$_2$NH—, —C(O)NH, —NH—C(O)CH$_3$ and —C(O)O—;

X is a heteroatom selected from —NH—, O and S;

each of n and m, independently of the other is an integer, such that n is selected from 1 to 20 and m is selected from 2 to 150.

In some embodiments, the carrier moiety is an oligomer or a polymer of ethylene oxide, being of different lengths and molecular weights. In some embodiments, the oligomer or polymer of ethylene oxide is selected to have a molecular weight of between 800 Da and about 10 kDa. In some embodiments, the oligomer or polymer of ethylene oxide has a molecular weight of between 1 kDa and about 8 kDa. In some embodiments, the oligomer or polymer of ethylene oxide has a molecular weight of between 3 kDa and about 5 kDa. In some embodiments, the oligomer or polymer of ethylene oxide has a molecular weight of 3 kDa. In some embodiments, the oligomer or polymer of ethylene oxide has a molecular mass of 5 kDa. In some embodiments, the oligomer or polymer of ethylene oxide is a mixture of such oligomers and/or polymers of molecular masses between 3 kDa and 5 kDa, or a mixture of such oligomers and/or polymers having a molecular weight of 3 kDa and of such oligomers and/or polymers having a molecular weight of 5 kDa.

The oligomer or polymer of ethylene oxide may be a modified ethylene oxide. In some embodiments, the oligomer or polymer of ethylene oxide is a thiol-polyethyleneglycol. In some embodiments, the oligomer or polymer of ethylene oxide is a thiol-polyethylene-acid. In some further embodiments, the oligomer or polymer of ethylene oxide is a thiol-polyethylene-alkyl, having a methyl end group (—O-Me).

Each of the plurality of CT Imaging moieties is or comprises a CT contrast agent selected to provide visualization of a tissue of interest by X-ray CT, to thereby enable evaluation of tissue/organ function or performance. Non-limiting examples of CT contrast imaging agents include iodine-based moieties, lanthanide-based contrast agents, gold-based moieties and heavy metal-based contrast agents (tantalum and bismuth nanoparticles).

In some embodiments, the CT imaging moiety is an iodine-based moiety selected from iodinated moieties which may be ionic or non-ionic, having molecular weights of between 0.5 kDa and 30 kDa. In some further embodiments, an iodine-based moiety has molecular weights of between 1 kDa and 10 kDa.

In some embodiments, the iodine-based moiety is an iodine-substituted aromatic moiety, comprising one or more aryl rings, each being optionally substituted with one or more iodine atoms.

In some embodiments, the iodine-based moiety is an iodine-substituted aliphatic moiety, being optionally a carbocyclic moiety, substituted by one or more iodine atoms.

In some embodiments, the iodine-based moieties are selected amongst such commercially available materials, e.g., iohexol (Omnipaque™, GE Healthcare); iopromide (Ultravist™, Bayer Healthcare); iodixanol (Visipaque™, GE Healthcare); ioxaglate (Hexabrix™, Mallinckrodt Imaging); iothalamate (Cysto-Conray II™, Mallinckrodt Imaging); and iopamidol (Isovue™, Bracco Imaging).

In some embodiments, the iodine-based moiety is an iodine-substituted aryl moiety (which may comprise one or more aryl groups, e.g., two fused or covalently associated aryl rings) comprising between 1 and 6 iodine atoms. In some embodiments, the iodine-substituted aryl moiety comprises 1, or 2, or 3, or 4, 5 or 6 iodine atoms. In some embodiments, the iodine-substituted aryl moiety comprises 1, or 2, or 3 iodine atoms, the iodine atoms being substituted ortho-, para- or meta- to each other, in case of substitution by 2 iodine atoms; substituted 1,2,3, or 1,2,4, or 1,2,5, or 1,3,5, or 2,3,4 or 1,3,4 relative to each other, in case of substitution by 3 iodine atoms. In other words, each iodine atom may be at neighboring carbons along the aryl moiety, at alternate carbons or at any position relative to each other.

In some embodiments, the iodine-substituted aryl moiety comprises 3 iodine atoms, being substituted at alternate positions on the aryl ring. In some embodiments, the iodine-substituted aryl moiety is a tri-iodo phenyl or a tri-iodo benzyl, optionally substituted. In some embodiments, the iodine-substituted aryl moiety is N-acetyl iopanoamide or acetamido-triiodobenzyl-butanamide, having the structure:

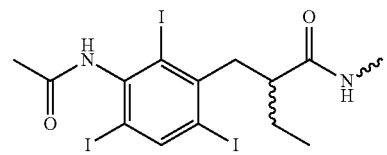

In some embodiments, the CT imaging moiety is a lanthanide-based moiety. Lanthanides with high atomic numbers may be used as CT contrast agents. Among the lanthanides, gadolinium has been most intensively studied for biomedical applications because it is also used as a MRI contrast agent due to its paramagnetic property. Since free lanthanide ions are very toxic, chelating agents such as diethylenetriamine pentaacetic acid (DTPA) and 1,4,7,10-tetraazacyclododecane-1,4,7,10-tetraacetic acid (DOTA) may be employed to reduce the toxicity, and several Gd-chelates are approved by the FDA. In addition, gadolinium may be in the form of gadolinium nanoparticles, optionally coated. In some embodiments, the lanthanide is not gadolinium.

In some embodiments, the imaging moiety may be a bismuth-based moiety. Bismuth-based contrast agents are explored for in vivo use as an alternative to GNPs. Bismuth has a high atomic number (Z=83) and X-ray attenuating properties (absorption edge k=91) and is used as an ingredient in pharmaceuticals and cosmetics. Since metallic bismuth is too reactive to be used in vivo, $Bi_2S_3$ nanoparticles coated with polyvinyl pyrrollidone (PVP) may be used as CT contrast agents. Chelating agents such as diethylenetriamine penta-acetic acid (DTPA) and 1,4,7,10-tetraazacyclo dodecane-1,4,7,10-tetraacetic acid (DOTA) may be used with Bi.

In some embodiments, the CT imaging moiety is a gold-based moiety or a moiety comprising at least one gold metal atom (non-ionic). The gold-based moiety may be a plurality of gold nanoparticles (GNP), each being a colloidal gold nanoparticle that is non-toxic and non-immunogenic. In some embodiments, the GNP is selected to have an average size (average diameter) of between about 5 nm to about 200 nm. In some embodiments, the GNP is selected to have an average size (average diameter) of between about 10 nm and about 100 nm. In some embodiments, the GNP diameter is on average about 10 nm. In some other embodiments, the GNP diameter is on average about 30 nm. In some further embodiments, the GNP dimeter is on average about 100 nm.

The GNPs may be surface-modified or functionalized by surface ligands, e.g., with multiple tumor markers such as antibodies, peptides or small molecules. In general, the targeting efficacy of the functionalized nanoparticles may depend on the nature of the ligand, the selected coupling reaction (or coupling moiety) and the ligand surface density.

It should be noted that the averaged diameter of the GNP may be measured by any method known to a person skilled in the art. The term "averaged diameter" refers to the arithmetic mean of measured diameters, wherein the diameters range ±25% of the mean. For example, an "averaged diameter of between about 5 nm and about 200 nm" encompasses also particles having diameters 25% smaller than 5 nm and 25% larger than 200 nm.

For the purposes of the present invention, the CT imaging moieties may be in the form of nanoparticulate material or element, having a form selected from microspheres, liposomes, micelles, polymeric particles, nanospheres, and nanocapsule, provided that said nanoparticulate forms comprises, holds, encapsulates or is associated with at least one CT contrast agent. Any of the nanoparticulate forms may be a polymeric nanoparticle.

In some embodiments, the CT imaging moiety is selected based on the selection of a carrier moiety.

In some embodiments; where the carrier moiety is at least one macromolecule such as a dendrimer, as defined and selected herein, the CT imaging moiety is an iodine-based moiety, as defined and selected herein.

In some embodiments, where the carrier moiety is at least one oligomer or polymer, as defined and selected herein, the CT imaging moiety is a gold nanoparticle, as defined and selected herein.

In some embodiments, compounds of the invention are dendritic macromolecules associated with one or more iodine-substituted aryl or aliphatic moieties. In some embodiments, the dendritic macromolecule is associated with one or more iodine-substituted aryl moieties. In some embodiments, the iodine-substituted aryl moiety comprises between 1 and 6 iodine atoms. In some embodiments, the iodine-substituted aryl moiety comprises 1, or 2, or 3, or 4, or 5 or 6 iodine atoms. In some embodiments, the iodine-substituted aryl moiety comprises 1, or 2, or 3 iodine atoms, the iodine atoms being substituted ortho-, para- or meta- to each other, in case of substitution by 2 iodine atoms; substituted 1,2,3, or 1,2,4, or 1,2,5, or 1,3,5, or 3,4,5 or 1,3,4 relative to each other, in case of substitution by 3 iodine atoms.

In some embodiments, the iodine-substituted aryl moiety comprises 3 iodine atoms, being substituted at alternate positions on the aryl ring. In some embodiments, the iodine-substituted aryl moiety is a tri-iodo phenyl or a tri-iodo benzyl, optionally substituted. In some embodiments, the iodine-substituted aryl moiety is N-acetyl iopanoamide or acetamido-triiodobenzyl-butanamide having the structure:

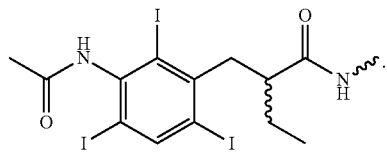

Thus, in some embodiments, compounds of the invention are structured of at least one dendrimer and a plurality of iodine-substituted aryl moieties, at least one of said plurality of iodine-substituted aryl moieties is a tri-iodo aryl such as N-acetyl iopanoamide or acetamido-triiodobenzyl-butanamide having the structure:

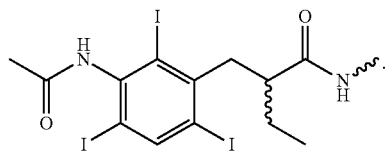

The at least one enzyme interacting moiety is an anchoring group selected to form a bond with an enzyme. The at least one enzyme interacting moiety is selected to comprise one or more functional groups capable of interaction with an enzymatic. The interaction of the enzyme moiety and the enzyme may occur by the following examples: (1) by initial bond cleavage in the enzyme interacting moiety and subsequent attachment to the enzyme (2) by initial bond cleavage in the enzyme interacting moiety, dissociation of a part (at least one bond and/or at least one atom, or combination thereof) of the moiety and subsequent attachment to the enzyme (3) chemical association to the enzyme (without bond cleavage and/or moiety dissociation).

In some embodiments, the interaction of a compound of the invention with the enzyme involves bond cleavage by the enzyme, or dissociation of part of the compound and subsequent attachment thereto. In some embodiments, the association does not involve dissociation. Notwithstanding of the chemical pathway leading to the association of a compound of the invention to the enzyme, the attachment involves formation of a non-labile (non-hydrolizable) covalent bond.

In some embodiments, the at least one enzyme interacting moiety is a group containing an electrophilic atom (or group). Non limiting electrophiles include olefin sulfoxide, α,β-unsaturated carbonyls, acyloxymethyl ketone (AOMK) and epoxide groups. In some embodiments, the electrophilic atom (or group) is susceptible for nucleophilic attack by the target enzyme, resulting in the formation of a non-labile (non-hydrolizable) covalent bond. In some embodiments, the at least one enzyme interacting moiety undergoes bond cleavage by the enzyme prior to bond formation. In some embodiments, the bond is formed during or concomitantly with the nucleophilic attack.

In some embodiments, the at least one enzyme interacting moiety is an AOMK moiety, an epoxide or a phosphonate moiety. In some embodiments, the at least one enzyme interacting moiety may be one or more phosphonate groups. In some embodiments, the at least one enzyme interacting moiety is AOMK moiety.

The at least one enzyme interacting moiety and the plurality of CT imaging moieties are associated with a core skeleton being the carrier moiety, e.g., a dendrimer or ethylene oxide oligomer/polymer. The enzyme interacting moiety and the CT imaging moiety need not be associated to each other directly.

As used herein, the term "moiety", in the context of any moiety recited herein, refers to an atom, a group of atoms or to any functional fragment of a molecule which functions as recited. The moiety may alternatively be in the form of a physical element such as a capsule, a sphere, a nanoparticle, a liposome, etc, of at least one material (e.g., of a single atom or multiple atoms), which contains or which is associated with at least one material, such that it has the intended functionality. In accordance with compounds of the invention, each moiety may be connected, associated or bonded to another moiety via a bond (such as covalent bond, ionic bond, hydrogen bond, complex and any combination thereof), provided that the function of the compound is maintained as defined.

For the sake of brevity, in a compound of the present invention, the following one-letter abbreviations will be used hereonforth:

I designates a CT imaging moiety;
C designated a carrier moiety, such as a dendrimer or a polymer or an oligomer,
M designates an enzyme interacting moiety, as defined.

Thus, in accordance with the present invention, each of moieties I, C and M are covalently bonded to each c her, such that the carrier moiety C, being in some embodiments a dendrimer, and in some other embodiments an oligomer and in some further embodiments a polymer, is associated with both moiety I and moiety M. In some embodiments, the covalent bonding attaching moiety I to C and/or C to M contains one or multiple intervening atoms that serve as spacers.

In some embodiments, the compound of the invention is of the general Formula (I):

I-C-M    (I)

wherein:
I is at least one CT imaging moiety;
C is a carrier moiety;
M is at least one enzyme interacting moiety;
and
wherein each "-" designates at least one covalent bond, or optionally one or multiple intervening atoms or groups of atoms, forming a one-atom or multiple-atom spacer between the indicated moieties.

In some embodiments, the carrier moiety C is associated to the at least one enzyme interacting moiety M via a selectivity determining moiety, D, such that the at least one chemically reactive moiety M, containing, e.g., an acyloxymethyl ketone functional group, is bonded to the selectivity determining moiety, D, which, in some embodiments, is a peptide moiety selected amongst mono-, di-, tri- or tetra-peptide scaffold moieties. These peptide moieties are typically designed to bind specifically to the enzyme, e.g., protease. Thus, in some embodiments, the at least one enzyme interacting moiety, M, is associated to the carrier moiety, e.g., a dendrimer or an oligomer or a polymer, via a selectivity determining moiety, D; a compound of the invention may thus have the general Formula (II):

I-C-D-M    (II).

The selectivity determining moiety, D, in a compound of Formula (II), is selected to be specifically recognized by an enzyme, e.g., a protease. In some embodiments, the selectivity determining moiety is selected to be recognized by cathepsin. In order to enable such a recognition, moiety D is or comprises one or more amino acids.

In some embodiments, the selectivity-determining moiety, D, is a single amino acid which may be associated with capping groups as both its C and N termini. Alternatively, D may be an amino acid sequence, AA, comprising two or more amino acids. The point of connection to the carrier moiety, C, may be any of the nitrogen atoms of the AA sequence or any alpha-carbon of the AA sequence (or of the amino acid in case D is a single amino acid).

In some embodiments, AA is a dipeptide, a tripeptide, a tetrapeptide or any peptide having between 2 and 10 amino acids. The term "peptide", as used herein, refers to amino acid residues, connected by peptide bonds. A peptide sequence is generally reported from the N-terminal end containing free amino group to the C-terminal end containing free carboxyl group. Any reference to an "amino acid" is to any naturally occurring or synthetic or partially synthetic or modified amino acid, as well as amino acid analogs and amino acid mimetics that function in a manner similar to the naturally occurring amino acids. In some embodiments, the amino acid is derived from an amino acid of the general formula $H_2NCHRCOOH$, wherein R is an organic substituent. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

In some embodiments, the amino acid is selected amongst natural amino acids, non-natural amino acids and any combination thereof. In some embodiments, the amino acid is at least one natural amino acid. In some other embodiments, the amino acid is at least one of alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. In some embodiments, AA is selected amongst D-amino acids. In so-ne other embodiments, AA is selected amongst L-amino acids.

In some embodiments, the sequence AA contains at least one hydrophobic amino acid. In some embodiments, AA comprises at least one of lysine and phenylalanine. In some embodiments, AA comprises lysine or phenylalanine.

In some other embodiments, the amino acid is lysine.

In some embodiments, the amino acid is phenylalanine.

In some embodiments, at least one chemically reactive moiety is associated to at least one said amino acid, being in some embodiments, lysine.

In some embodiments, the AA sequence of the enzyme recognition moiety is of the structure:

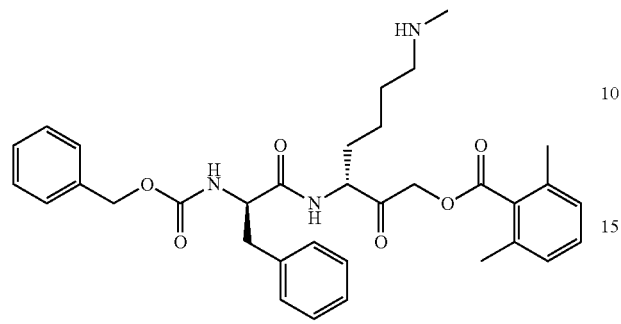

wherein —NH— group extending from the AA sequence is a possible point of connectivity with a linker moiety L or with a carrier moiety.

Each of the amino acids, either at the ends of the AA sequence or at any position along the sequence, may be capped with one or more functional groups assisting in the association to the enzyme. The capping groups may be selected from carbobenzoxy (CBZ), morpholine, pyridine, acetyl, substituted aryl, alloc, nitrobenzyoxycarbonyl (NZ), nitrobenzylsulfonyl (NBS) and 2-chlorobenzyloxycarbonyl (Cl-Z).

In the AA sequence of the enzyme recognition moiety having, in some embodiments, the structure below:

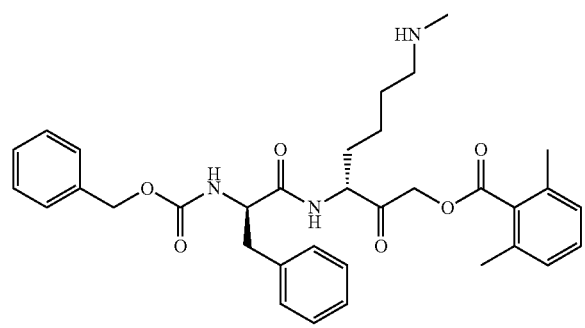 [SMILES: CNCCCC[C@@H](NC(=O)[C@@H](Cc1ccccc1)NC(=O)OCc1ccccc1)C(=O)COC(=O)c1c(C)cccc1C]

the phenylalanine amino acid is N-capped with CBZ, and in turn is associated via a peptide bond with a lysine amino acid that is associated via the carbonyl carbon atom with the AOMK enzyme interacting moiety. The two-amino acid sequence exemplifies a selectivity-determining moiety.

An ABP compound according to some embodiments of the invention comprises a dendrimer associated, directly or indirectly, with:

(a) a plurality of CT imaging moieties, at least a portion of said plurality of CT imaging moieties comprising a tri-iodo aryl such as:

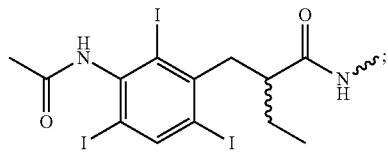

(b) at least one enzyme interacting moiety, being an acyloxymethyl ketone (AOMK) moiety or a phosphonate moiety, or an epoxide moiety; and (c) a selectivity-determining moiety, being an AA sequence, optionally end-capped as selected herein;

wherein the dendrimer is a PAMAM selected from PAMAM (G-1), PAMAM (G-2), PAMAM (G-3), PAMAM (G-4) and PAMAM (G-5).

Each of the PAMAM dendrimers (independent of the particular generation) may be associated, directly or indirectly, with a plurality of CT imaging moieties, as defined, and, further directly or indirectly, with a plurality of chemically reactive moieties, as defined; such that the plurality of chemically reactive groups may be associated with the PAMAM dendrimer via a spacer such as amino acid or an amino acid sequence, AA. In some embodiments, the nitrogen atom of the amino acid e.g., lysine, or of the AA sequence, e.g., comprising a lysine residue, is covalently bonded to the dendrimer groups via a first linker, L, selected optionally from —C(=O)—(CH$_2$)$_n$—C(=O)—; (CH$_2$)$_n$; wherein n is an integer between 1 to 5, and optionally further from a PEG moiety.

An exemplary structure of a compound of the invention is provided for the sake of clarifying the construction of compounds of the invention, as follows:

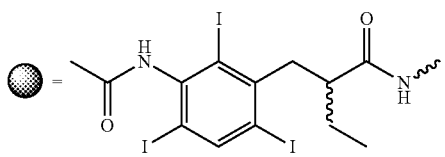

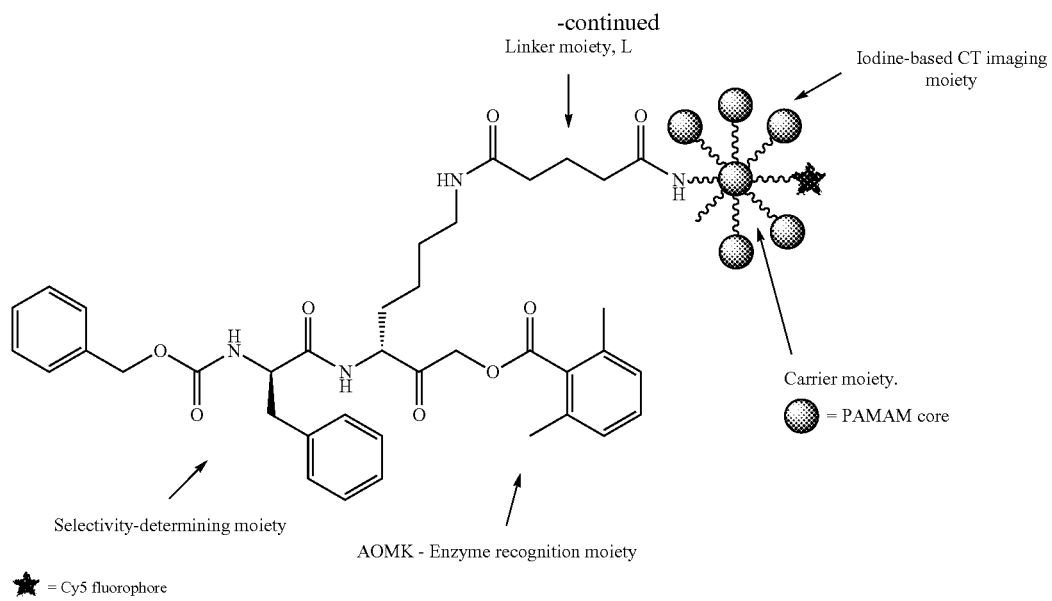

In the above depiction, the wavy lines extending from the carrier moiety, being the PAMAM core, generally depict the internal dendrimer structure, as defined and selected herein, which may be of any generation as selected and defined.

In some embodiments, the compound comprise a fluorescent moiety on the dendrimer PAMAM core. In some other embodiments, the fluorescent moiety is Cy5.

The invention further provides compounds as follows:

1. PAMAM G-0 associated with 1 to 6 iodine-based CT imaging moieties (i.e. tap);
2. PAMAM G-1 associated with between 5 and 8 iodine-based CT imaging moieties;
3. PAMAM G-3 associated with between 10 and 20 iodine-based CT imaging moieties;
4. PAMAM G-1 associated with iodine-based CT imaging moieties, comprising between 10 and 25 iodine atoms; and
5. PAMAM G-3 associated with iodine-based CT imaging moieties, comprising between 40 and 50 iodine atoms.

In some embodiments, an exemplary compound of the invention is:

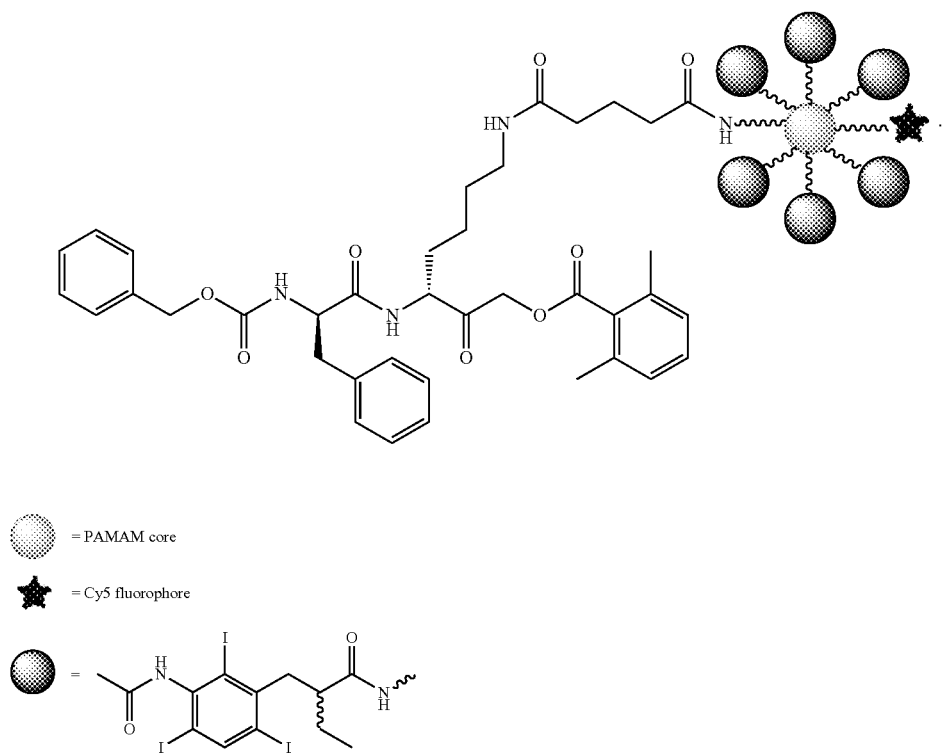

In some embodiments, an exemplary compound of the invention is:

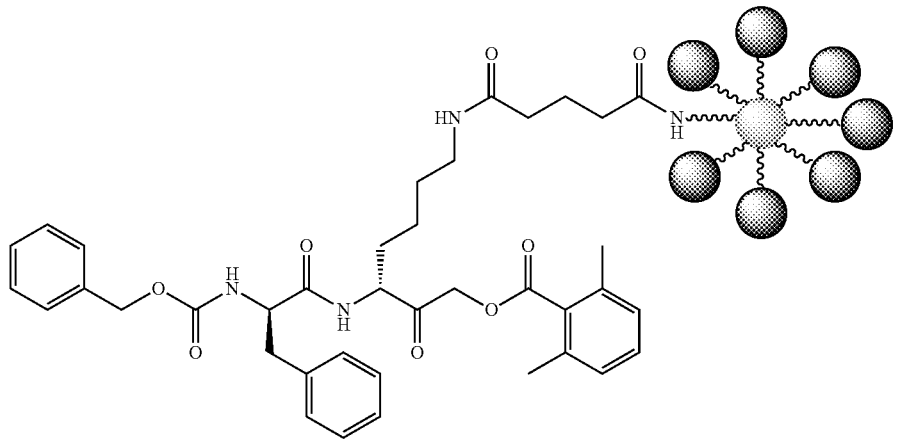

Where,

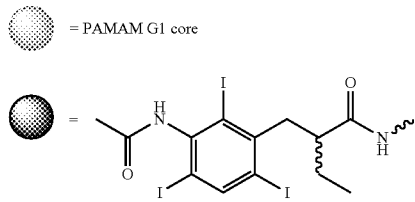 = PAMAM G1 core

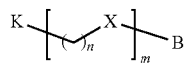 =

In some embodiments, an exemplary compound of the invention is seen in FIG. 20.

The invention further provides compounds wherein the CT imaging moiety is a gold nanoparticle (GNP) or multiple GNPs. In such embodiments, the GNP is associated to an enzyme recognition moiety via a carrier that is selected from oligomers and polymers.

In some embodiments, the carrier moiety comprises at least one oligomer (having between 2 and 10 repeating units) or polymer (having 11 or more repeating units) that is selected from oligopeptides and polyamino acid sequences.

In some embodiments, the carrier moiety is at least one oligo-ether or poly-ether. In some embodiments, the carrier moiety is of the general Formula (CM):

$$K\left[\left(\diagup X\diagdown\right)_n\right]_m B$$

wherein

K is a point of connectivity to a CT imaging moiety and is selected as above, e.g., being optionally —S—;

B is a point of connectivity to an enzyme interacting moiety and is optionally selected as above, e.g., being —C(O)— or -ethylene-C(O)—, wherein at times B is -ethylene-C(O)—;

X is O;

n is an integer from 1 to 20; and m is an integer from 1 to 150.

In some embodiments, m is between 10 and 20, 10 and 30, 10 and 40, 10 and 50, 10 and 60, 10 and 70, 10 and 81, 10 and 90, 10 and 100, 10 and 110, 10 and 120, 10 and 130, 10 and 140, 10 and 150, 50 and 60, 50 and 70, 50 and 80, 50 and 90, 50 and 100, 50 and 110, 50 and 120, 50 and 130, 50 and 140, 50 and 150, 100 and 150, 100 and 140, 100 and 130, 100 and 120 or 100 and 110.

In some embodiments, m is between 60 and 120, 60 and 150, 50 and 70, 100 and 120 or 110 and 115.

In some embodiments, m is between 65 and 70.

In some embodiments, K is —S—, B is -ethylene-C(O)— and X is an oxygen atom.

In some embodiments, the carrier moiety is an oligomer or a polymer of ethylene oxide, being of different lengths and molecular weights. In some embodiments, the oligomer or polymer of ethylene oxide is selected to have a molecular weight of between 800 Da and about 10 kDa. In some embodiments, the oligomer or polymer of ethylene oxide has a molecular weight of between 1 kDa and about 8 kDa. In some embodiments, the oligomer or polymer of ethylene oxide has a molecular weight of between 3 kDa and about 5 kDa. In some embodiments, the oligomer or polymer of ethylene oxide has a molecular weight of 3 kDa. In some embodiments, the oligomer or polymer of ethylene oxide has a molecular mass of 5 kDa. In some embodiments, the oligomer or polymer of ethylene oxide is a mixture of such oligomers and/or polymers of molecular masses between 3 kDa and 5 kDa, or a mixture of such oligomers and/or polymers having a molecular weight of 3 kDa and of such oligomers and/or polymers having a molecular weight of 5 kDa.

The oligomer or polymer of ethylene oxide may be a modified ethylene oxide. In some embodiments, the oligomer or polymer of ethylene oxide is a thiol-polyethylene-glycol. In some embodiments, the oligomer or polymer of ethylene oxide is a thiol-polyethylene-acid.

The GNP is typically associated to the carrier via a thiol group that is present at one end of the carrier. In some embodiments, where the carrier is of the Formula (CM):

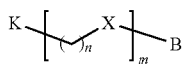

as defined above, K may be —S—, enabling association with a GNP. In such cases, B may be a functional groups selected to enable association with the enzyme recognition moiety, and may thus be optionally selected from —C(O)O—, —C(O)—, —$C_1$-$C_{10}$alkylene-C(O)O—, —$C_1$-$C_{10}$alkylene-C(O)—, —C(O)—$C_1$-$C_{10}$alkylene-C(O)— and —C(O)—$C_1$-$C_{10}$alkylene-C(O)O—. In some embodiments, B is selected from —C(O)O, —C(O), -ethylene-C(O)O, -ethylene-C(O)—, —C(O)-ethylene-C(O)— and —C(O)-ethylene-C(O)O—.

In some embodiments, B is -ethylene-C(O)O— or -ethylene-C(O)—.

In cases where B is —C(O)— or ethylene-C(O)—, association with an amine terminus of an enzyme recognition moiety yields an amide bond.

In some embodiments, m is between 10 and 20, 10 and 30, 10 and 40, 10 and 50, 10 and 60, 10 and 70, 10 and 80, 10 and 90, 10 and 100, 10 and 110, 10 and 120, 10 and 130, 10 and 140, 10 and 150, 50 and 60, 50 and 70, 50 and 80, 50 and 90, 50 and 100, 50 and 110, 50 and 120, 50 and 130, 50 and 140, 50 and 150, 100 and 150, 100 and 140, 100 and 130, 100 and 120 or 100 and 110.

In some embodiments, m is between 60 and 120, 60 and 150, 50 and 70, 100 and 120 or 110 and 115.

In some embodiments, m is between 65 and 70.

Compounds of the invention, utilizing GNP as CT imaging moieties, may thus be depicted as shown below, wherein the AA sequence is:

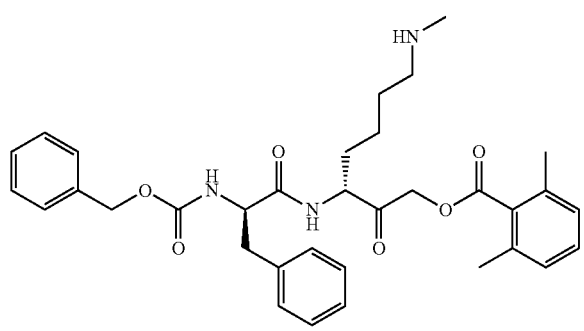 [SMILES: CNCCCC[C@@H](NC(=O)[C@@H](Cc1ccccc1)NC(=O)OCc1ccccc1)C(=O)COC(=O)c1c(C)cccc1C]

the —NH— group extending from the AA sequence is a point of connectivity with a linker moiety L or with the carrier moiety as seen in FIG. 21.

In such GNP-based compounds, the wavy lines depicted as extending from the surface of the GNP designate oligomers or polymers having the general Formula (CM), as defined and selected herein, and may be end-substituted, each, with an enzyme interacting moiety or with a —$CH_3$ group, as depicted.

The GNP used in accordance with the invention, may be any GNP that is non-toxic and non-immunogenic. In some embodiments, the GNP is selected to have a size (diameter) of between 5 nm and about 200 nm. In some embodiments, the GNP is selected to have a size (diameter) of between 10 nm and about 100 nm In some embodiments, the GNP is on average about 10 nm in size.

In some other embodiments, the GNP is on average about 30 nm in size.

In some further embodiments, the GNP is on average about 100 nm in size.

The GNP may be associated with at least one carrier moiety that enables association with the enzyme recognition moiety at its other end. In addition thereto, the GNP may be associated with at least one moiety. Thus, the at least one carrier moiety may be of the Formula (CM), wherein, K may be —S—, enabling association with a GNP, and B may be a functional groups that is, in some embodiments, -ethylene-C(O)—, enabling association with an enzyme recognition moiety, as defined.

Each of the GNP may be further associated with moieties of the Formula (CM1):

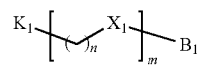

wherein, $K_1$, $X_1$, n and m are selected as for K, X, n and m, respectively in moieties of the Formula (CM), and $B_1$ is selected amongst —$C_1$-$C_5$alkyls, —C(O)— and -ethylene-C(O).

In some embodiments, in the moiety of Formula (CM1), $K_1$ may be —S—, enabling association with a GNP, and B is selected from —$C_1$-$C_5$alkyls, —C(O)— or ethylene-C(O)—. In some embodiments, B is a —$C_1$-$C_5$alkyl, selected from —$CH_3$ and —$(CH_2)_v CH_3$, wherein v is an integer between 2 and 4. In some embodiments, B is —$CH_3$.

In some embodiments, m is between 10 and 20, 10 and 30, 10 and 40, 10 and 50, 10 and 60, 10 and 70, 10 and 80, 10 and 90, 10 and 100, 10 and 110, 10 and 120, 10 and 130, 10 and 140, 10 and 150, 50 and 60, 50 and 70, 50 and 80, 50 and 90, 50 and 100, 50 and 110, 50 and 120, 50 and 130, 50 and 140, 50 and 150, 100 and 150, 100 and 140, 100 and 130, 100 and 120 or 100 and 110.

In some embodiments, m is between 60 and 120, 60 and 150, 50 and 70, 100 and 120 or 110 and 115.

In some embodiments, m is between 65 and 70.

In some embodiments, these moieties of the general Formulae (CM) and (CM1) are PEG chains, as defined above with reference to integers n and m. moieties indicated as PEG-OMe or where the moiety of Formula (CM1) is indicated as having an end group —OMe, is moiety of the Formula (CM1), wherein X is oxygen and B is —$CH_3$ (methyl group, Me).

For the sake of clarity, when referring to PEG-moieties it should be understood as encompassing also an ethylene oxide polymer/oligomer core and modified K and B groups (i.e. K is not necessarily OH and B is not necessarily H). As such, PEG-moieties as used herein include oligomer/polymer of ethylene oxide in which K is —S— and B is ethylene-C(O)—, at times having B as -Me or at times having B as -ethylene-C(O)O— (referred herein as PEG-COOH).

The GNPs may be surface associated with one or both of moieties of the Formulae (CM) and (CM1), namely with moieties that associate the GNPs to the enzyme interacting moieties (CM) and with moieties of the Formula (CM1), wherein Bi is selected amongst —$C_1$-$C_5$alkyls, e.g., —$CH_3$. The ratio between the two moieties may vary. In some embodiments, the GNPs are associated solely (substantially 100%) with moieties that associate the GNPs to the enzyme interacting moieties (CM). In some embodiments, the ratio between the number of (CM) moieties and the number (CM1) moieties, e.g., PEG-OMe may be selected from (CM:CM1) 1:1, 1:2, 1:3, 1:4, 1:5, 1:6, 1:7, 1:8, 1:9, 1:10, 2:1, 3:1, 4:1, 5:1, 6:1, 7:1, 8:1, 9:1 and 10:1. In some embodiments, 5, 10, 15, 20, 25, 30, 35, 40, 45, 50, 55, 60, 65, 70, 75, 80, 85, 90, 95 or 100% of the moieties on the surface of the GNPs are such that associate the GNPs to the enzyme interacting moieties (CM). In remaining moieties are of the Formula (CM1), wherein Bi is selected amongst —$C_1$-$C_5$alkyls, e.g., —$CH_3$.

As described herein, the GNP may have different sizes (diameters). In some embodiments, the GNP is selected to have an average diameter of 10 nm. In some embodiments, the GNP has an average diameter of 30 nm. In some embodiments, the GNP has an average diameter of 100 nm.

In some embodiments, the moiety of Formula (CM) is a PEG moiety associated with an enzyme interaction moiety and the moiety of Formula (CM1) is PEG-OMe.

In some embodiments, where the GNPs are associated solely (substantially 100%) with PEG moieties that associate the GNPs to the enzyme interacting moieties, the PEG moieties may be selected from such having molecular weights of between 3 kDa and 5 kDa. In some embodiments, the molecular weight is 3 kDa. In some embodiments, the molecular weight is 5 kDa.

In some embodiments, where a combination of PEG moieties is present on the surface of the GNP, namely at a selected CM:CM1 ratio, as above, each of the moieties may be selected from such having molecular weights of between 3 kDa and 5 kDa, in some embodiments, molecular weight of 3 kDa, or molecular weight of 5 kDa.

Non-limiting examples of GNPs associated with such moieties are depicted in the Table below:

| Exemplary embodiment | Moiety (CM) | Moiety (CM1) |
|---|---|---|
| 1 | 100%, 3 kDa | |
| 2 | 100%, 5 kDa | |
| 3 | 10%, 3 kDa | 90%, 3 kDa |
| 4 | 10%, 5 kDa | 90%, 3 kDa |
| 5 | 10%, 3 kDa | 90%, 5 kDa |
| 6 | 10%, 5 kDa | 90%, 5 kDa |
| 7 | 50%, 3 kDa | 50%, 3 kDa |
| 8 | 50%, 5 kDa | 50%, 3 kDa |
| 9 | 50%, 3 kDa | 50%, 5 kDa |
| 10 | 50%, 5 kDa | 50%, 5 kDa |

In some embodiments, the CM moiety is a PEG associated with an enzyme interacting moiety and the CM1 moiety is PEG-OMe.

GNPs utilized according to the invention may thus be selected from:
1. GNP associated with a plurality of moieties, 10% of which being 5 kDa PEGs associated each with an enzyme interacting moiety and the others selected from 5 kDa PEG-OMe moieties, as seen in FIG. 22.
The GB 11 is an enzyme interacting moiety.
2. GNP associated with a plurality of moieties, 50% of which being 5 kDa PEGs associated each with an enzyme interacting moiety and the others selected from 5 kDa PEG-OMe moieties, as seen in FIG. 23.
3. GNP associated with a plurality of PEG moieties, 100% of which being associated with enzyme interacting moieties, each via 5 kDa PEG moieties, as seen in FIG. 24.
4. GNP associated with a plurality of PEG moieties, 10% of which being associated with enzyme interacting moieties via 3 kDa PEG moieties and the others selected from 5 kDa PEG-Ome, as seen in FIG. 25.
5. GNP associated with a plurality of PEG moieties, 10% of which being associated with enzyme interacting moieties via 5 kDa PEG moieties and the other selected from 3 kDa PEG-OMe.
6. GNP associated with a plurality of PEG moieties, 50% of which being associated with enzyme interacting moieties via a 3 kDa PEG moieties and the other selected from 5 kDa PEG-Ome, as seen in FIG. 26.
7. GNP associated with a plurality of PEG moieties, 50% of which being associated with enzyme interacting moieties via a 5 kDa PEG moieties and the other selected from 3 kDa PEG-OMe.
8. GNP associated with a plurality of PEG moieties, 100% of which being associated with enzyme interacting moieties via a3 kDa PEG moieties, as seen in FIG. 27.

Compounds of the invention may be used in the preparation of a diagnostic formulation or in the manufacture of a formulation for use in CT imaging. The formulations according to the invention are not intended nor can be used in therapeutic or prophylactic treatment of a subject (human or non-human) and are solely restricted to diagnostic applications. As such, formulations of the invention may comprise apart from a diagnostically effective amount of a compound of the invention, at least one diagnostically suitable liquid, gel or otherwise a carrier of any suitable constitution and from.

The invention thus provides use of a compound according to the invention in a method of diagnosis of at least one human or non-human subject, the diagnosis comprising CT imaging.

The invention further provides formulations comprising at least one compound according to the invention, wherein the compound if optionally present in a diagnostically effective amount.

In some embodiments, the formulation is for determining the site of a disease and/or for distinguishing between healthy and abnormal tissues or organs.

In some embodiments, the formulation is for distinguishing or differentiating between malignant and benign tumors.

In some embodiments, the formulation is for monitoring a disease state in a subject.

In some embodiments, monitoring of a disease stage is directly or indirectly achievable by monitoring the level of metabolism of any one organ directly or indirectly associated with the disease.

Formulations and compounds of the invention may be administrated by any known method in the art. These include, but are not limited to, injection (e.g., using a subcutaneous, intramuscular, intravenous, or intradermal injection), dermal, intranasal administration and oral administration. The amount of a compound according to the invention that may be used in a formulation of the invention, or generally administered to a subject, may be determined by the practitioner to provide an effective diagnosis, e.g., CT imaging. As compounds of the invention are non-toxic, the amount or dosage selected may be such to yield an effective end result. In some embodiments, the dosage may range from about 50 mg/kg per CT session to about 300 mg/kg per session.

Alternatively, the dosage may be 5, 6, 7, 8, 9, 10, 11, 12, 13, 14, 15, 16, 17, 18, 19 or 20 grams per body weight. As used herein, "body weight" generally refers to an average weight of a human subject, being about 70 Kg. The weight may be different and thus the dosage size may vary accordingly.

As described herein, compounds of the invention are specifically constructed to recognize and covalently bind proteases, such as cysteine proteases. In some embodiments, the protease is cathepsin. Cathepsins recognize their substrate target by the sequence around their cleavage site; in most cases, the recognition is up to four amino acids on each side of the scissile bond (the target site for cleavage). As such, compounds of the invention comprise acyloxymethyl ketone (AOMK) which releases a carboxylate leaving group upon modification of a protease target. AOMK is highly selective for cysteine proteases and has low reactivity toward Serine proteases and other biomolecules. Cysteine cathepsins are a family of proteases that share a conserved active site formed by cysteine, aspartic acid and histidine. Besides their main function as degrading proteases in the lysosome, cathepsins regulate several biological processes including, inflammation, antigen presentation, epidermal homeostasis, angiogenesis, extracellular matrix (ECM) turnover and more. Because of their involvement in numerous biological processes, it is not surprising to find them over-expressed in various pathologies such as arthritis, osteoporosis, atherosclerosis, cancer and immune-related diseases. The cysteine cathepsin proteases play critical roles in several cancer processes including angiogenesis, degradation of vascular basement membrane, and activation of angiogenic growth factors. In addition, they degrade ECM components such as collagen IV, fibronectin and laminin. Degradation of such matrices during tumor invasion play a key role in metastasis by promoting migration of malignant cells out of primary tumors. Studies of tumor tissue and cell lines have shown changes in expression, activity and distribution of the cysteine cathepsins in numerous human cancers. Furthermore, the levels, activity and localization of the cathepsins have been shown to be of diagnostic and prognostic values.

Several cysteine cathepsins have been found to be highly expressed and highly active in several cancer tissues such as in melanoma, colorectal, glioma, breast, lung and others. Cathepsins include cathepsins B, cathepsin C, cathepsins F, cathepsins H, cathepsins K, cathepsins L1, cathepsins L2, cathepsins O, cathepsins S, cathepsins W, cathepsins Z (X). Out of the eleven cysteine cathepsins, the three major cathepsins, B, L and S are highly expressed by the tumor stroma cells mainly by tumor-associated macrophages (TAMs) of the microenvironment.

Compounds of the invention are used for the diagnosis of a variety of pathologies that are associated with increased cathepsin expression, namely conditions in which cathepsin is over-expressed, or conditions in which cathepsin plays a role. Such a role can be directly related to pathological conditions or can be indirectly related to such a particular condition.

In some embodiments, the pathologies that are associated with increased cathepsin are proliferative disorders.

In some embodiments, the pathologies that are associated with increased cathepsin are inflammatory disorders.

A proliferative disorder, diagnosed by utilizing compounds of the invention, is a disorder displaying cell division and growth that is not part of normal cellular turnover, metabolism, growth, or propagation of the whole organism. Unwanted proliferation of cells is seen in tumors and other pathological proliferation of cells, does not serve normal function, and for the most part will continue unbridled at a growth rate exceeding that of cells of a normal tissue in the absence of outside intervention. A pathological state that ensues because of the unwanted proliferation of cells is referred herein as a "hyper-proliferative disease" or "hyper-proliferative disorder." It should be noted that the term "proliferative disorder", "cancer", "tumor" and "malignancy" all relate equivalently to a hyperplasia of a tissue or organ.

Non-limiting examples of cancers include blastoma, carcinoma, lymphoma, leukemia, sarcoma, mesothelioma, glioma, germinoma, choriocarcinoma, melanoma, glioblastoma, lymphoid malignancies, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An inflammatory disorder, diagnosed by utilizing compounds of the invention, is a disorder encompassing any immune response. The inflammatory disorder may be an infectious or a non-infectious disorder. Non-infectious inflammatory disorders are any disorder which the activation of macrophages or activated macrophages play a role such as auto-immune disorders and inflammatory disorders which are not infection related, i.e. non-pathogenic, caused by other than an infectious agent (e.g. auto-antigen, hypersensitivity, wound). Not limiting examples include inflammatory diseases of the gastrointestinal tract such as Crohn's disease, inflammatory bowel disease, gastritis, colitis, ulcerative colitis, colon irritable, gastric ulcer and duodenal ulcer, inflammatory diseases of the skin such as psoriasis, inflammatory diseases of the respiratory system such as asthma, allergic rhinitis or chronic obstructive pulmonary disease (COPD), pulmonary fibrosis, sarcoidosis, inflammatory diseases of the musculoskeletal system such as rheumatoid arthritis, osteomyelitis, osteoporosis, or neuritis, systemic sclerosis, inflammatory diseases of the kidneys such as glomerulonephritis, renal ischemia, or renal inflammation; inflammatory diseases of the nervous system such as multiple sclerosis, Alzheimer's disease and HIV-1-associated dementia; autoimmune diseases such as diabetes, type 1 and 2 diabetes mellitus and graft versus host reaction; infectious disease such as nephritis, sepsis, septic shock, endotoxic shock, adult respiratory distress syndrome; inflammatory conditions of the cardiovascular system, such as myocardial infarction, myocarditis, atherosclerosis, hypertensive cardiomyopathy, atheroma, intimal hyperplasia or restenosis or autoimmune disorders such as Multiple Sclerosis (MS), inflammatory arthritis, rheumatoid arthritis (RA).

In some embodiments, the pathologies that are associated with increased cathepsin are any one of the above-mentioned cancers. In some embodiments, the pathologies that are associated with increased cathepsin are pathologies associated with angiogenesis, degradation of vascular basement membrane, and activation of angiogenic growth factors, macrophage-targeted treatment.

In some embodiments, the pathologies that are associated with increased cathepsin are skin disorders. In further embodiments, the pathologies that are associated with increased cathepsin are cardiovascular diseases. In some embodiments, the pathologies that are associated with increased cathepsin are selected from atherosclerosis, osteoarthritis, arthritis, Alzheimer's disease and psoriasis. In some further embodiments, the pathologies that are associated with increased cathepsin are selected amongst parasite infections.

The compounds of the invention may be utilized in a variety of applications: in CT imaging of a subject, in the diagnosis of a pathological condition characterized by increased cathepsin in a subject, and others.

In accordance with another aspect, the present thus provides a method of CT imaging of a subject, the method comprises detecting a signal following irradiation of a subject by an electromagnetic field, said subject having been administered at least one compound according to the invention.

In some embodiments, the method comprises as step of (a) administering to a subject a compound of the invention.

It should be noted that detecting a signal encompasses collecting data possibly in a form of an image. In some embodiments, the method comprises a step of detecting a signal prior to administration of the compound. This may be possible by exposing the subject to irradiation to obtain a detectable signal.

As noted herein, compounds of the invention are suitable for imaging and diagnosis. Diagnosis is required for the identification of specific subjects (sub-population) suffering from a specific disorder, e.g., a pathological condition associated with increased cathepsin.

In another aspect, the invention provides a method for imaging at least one body region of a subject, the method comprising administering to said subject an effective amount of a compound according to the invention, and imaging said at least one body region. In some embodiments, the compound according to the invention is the only (or main) contrast agent used. In other embodiments, it is used in combination with another contrast agent.

In some embodiments, the method of the invention is utilized for determining a site of a disease and/or for distinguishing between healthy and abnormal tissues or organs.

In some embodiments, the method is used for distinguishing or differentiating between malignant and benign tumors.

In a further aspect, the invention provides a method for diagnosis of a disease or disorder in a subject, said method comprising administering to the subject a diagnostically effective amount of a compound according to the invention, and imaging the subject or a body region of the subject to thereby identify body regions in which said compound according to the invention has been localized.

The compound used according to the invention may be utilized for imaging a region or organ of a subject's body after or during treatment or otherwise state of a disease, it may be further utilized in determining severity of the disease, for, e.g., enabling determination of treatment effectiveness and continued treatment. Therefore, the compound may be further utilized in a method for monitoring a disease state in a subject. In such a method, the subject is administered with the compound, the subject's body or any one or more regions thereof is imaged, to obtain at least one imaging parameter indicative of the disease or disorder state, and comparing said at least one imaging parameter to at least one parameter obtained from said subject at an earlier point in time or upon identification of, e.g., at least one symptom associated with said disease or disorder, wherein the comparison permits determining the progression of the disease or disorder state.

Effective monitoring, made possible by utilization of a compound of the invention, involves obtaining multiple parameters indicative of a disease state and progression at various points in time, prior to, during or after commencement of treatment, and comparing the collected data to determine any one therapeutic parameter. The monitoring may be conducted over a period of time, for example every few days or weeks, once a week, once a month, at the onset of treatment and at any time thereafter, etc.

In a further aspect, the invention provides a method for determining the severity of a disease or disorder in a subject, the method comprising administering to said subject a compound according to the invention, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the severity of the disease or disorder in the subject.

In another aspect the invention provides a method for determining the effectiveness of a therapeutic treatment of a disease or disorder in a subject, the method comprising administering to said subject a compound according to the invention, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the effectiveness of the therapeutic treatment of the disease or disorder in the subject.

The determination of the effectiveness of treatment may be achieved at the end of treatment or at any point in time during the treatment period. Generally, and depending on the disease and disease state, the effectiveness is indicated by any one or more changes in the disease state or any symptom associated therewith, such as decreased proliferation.

In some embodiments, the methods of the invention are used for evaluating the effectiveness of drug treatment in cancer treatment, for example, in evaluating the ability of a drug to reduce the size of a tumor or to prevent the tumor from growing, wherein the method comprises imaging the tumor with a compound according to the invention, as disclosed herein, and measuring the size of the tumor, administering the drug to the subject to affect at least one of reduction in the size of the tumor and prevention of growth of the tumor, re-imaging the tumor with the same or different compound and measuring the size of the tumor, and comparing the size of tumor after administration of the drug to the size of the tumor prior to administration of the drug. As compounds of the invention are not intended nor suitable for therapeutic use, the "drug" used for treatment is a material different from any compound used for diagnosis and accordance with the invention.

In another aspect, the invention provides a diagnostic kit, the kit comprising at least one compound according to the invention, or a formulation comprising same; and instructions for diagnostic use.

The invention further provides a toolkit that includes a compound according to the invention in a solid form or as a liquid food form, in a concentration effective for imaging, e.g., in an amount sufficient for CT imaging. The toolkit may comprise the compound in ampules or solid form for use either with an available CT-compatible injector or an infusion pump or as an oral contrast agent.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to 10%.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1F provide pictorial characterization of GNP-based compounds; FIGS. 1A-1C are TEM images of 100 nm (FIG. 1A), 30 nm (FIG. 1B), 10 nm (FIG. 1C) GNP-based compounds; FIG. 1D-1F are UV-Vis spectra of 10 nm (FIG. 1D), 30 nm (FIG. 1E), 100 nm (FIG. 1F) GNP-based compounds.

FIG. 2A represents GNP with a 5 kDa polymer/oligomer, with 10% GB111 substitution; FIG. 2B represents GNP with a 5 kDa polymer/oligomer, with 50% substitution; FIG. 2C represent GNP with a 5 kDa polymer/oligomer with 100% substitution; FIG. 2D represents GNP with 5 kDa and 3 kDa polymer/oligomer, with 10% substitution on the 3 kDa moieties; FIG. 2E represents GNP with 5 kDa and 3 kDa polymer/oligomer, with 50% substitution on the 3 kDa moieties; FIG. 2F represents GNP with a 3 kDa polymer/oligomer, with 100% substitution; FIG. 2G represents control GNP with no GB111 substitutions.

FIGS. 5A-5F are bar graphs showing cell viability determined by methylene blue assay after incubating the cells with various concentrations of GNP-based compounds for 24 hours (FIGS. 5A-SC) and 48 hours (FIGS. 5D-5F), data are presented as the mean f SD (n=6).

FIGS. 6A and 6B are plots of concentrations of contrast agents relative to HU detected by CT: FIG. 6A at 35 keV and FIG. 6B at 85 keV.

FIGS. 7A-7L are non-invasive micro-CT imaging of cancer in mice. CT scans of mice 72 h post-injection of 10, 30 and 100 nm GNPs-ABPs (FIGS. 7B, 7D, 7F) or 10, 30 and 100 nm GNPs (as control) (FIGS. 7A, 7C, 7E) (5 mg gold per mouse); FIGS. 7A-7F—representative CT images of volume rendered 3D images represent X-ray absorption of bones and gold, dashed line circle indicate tumor location, FIGS. 7G-7L—2D axial cross section image of the same mice, accumulation of GNP-ABP at the tumor leads to significant signal enhancement (shown in circle).

FIGS. 8A-8F are graphs showing GNP-based compounds uptake in-vivo in different organs, FIGS. 8A-8C show percentage of tumor volume containing gold, extracted from CT images of tumors at 0, 24, 48 and 72 h after IV injection. The higher accumulation in tumors was detected with 10 nm & 30 nm GNP-ABPs (T) compared to GNP (NT) through all time points. Black bars GNP-compounds (T), white bars GNP (NT, without the active group). FIGS. 8D-8F show average distribution of gold in the main organs 72 hours after injection of GNP-ABPs (T) or GNP (NT) (10, 30, 100 nm) detected by ICP MS.

FIG. 9A shows GNP size comparison in terms of the percent of tumor volume containing gold as analyzed from CT scans post injection, FIG. 9B shows gold accumulation in major organs detected by ICP-MS for 10, 30 and 100 nm of GNP-based compounds (T).

FIGS. 10A-10F are TEM images of section of tumor tissue taken from a tumor bearing mice injected with 10 nm (FIGS. 10A and 10D), 30 nm (FIGS. 10B and 10E) or 100 nm (FIGS. 10C and 10F) GNP-probe as GNP-ABP (T) (FIGS. 10A-10C) or GNP (NT—no ABP) (FIGS. 10D-10F), Scale bars are: 2 μm to 200 nm.

FIGS. 11A-11F biochemical evaluation of iodine-based compounds: FIGS. 11A-11D show labeling of recombinant cathepsins B (FIGS. 11A and 11D) and recombinant cathepsins L activity (FIGS. 11B and 11E) by IN-ABPs by competitive assay, FIGS. 11C and 11F show cell permeability of IN-ABPs, detection of cathepsin inhibition in NIH-3T3 intact cells by labeling of residual protease activities by competitive assay.

FIG. 12A shows labeling of recombinant cathepsins B activity with IN-ABPs by competitive assay, FIG. 12B shows recombinant cathepsins L activity with IN-ABPs by competitive assay, FIG. 12C shows direct labeling of recombinant cathepsin B by Cy5 labelled IN-ABPs, FIG. 12D shows direct labeling of recombinant cathepsin L by Cy5 labeled IN-ABPs, FIG. 12E shows cell permeability of IN-ABPs, detection of cathepsin inhibition in NIH-3T3 intact cells by labeling of residual protease activities by competitive assay, FIG. 12F shows detection of cathepsin labeling in NIH3T3 intact cells by direct labeling of protease activity in comparison to small fluorescent cathepsin ABP GB123.

FIGS. 14A-14D show signal to background of tumor fluorescence using IN-ABP (FIG. 14A) and control contrast agents (FIG. 14C), tumor bearing mice were injected with Cy5 labeled IN-ABP (in dark diamonds) and control compounds (in light triangles), Non-invasive fluorescence was monitored prior and post injection up to 8 hours using an in vivo Imaging System (IVIS) Kinetic equipped with a 640 nm excitation filter and Cy5 emission filter and the Fluorescent signals were quantified at the tumor area and on the back of the mouse as the background. The tumor to background ratio is presented, IN-ABPs show significantly higher tumor to background signal.

FIGS. 15A and 15B are bar representations showing pharmacokinetics in vivo X-ray computed tomography, FIG. 15A—in vivo pharmacokinetic comparative study of IN-ABP HG92 and HG31, FIG. 15B—in vivo pharmacokinetic comparative study of IN-ABP HG90 and HG99.

FIGS. 16A and 16B show in vivo X-ray computed tomography, FIG. 16A representative picture of a mouse before and 24 h post-injection of IN-ABP (HG92), FIG. 16B show a representative picture of a mouse before and 24 h post-injection of control IN-ABP (HG31).

DETAILED DESCRIPTION OF EMBODIMENTS

Figure 2A:
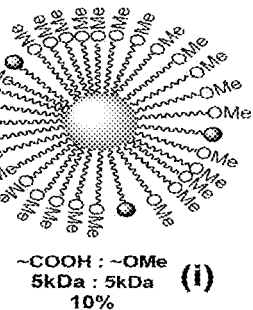
FIGS. 2A-2G are structural depictions representing various derivatives of GNP-based compounds with GNP size of 10 nm, 30 nm and 100 nm; the curved lines represents ethylene oxide polymer/oligomer of molecular weights 5 kDa or 3 kDa, as indicated, —OMe and COOH denote groups at most-exposed ends of the ethylene oxide polymer/oligomer, COOH denotes points of interaction with the enzyme interacting moiety ("GB111"), the % values indicate % of GB111 substituted ethylene oxide polymer/oligomer relative to the total number of ethylene oxide polymer/oligomers on a GNP.
Figure 2B:
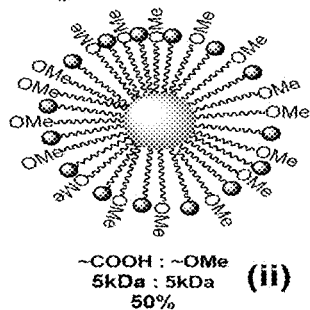
Figure 2C:
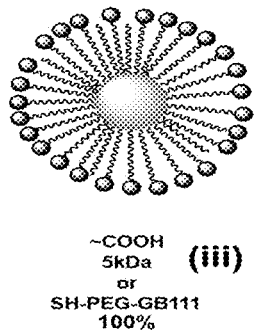
Figure 2D:
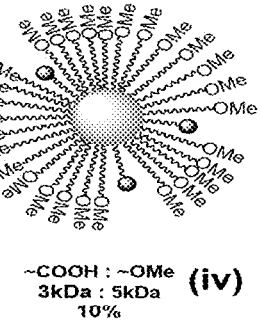
Figure 2E:
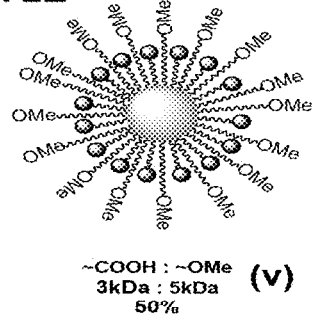
Figure 2F:
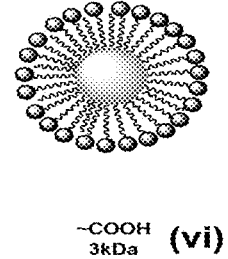
Figure 2G:
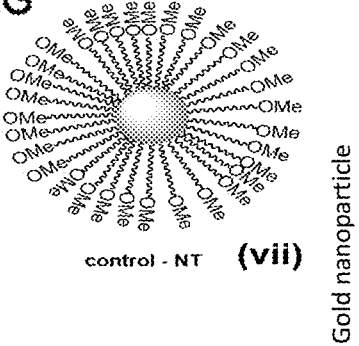

Example 1: Gold Derivatives of Activity Based Probe

Synthesis of GB111-NH$_2$: Fmoc-Lys(Boc)-AOMK (365.2 mg, 0.594 mmol) was de-protected by 25% trifluoroacetic acid (TFA)/dichloromethane (DCM) (v/v) during 30 minutes to receive the free amine, solvent was removed by co-evaporation with toluene in vacuo. 2-Chlorotrityl chloride resin (371.1 mg) was loaded by shaking of resin with the Fmoc-Lysine(NH$_2$)-AOMK (1 eq.) dissolved in anhydrous DCM and diisopropylethylamine (DIEA) (3.5 eq, 360µl) for 1.5 hours. Methanol (1 ml/gr resin) was added, and the resin was shaken for 30 minutes followed by washing with DCM and DMF. The Fmoc protecting group was removed by two quick washes with 5% diethylamine (DEA)/DMF (v/v) followed by a 5 min incubation with 5% DEA and then washed with DCM and DMF. De-protection was verified by Kiser test. The peptide was elongated by addition of a solution of N-benzyloxycarbonyl-phenyalanine (Cbz-Phe), (3 eq., 226 mg), Hydroxybenzotriazole (HOBT), (3 eq., 101.3 mg) and benzotriazol-1-yl-oxytripyrrolidino phosphonium hexafluorophosphate (PyBOP), (3 eq., 116 mg) in DMF for 2 hours. The resin was then washed with DCM and DMF and the final peptide product was cleaved from the resin by addition of 7% TFA/DCM (v/v) for 7 to 15 minutes. The cleaved solution was collected and solvent was removed by co-evaporation with toluene. The crude peptide was further dried in vacuo and purified by HPLC. GB111-NH$_2$ eluted at 44% ACN to yield a white powder, 78.94 mg, 0.138 mmol, M/z+1 574, 56% yield relative to resin loading. Scheme 1 shows GB111NH$_2$ synthesis.

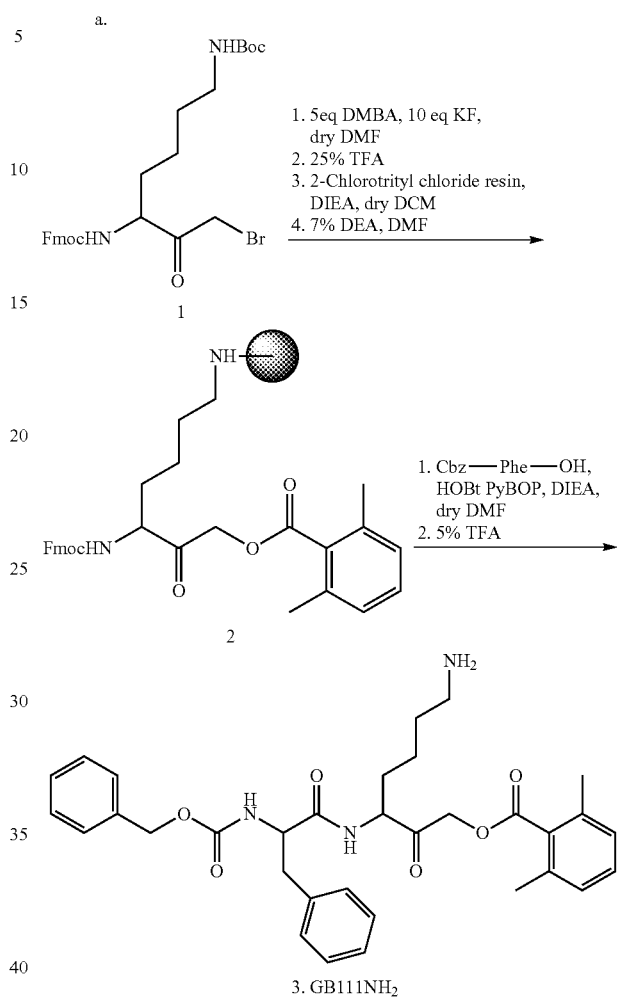

Scheme 1
Synthesis of GB111-NH$_2$

Synthesis of PEGylated gold nanoparticles: GNP stabilized in citrate buffer were purchased from Cytodiagnostic Inc. at three different sizes: 10, 30, 100 nm. A protective layer of PEG was absorbed on the surface of the GNPs at different molar ratios and different lengths consisting of a mixture of thiol-polyethylene-glycol (mPEG-SH) and a heterofunctional thiol-polyethylene-acid (SH-PEG-COOH) (Creative PEGWorks, Winston Salem, N.C.).

In a typical process, to 1.0 ml of GNP solution (OD 1) was added 11 µl of PEG mixture solution at different concentrations to obtain the following final molar ratios: 10, 1, 0.1, 0.01 mM. The reaction mixture was vortexed immediately and then incubated at room temperature for two hours. After PEGylation, each solution was centrifuged at 14000, 9400, 8600 rpm (10, 30, 100 nm respectively) for 20 min and re-dispersed with Milli-Q water by gentle shaking. This process was repeated three times. From the resultant supernatant solution a small part was analyzed by measuring absorption spectra, hydrodynamic size and zeta potential. The mixture was stored in refrigerator at 4° C. PEGylation at 0.01 mM final concentration was found to be the most efficient and stable.

Conjugation of GB111-NH2 to PEGylated gold nanoparticles: PEG-GNP were re-dispersed in 1 ml of DMF:DDW (1:10) several times. EDC (1.13 μmol, 0.21 mg) and NHS (1.13 μmol, 0.13 mg) 1.5 eq relative to the PEG-COOH moiety, were dissolved together and added to GNP-PEG solution for 30 min. at room temperature, providing active sites on GNPs that further undergo amidation reaction with the GB11-NH$_2$. The amount of peptide added is 0.38 mg (75 nmol) per 2.5 mg of molecular gold (1:1 ratio to activated moiety). The mixture was incubated overnight at room temperature followed by centrifugation and re-dispersion in DMF to remove unbound peptide in the solution.

Preparation of HS-PEG-GB111 and PEGylatien to GNPs: Anhydrous DMF (3 ml) was added to dissolve the ortho-pyridyldisulfide-PEG-succinimidyl ester (OPSS-PEG-NHS, 5 kD) powder (1 eq., 10 mg, 2 μmol), then 1.14 mg (1 eq., 2 μmol) of GB111-NH$_2$ was added and mixed in, and finally DIEA (3 eq., 1.0 μL, 6 μmol) was added. The solution was stirred at room temperature for 2 hours. The product fraction was lyophilized and purified by HPLC. The OPPS-HS-PEG-GB 111 conjugate, eluted at 65% ACN to yield a yellowish powder, 8.1 mg, 1.45 μmol, 73% yield.

Dithiothreitol (DTT)-3.37 mg (3 eq., 21.8 μmol) and DIEA (6 eq., 43.6 μmol) were dissolved in 1.5 μL MeOH then added to the dissolved OPPS-SH-PEG-GB111 36.3 mg (1 eq., 7.2 μmol) in 674 μL DDW to give 1M concentration. The reaction mixture was stirred for 3 h to reduce the disulfide and obtain a free thiol at the end of the PEG-GB 111 polymer. The resultant powder was harvested through precipitation in dry diethyl ether. PEGylation using HS-PEG-GB111 to GNPs at 0.01 mM molar ratio was carried out in the same way as for HS-PEG-COOH. After centrifugation was performed three times, the final GNP pellets were re-suspended in 0.2 ml Milli-Q water to concentrate the solution.

Chemical evaluation: Dynamic light scattering (DLS) and ζ potential measurements were conducted in DDW using a Zetasizer nano-ZSP (Malvern). Transmission electron microscopy (TEM) analysis was performed using JEOL JEM-1400Plus by applying ~10 μl of samples resuspended in DDW to a 200 or 400-mesh copper grids covered by carbon-stabilized Formvar film (SPI, West Chester, Pa.). The samples were dried over night before scan performed at different kV. Thermogravimetric analysis (TGA) to establish the mass ratio between organic moiety (PEG) and gold atoms was performed using Mettler Toledo instrument. Temperature Program: heat from 30° C. to 450° C. with rate of 10° C./min in nitrogen atmosphere with a purge rate of 20 mL/min. This protocol led to a density of 0.21 PEG/nm$^2$, which corresponds to the low PEG density particle group (density lower than 1 PEG/nm$^2$). This result is consistent with the low concentration of PEG mixture taken for the process.

Recombinant cathepsin labeling: Recombinant human Cathepsin-B, 0.7 μg or Cathepsin-L, 0.6 μg or Cathepsin-S, 0.7 μg in reaction buffer (50 mM acetate, 2 mM DTT and 5 mM MgCl$_2$ at pH 5.5) were treated in room temperature with inhibitor (GNP-PEG-GB111) 0.01-10 μM probe or vehicle for 1 hour. Indicated concentrations of GB123 were added to samples for 30 minutes at r.t. The reaction was stopped by addition of sample buffer x4 (40% glycerol, 0.2M Tris/HCl 6.8, 20% b-mercaptoethanol, 12% SDS and 0.4 mg/ml bromophenol blue), samples were boiled, separated on a 12.5% SDS gel and scanned for fluorescence by Typhoon scanner FLA 9500, excitation/emission 650/670 nm.

Evaluation of probes permeability to intact cells, competition assay: NIH-3T3 cells (1×10$^5$ cells/well) were seeded in a twelve-well plate one day before treatment. Cells were treated with vehicle or 0.1, 1, 10 μM probes that were pre-dissolved in 0.1% DMF, 0.9% DDW. After 4, 6 or 24 hours of probe incubation residual cathepsin activity was labeled with GB123 (1 μM). Cells were washed with PBS and lysed by addition of sample buffer. Lysates were boiled for 10 minutes and centrifuged. Protein determination was performed by butterfly assay and separated by 12.5% SDS gel. Residual labeled proteases in cells were visualized by scanning the gel with a Typhoon scanner FLA 9500, excitation/emission wavelengths of 650/670 nm. Direct labeling was preformed similarly, after probe treatment cells were lysed and equal protein was separated by Gel that was scanned for Cy5 fluorescence.

Cells viability assay: NIH-3T3 cells (5×10$^3$-24 h, 3×10$^3$-48 h) and 4T1 cells (6×10$^3$-24 h, 4×10$^3$-48 h) were seeded in 96-well plate and incubated for 24 h for cell attachment. GNP-ABPs dispersed in fresh culture media were added at equivalent concentration to each well (200 μl) and incubated for 24 or 48 hours at 37° C. After continuous exposure to various concentrations of GNP-ABPs, the medium was discarded to remove free particles in the solution and cell survival was investigated by standard methylene blue assay.

Animal Care: All animals were maintained on a 12:12 h light/dark cycle under fixed conditions of temperature (23 C) and humidity (50%), with free access to food and water. All experimental procedures were approved by the Animal Care Committee of Hebrew University of Jerusalem and in accordance with the NIH Guide for the Care and Use of Laboratory Animals.

In vivo imaging: 4T1 cells were grown to subconfluency, followed by detachment with trypsin, spin down and resuspention in 0.5% BSA in sterile PBS and 25% matrigel. Cells (1×10$^6$ per spot in a total volume of 20 μl) were injected subcutaneously at the indicated locations into 3-4 week-old male BALB/c mice under isoflurane anesthesia. Tumors were typically established 9-11 days after cells injections, compounds were injected intravenously via the tail vein as follows: in a total volume of 200 μl from stock solution of 25 mg/ml (5 mg of GNP per mouse). Mice anesthetized with isoflurane were imaged before, at 24, 48 and 72 hours post injection. Micro-CT scanner (Skyscan High Resolution Model 1176) equipped with 64 detectors with a nominal resolution of 35 μm was used (0.2 mm aluminum filter, a tube voltage of 40 kV and 500 mA). Reconstruction was performed using SkyScanNRecon software. Ring artifact reduction, Gaussian smoothing (3%), and beam hardening correction (25%) were applied. Volume rendered three-dimensional (3D) images were generated using SkyScan CT-Volume ("CTVol") software.

Flame Gold Analysis (ICP-MS): The tissues obtained from the experimental animals were melted with aqua regia acid, a mixture of nitric acid and hydrochloric acid in a volume ratio of 1:3. The samples were then evaporated, filtered and diluted to a final volume of 7 mL. Au wavelength lamp was used in order to determine the gold concentration in the samples. A calibration curve with known gold concentrations was prepared (commonly: 1, 2, 5 and 10 mg/L). Gold concentration in each sample was determined according to its absorbance value with correlation to the calibration curve. Each sample was analyzed in triplicate and averages and standard deviations were taken.

Preparation of tissues for transmission electron microscopy: Tissue was dissected from animal into PBS (Phosphate Buffered Saline pH 7.4) and fixed in 2% paraformaldehyde, 2.5% Glutaraldeyde in 0.1M Cacodylate buffer (pH 7.4) for several hours at room temp. The tissues were then rinsed 4 times, 10 minutes each, in cacodylate buffer and post fixed and stained with 1% osmium tetroxide, 1.5% potassium ferricyanide in 0.1M cacodylate buffer for 1 hour. Tissues were then washed 4 times in cacodylate buffer followed by dehydration in increasing concentrations of ethanol consisting of 30%, 50%, 70%, 80%, 90%, 95%, for 10 minutes each step followed by 100% anhydrous ethanol 3 times, 20 minutes each, and propylene oxide 2 times, 10 minutes each. Following dehydration, the tissues were infiltrated with increasing concentrations of Agar 100 resin in propylene oxide, consisting of 25, 50, 75, and 100% resin for 16 hours each step. The tissues were then embedded in fresh resin and let polymerize in an oven at 60° C. for 48 hours. Embedded tissues in blocks were sectioned with a diamond knife on an LKB 3 microtome and ultrathin sections (80 nm) were collected onto 200 Mesh, thin bar copper grids. The sections on grids were sequentially stained with Uranyl acetate for 5 minutes and Lead citrate for 2 minutes and viewed with Tecnai 12 TEM 100 kV (Phillips, Eindhoven, the Netherlands) equipped with MegaView II CCD camera and Analysis® version 3.0 software (SoftImaging System GmbH, Münstar, Germany).

Results:

Synthesis of single GNP-ABPs was done. Briefly, the peptide was synthesized using Solid-phase peptide synthesis (SPPS), starting with Boc protected Fmoc-Lysine bromomethyl ketone that was reacted with dimethyl benzoic acid in solution to form the AOMK. Next, the Boc protecting group was removed to receive Fmoc-Lysine ($NH_2$)-AOMK, that was loaded on a chlorotrityl resin via ε-amine of the lysine. The Fmoc protecting group was removed and the Lysine-AOMK was elongated via the free amine of the lysine with protected Cbz-Phenylalanine-OH. The dipeptide-AOMK was cleaved from the resin and purified by HPLC to give GB111-$NH_2$ with 56% yield (data not shown).

The surface modification conditions of GNP stabilized in citrate buffer were evaluated. A protective layer of PEG was absorbed on the surface of the GNPs at different molar ratios and different lengths consisting of a mixture of thiol-polyethylene-glycol (mPEG-SH) and a heterofunctional thiol-polyethylene-acid (SH-PEG-COOH) (Creative PEGWorks, Winston Salem, N.C.). In a process, to GNP solution (OD 1) a PEG mixture solution was added at different concentrations to obtain the following final molar ratios: 1, 0.5, 0.1, 0.01 mM. The reaction mixture was vortexed immediately and then incubated at room temperature for two hours. After PEGylation, each solution of 10, 30, 100 nm was centrifuged at 14000, 9400, 8600 rpm, respectively, for 20 min and re-dispersed with Milli-Q water by gentle shaking. Average size of PEG-GNP was confirmed by both dynamic light scattering (DLS) and TEM spectroscopy.

The stability of PEG-GNPs was performed by ZETA potential spectroscopy and was evaluated immediately after preparation and 2, 4 weeks following the preparation with no change.

TABLE 1

Size and ZETA potential of 10 nm, 30 nm and 100 nm GNPs-compounds as described herein

| GNP-ABPs | Size [d, nm] | Zeta [mV] |
| --- | --- | --- |
| 10 nm | 34.39 ± 0.4 | −21.1 ± 2.1 |
| 30 nm | 75.75 ± 0.2 | −24.0 ± 1.3 |
| 100 nm | 137.4 ± 0.1 | −25.7 ± 0.4 |

Characterization of GNP-PEG-GB111 at different sizes of 10, 30, 100 nm is shown in FIG. 1A-1F. FIG. 1A-1C demonstrates the core size of the probe and FIG. 1D-1F show that each probe exhibit a unique wavelength representing its size before (dashed line) and after (full line) chemical modifications. As can be seen, 10 nm-521 nm, 30 nm-524 nm and 100 nm-574 nm. For each size, bare GNPs and GNP-ABPs were measured. The absence of shift indicating GNP stability.

In order to proceed with these GNP-ABPs to biochemical evaluation, a quantitative analysis to determine the amount of peptide on each particle was performed. thermogravimetric analysis (TGA) was used to establish the mass ratio between organic moiety (PEG) and gold atoms. Because PEG has a simple linear-chain-bond structure, which consist of —C—O— and —C—C— in the backbone chain with a similar bond energies (82~83 kcal/mol), thermal dissociation occurs in a narrow temperature range. The main step is seen at the beginning stands for $H_2O$ evaporation (11 minutes) and partially breakage of PEG bonds. At 330° C. the second step is seen, which represents the PEG burning of 18.9 μg (data not shown).

PEG density→0.21 PEG/$nm^2$ on 30 nm GNP

Based on these calculations, the number of peptide moiety on each particle was estimated for further biochemical evaluation.

FIGS. 2A to 2G show the library of GNP compounds with different GNP size of 10 nm, 30 nm and 100 nm that were generated. Different percentages of PEG-COOH moiety were used to bind GB111$NH_2$ ("GB111"). The polyethylene oxide was modified with OMe or COOH groups at one end of the ethylene oxide polymer/oligomer. As the COOH groups were used to bind ABP, the % denoted in each one of the Figs. indicate the % of COOH groups being substituted with ABP and as such the % denoted the % of ABP substituted ethylene oxide polymer/oligomer relative to the total number of ethylene oxide polymer/oligomers on a GNP.

Based on the in vitro results shown herein, the GNP with 10% ABP with ABP substituted on the shorter PEG (3 kDa) and OMe on the 5 kDa PEG was selected for further in vivo analysis with different sizes of 10 nm, 30 nm and 100 nm Biochemical Evaluations The biochemical evaluation of these probes started with evaluation for their ability to bind recombinant human cathepsins B. Recombinant human cathepsins B was incubated with increasing concentrations of the probes for 1 hour. Residual activity was detected by a fluorescently labeled cathepsin ABP that was added to samples for 30 minutes at r.t. The free probe was separated from the enzyme-probe complex by SDS PAGE, the detection of the probe-enzyme complex was done by a fluorescent scanning of the gel at Cy5 fluorescence.

Figure 3:
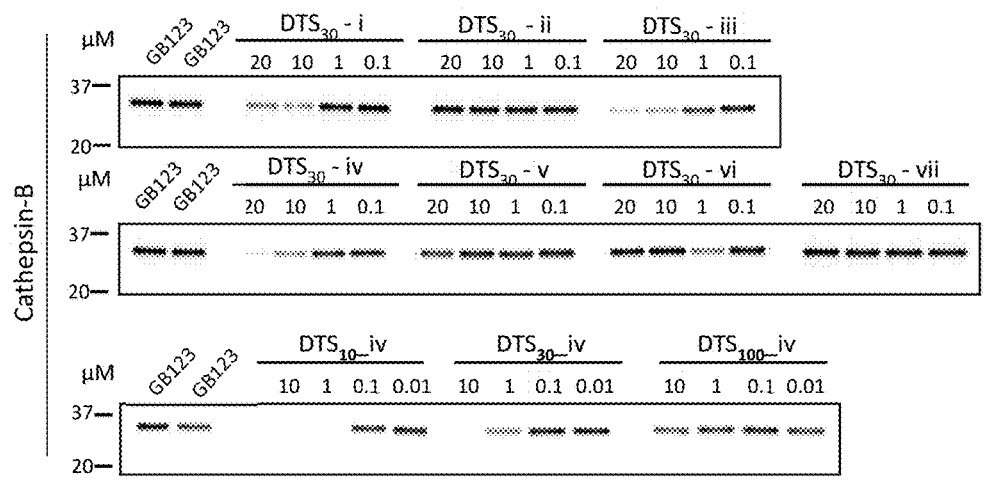
FIG. 3 shows SDS gels exhibiting competitive inhibition of recombinant cathepsin B GNP-based compounds; the indicated concentrations of probes were added to samples for 1 h, followed by 30 min labeling of the residual activity with GB123, a fluorescent tag, the samples were separated on SDS gel and scanned for fluorescence.

FIG. 3 shows blots of GNP-ABP derivatives (structures presented in FIG. 2) indicating that 30 nm GNP-ABP derivatives showed competitive inhibition of recombinant cathepsin B (10 and 100 nm) showed the same pattern, shown in bottom panel for DTS-(iv). Derivatives DTS-(ii) and DTS-(v) baring 50% targeting moiety showed no inhibition activity at all.

However, compound DTS-iv, 10% targeting moiety on 3 kDa PEG, for all particle sizes showed competitive inhibition of recombinant cathepsin B. Size dependent inhibition was observed.

Figure 4:
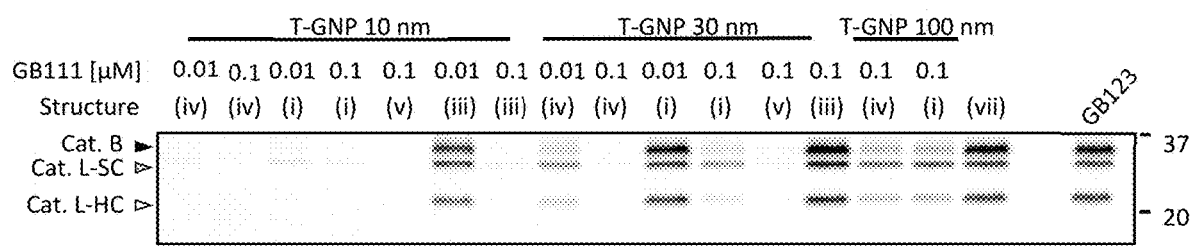
FIG. 4 shows SDS gels exhibiting inhibition of endogenous cathepsin activity in intact NIH3T3 cells.

Evaluation of the probes cell permeability and capability of labeling cellular cathepsin enzymes was performed using competitive inhibition assay as well. The competitive inhibition assay was carried out by incubation of NIH-3T3 cells with GNP probes for 4, 6 and 24 hours. Next, the residual cathepsin activity was labeled by GB123 1 μM during 2 hours. Cell lysates were separated on SDS-PAGE followed by scanning the gel for fluorescence at: 650/570 nm to visualize labeling of residual cathepsin activity by GB123. FIG. 4 shows results obtained with different GNP-ABPs in NIH3T3 cells (4T1 cells showed a similar pattern—data not shown) which were treated with indicated probes in growth medium for 4 h followed by labeling of residual enzyme activity by GB123 for 2 hours. A control DTS-(vii) was applied. A dose response inhibition of cathepsin activity was detected with the probes. Size dependent pattern was observed, the smaller the particle—the higher the enzyme inhibition.

Prior to using the GNP-ABPs in non-invasive animal model, their biocompatibility was evaluated on NIH-3T3 and 4T1 cells, selected as model for normal and cancer cells respectively. Viability was determined by methylene blue assay after incubating the cells with increasing concentrations of GNP-ABPs for 24 and 48 hours (FIGS. 5A-5F). As can be seen, GNP-ABPs for 24 and 48 hours displays only minor cytotoxicity with 10 nm probes at the highest concentration tested for 48 hours.

Figure 6B:
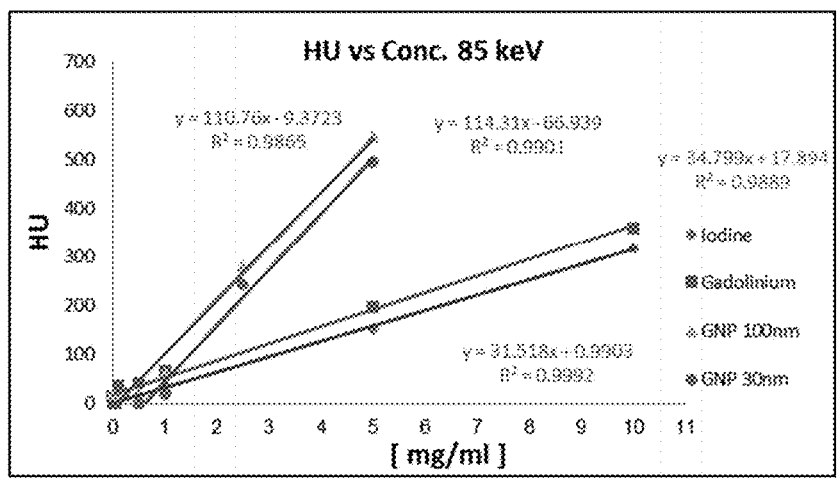
Figure 7A:
Figure 7B:
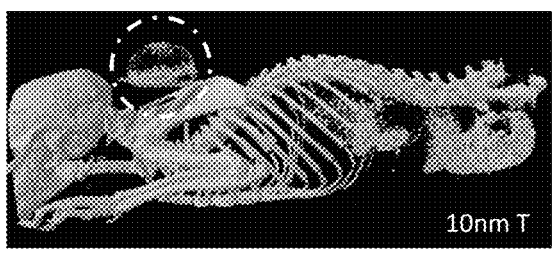
Figure 7C:
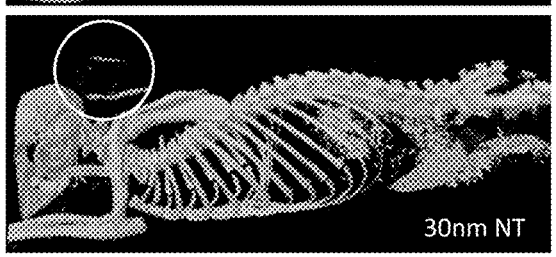
Figure 7D:
Figure 7E:
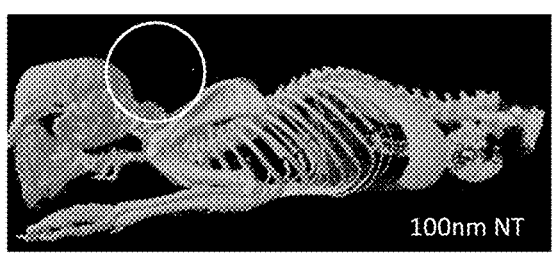
Figure 7F:

The detection level of the various tags using dual energy micro—CT (Skyscan) was evaluated. Each tag was scanned separately in increasing concentrations (0.010 to 10 mg/ml) using a poly-propylene 384 well plate. FIG. 6 shows HU detected by CT as a function of the contrast agent concentration. As can be seen linear correlation were detected with $R^2$ above 0.98 for all contrast agents in both low energy 35 keV, and high energy 85 keV. The minimal detected concentration in water are presented in Table 2.

TABLE 2

The minimal detected concentration of gold, gadolinium and iodine by dual beam micro-CT at high and low energies.

| | [mg/ml] | HU | Beam E |
|---|---|---|---|
| GNP 30 nm | 1 | 29 ± 3.5 | 35 keV |
| GNP 30 nm | 1 | 20 ± 8.8 | 85 keV |
| GNP 100 nm | 0.5 | 13 ± 3.5 | 35 keV |
| GNP 100 nm | 0.1 | 16 ± 8.8 | 85 keV |
| Gadolinium | 0.05 | 17 ± 3.5 | 35 keV |
| Gadolinium | 0.1 | 38 ± 8.8 | 85 keV |
| Iodine | 0.05 | 10 ± 3.5 | 35 keV |
| Iodine | 0.5 | 15 ± 8.8 | 85 keV |

Non-Invasive Imaging of Cancer in Mice Modules

To determine the efficacy of targeting compared to passive mechanism of GNP-ABPs syngeneic mouse model was used. 4T1 cells were injected subcutaneously on the back of 3-4 week-old male BALB/c mice under isoflurane anesthesia. After tumors were established, each mouse received 200 µl of a 25 mg/ml solution of targeted or control GNP-ABPs by tail vain injection. The mice were scanned before, at 24, 48 and 72 hours post injection by a Micro-CT scanner.

The need to perform comparative analysis between different mice injected with different size of GNPs, lead us to seek for different approach than HU quantification that might be misleading in this case. The diversity in size tumor dictates different X-ray absorption values in different mice as well as the same mouse scanned at different time points. Larger tumor, exhibit higher HU values derived from tumor volume but not necessary due to GNP uptake per gram tissue. To quantify the exact amount of GNPs that reached the tumor tissue in each time point the tissue absorbance and GNP absorbance were analyzed for the same ROI apart. The number of voxels for soft tissue absorbance characterized by low energies, hence was defined by us as 25-255 in gray scale, while gold (and bone) 53-255 for higher energies. The minimum threshold for gold detection was derived from pre-scan of the mouse, showing no voxels in the tumor at that grayscale index. After total voxel number was derived from the image for each range, the labeling percentage of voxels per each tumor was calculated (% labeling=num. of $vox_{53-255}$/num. of $vox_{25-255}$). Significant CT signal enhancement from the tumor could be detected after 24 hours for targeted 10 nm and 30 nm GNP-ABP probe than that of non-targeted nanoparticle (without ABP). This specific signal increased over time and became highly elevated at 72 hours post probe injection excluding the 100 nm GNP-ABP, which exhibited poor active and passive accumulation through all time points as presented in volume rendered 3D and 2D axial cross section images FIG. 7A-7L. The smaller non targeted ABPs accumulated to certain steady state concentration due to EPR effect, slightly enhancing the CT signal. Accumulation of targeted-GNP showed a uniform accumulation in the peripheral region of the tumor, presumably due to solid nature of the tumor. Derived images reflected a pattern of which larger size of GNP-ABPs, lead to lower tumor uptake. The highest signal enhancement was detected with 10 nm targeted ABP.

Bio-Distribution of GNP-ABPs

Probe distribution was monitored to follow pharmacokinetics and signal accumulation in the tumors. After the last time point, the mice were sacrificed and the tumor and other selected organs were taken to inductively coupled plasma mass spectrometry (ICP-MS) tests to determine the gold amount accumulated in each organ. As seen in FIG. 8D-8F, GNP-ABPs showed gold uptake in the spleen, kidney and liver for both pathways: passive and active. As previously published, contrast agents larger than 6 nm avoid renal clearance, hence excreted from the blood pool by phagocytic cells in the reticuloendothelial system, occurring primarily in the liver and spleen leading to accumulation of contrast in those organs. In addition, in our case, targeted GNPs' liver uptake could be explain by high cathepsins' activity. However, despite the targeting of the GNPs, the maximal tumor uptake was lower than it was in the liver and spleen and comparable to kidneys accumulation only for 10 nm GNP-ABPs (FIG. 8A-8F). Previous publications showed that higher PEG concentration on the GNP surface, decreases the spleen accumulation and enhances tumor and liver uptake. Based on the chemical evaluation, it was suspected that the GNP-ABPs developed here are in low density "mushroom" configuration, hence the high spleen uptake, dominantly for 100 nm ABPs. Tumor uptake was prevalently stronger for targeted GNP-ABPs derived from ICP-MS analysis and perfectly consistent with average tumor uptake extracted from CT images (100 nm GNP-ABPs only ICP-MS data). Both 10 nm and 30 nm T-GNP showed significant higher accumulation in tumors compared to NT-GNP.

Figure 9A:
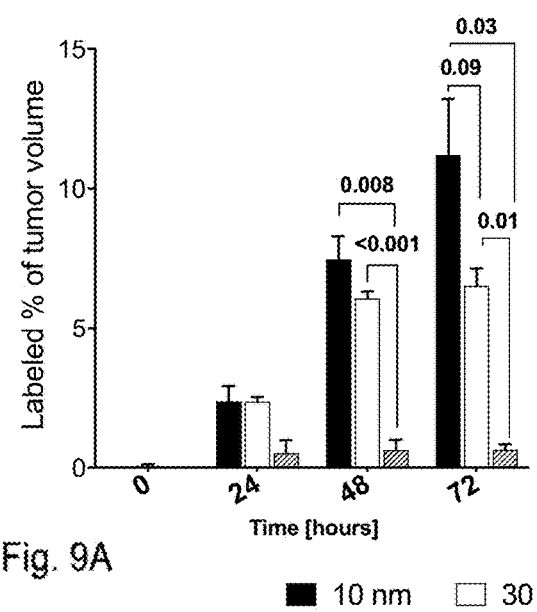
FIGS. 9A and 9B demonstrates comparison for GNP-based compounds M, revealing the strong size dependent uptake in favor of small 10 nm GNP-ABPs (T).
Figure 9B:
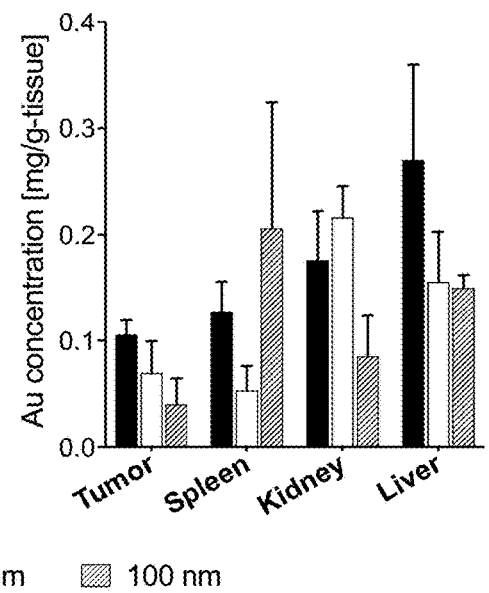

FIGS. 9A and 9B demonstrates the comparison for targeted ABPs, revealing the strong size dependent uptake in favor of small GNPs. The highest signal was detected with the 10 nm probe. The gold signal in the tumor increased over time and became highly elevated at 72 h post injection. 60 nm probe showed lower accumulation within the tumor, nevertheless both 10 and 30 nm showed significant priority compared to 100 nm probe. Furthermore, the number of voxels containing gold were reflected by ICP-MS analysis. 10 nm GNP-ABPs showed highest liver uptake, raising the necessity of better understanding of long term toxicity. One might suggest that smaller particles can't produce efficient contrast enhancement due to lower local density, however it was suggested their compensation ability by higher accumulation.

Other tumors part were taken to TEM to visualize GNP probes accumulation in biological tissue. Tumor was resected 72 h post IV injection of the probe. FIGS. 10A-10F shows that uptake of targeted CNP-ABPs by the tumor was clearly visualized for 10 nm & 30 nm proposing their accumulation in the lysosomes known in reach cathepsin activity. A small amount of non-targeted GNPs (without ABPs) was also observed due to passive uptake. For 100 nm n: difference was observed between passive and active accumulation (i.e GNP with ABP or without), possibly due to extensive spleen accumulation leading to short blood circulation hence low availability of GNP-ABPs. The images depict localization within the endosome/lysosome within the tumor cells. TEM results support one more time that the CT attenuation increase, derives from GNP-ABPs localization within the tumor cells.

Example 2: Iodine Derivatives of Activity Based Probe

General methods: Unless otherwise noted, all resins and reagents were purchased from commercial suppliers and used without further purification. Iopanoic acid was purchased from TCI, (Japan). All water-sensitive reactions were performed in anhydrous solvents under positive pressure of nitrogen or argon. Reactions were analyzed by a Liquid Chromatography Mass Spectrometer (LC-MS) (Thermo Scientific MSQ-Plus), attached to an Accela UPLC system. Unless otherwise stated, all final compounds were purified by C18 reverse phase HPLC in acetonitrile/water gradient. Proton NMR spectra were recorded on Varian Mercury 500 MHz spectrometer in deuterated solvent. Proton chemical shifts are reported in ppm ($\delta$) relative to tetramethylsilane with the solvent resonance employed as the internal standard (DMSO-d$^6$, $\delta$ 7.26 ppm). Recombinant human cathepsins B and L were prepared as described. The animal ethics committee of the Hebrew University approved all animal procedures. Male BALB/c mice (3-4 week-old) were used in all in vivo assays, 3 mice were used for each compound, repeating each experiment at least three times.

Synthesis of 2,5-dioxopyrrolidin-1-yl 2,3,5-triiodobenzoate (11): To a solution of 2,3,5-triiodobenzoic acid (0.2 mmol, 1 eq.) in anhydrous $CH_2Cl_2$ (5 mL) under argon were added N-hydroxysuccinimide (0.4 mmol, 2 eq.), DIEA (0.6 mmole, 3 eq.) and EDC-HCl (0.2 mmol, 2 eq.). The reaction mixture was stirred for 3 h at ambient temperature. DCM was added to the crude residue and the resulting organic phase was washed with water, brine and saturated $NaHCO_3$. The organic phase was dried over $MgSO_4$ and solvent was removed in vacuo. Crude product was purified by C18 reverse phase HPLC using water-acetonitrile gradient with 0.1% TFA, product was eluted with 70% acetonitrile, to obtain (11) as a white solid (0.16 mmol, 82% yield).

Synthesis of 2-(3-acetamido-2,4,6-triiodobenzyl)butanoic acid (12): To a solution of Iopanoic acid (0.88 mmol, 1 eq.) in tetrahydrofuran (10 mL) were added acetyl chloride (1.76 mmol, 2 eq.) and the solution was stirred at room temperature for 18 h. The reaction mixture was diluted with $CH_2Cl_2$, washed with water and brine. The organic phase was dried over $MgSO_4$ and solvent was removed in vacuo. The crude product (0.81 mmol, 92%) obtained was used for step without purification.

LCMS: RT 2.13 (linear gradient 5-95% of ACN/H$_2$O, 7 min), ESI-MS (m/z): 613.66 [M+H]$^+$, 635.58 [M+Na]$^+$.

Synthesis of 2,5-dioxopyrrolidin-1-yl 2-(3-acetamido-2,4,6-triiodobenzyl) butanoate (13): To a solution of 12 (0.81 mmol, 1 eq.) in anhydrous $CH_2Cl_2$ (10 mL) under argon were added N-hydroxysuccinimide (1.62 mmol, 2 eq.), DIEA (2.43 mmol, 3 eq.) and EDC-HCl (1.62 mmol, 2 eq.). The reaction mixture was stirred for 3 h at ambient temperature. $CH_2Cl_2$ was added to the crude residue and the resulting organic phase was washed with water, brine and saturated $NaHCO_3$. The organic phase was dried over $MgSO_4$ and solvent was removed in vacuo. The crude product (13) was purified by C18 reverse phase HPLC using a water-acetonitrile gradient with 0.1% TFA, the product was eluted with 60% acetonitrile, to obtain Iopanoic Acid-Succinamide Ester (IPA-SE, 13) as a white solid (0.58 mmol, 72% yield).

LCMS: RT 2.34 (linear gradient 5-95% of ACN/H$_2$O, 7 min), ESI-MS (m/z): 711.51 [M+H]$^+$, 733.50 [M+Na]$^+$.

$^1$H-NMR (300 MHz, DMSO-d$^6$): $\delta$ 9.96 (d, J=9.8 Hz, 1H, amide NH), 8.40 (s, 1H, Ar—H), 3.45 (m, 2H, CH$_2$), 3.10 (m, 1H, CH), 4.32 (m, 2H), 2.81 (s, 4H, 2XCH$_2$), 2.03 (s, 3H, CH$_3$), 1.81 (s, 1H, CH), 1.47 (m, 1H, CH), 0.93 (t, 3H, CH$_3$).

Synthesis of Iodide CT-ABP (14a-b): To a solution of GB111NH$_2$ (0.009 mmol, 1 eq.) were added iodine tag SE (0.14 mmol, eq. 1.5), DIEA (0.027, 3 eq.) in anhydrous DMSO (10 mL) and the solution was stirred at room temperature for 12 h. The reaction mixture was diluted with $CH_2C_2$ (5 mL), washed with water, brine and saturated $NaHCO_3$. The organic phase was dried over $MgSO_4$ and solvent was removed in vacuo. The crude product was purified by C18 reverse phase HPLC using a water-acetonitrile gradient with 0.1% TFA, the product was eluted with 65% acetonitrile, to obtain (14a-b) as a white solid.

14a: LCMS: RT 3.51 (linear gradient 5-95% of ACN/H$_2$O, 7 min), ESI-MS (m/z): 1057.16 [M+2]$^+$, 1079.49 [M+H+Na]$^+$.

14b: LCMS: RT 3.22 (linear gradient 5-95% of ACN/H$_2$O, 7 min), ESI-MS (m/z): 1170.63 [M+2]$^+$.

Synthesis of 5-benzyl-8-(2-((2,6-dimethylbenzoyl)oxy)acetyl)-3,6,14-trioxo-1-phenyl-2-oxa-4,7,13-triazaheptadecan-17-oic acid (15): To a solution of GB111-NH$_2$ (0.087 mmol, 1 eq.) in $CH_2Cl_2$ (5 mL) were added succinic anhydride (0.096 mmol, 1.1 eq.) and the solution was stirred at room temperature for 3 h. The reaction mixture was diluted with $CH_2Cl_2$, washed with water and brine. The organic phase was dried over $MgSO_4$ and solvent was removed in vacuo. The crude product was purified by C18 reverse phase HPLC using a water-acetonitrile gradient with 0.1% TFA, the product was eluted with 57% acetonitrile, to obtain (15) as a white solid (0.074 mmol, 85% yield).

LCMS: RT 2.69 (linear gradient 5-95% of ACN/H$_2$O, 7 min), ESI-MS (m/z): 674.93 [M+H]$^+$.

Synthesis of GB111NH$_2$-PAMAM-Go (16): To a solution of PAMAM-Go (0.3 mmol, 1.5 eq.) were added mixture of 15 (0.2 mmol, 1 eq.), PyBOP (0.4 mmol, 2 eq.), HOBt (0.4 mmol, 2 eq.) and DIEA (0.6 mmol, 3 eq.) in anhydrous DMF at 0° C. Then the reaction mixture was stirred for 12 h at ambient temperature. DCM was added to the crude residue and the resulting organic phase was washed with water, brine and saturated $NaHCO_3$. The organic phase was dried over $MgSO_4$ and solvent was removed in vacuo. The crude product was purified by C4 reverse phase HPLC using a water-acetonitrile gradient with 0.1% TFA, the product was eluted with 25% acetonitrile, to obtain (16) as a white solid (0.134 mmol, 67% yield).

LCMS: RT 1.53 (linear gradient 5-95% of ACN/H$_2$O, 7 min), ESI-MS (m/z): 1173.27 [M+H]$^+$.

Synthesis of Iodide CT-ABP (17a-b): To a solution of 16 (0.009 mmol, 1 eq.) were added iodine tag SE (0.14 nmol, 3.0 eq.), DIEA (0.027, 3 eq.) in anhydrous DMSO (2 mL) and the solution was stirred at room temperature for 12 h. The reaction mixture was diluted with $CH_2Cl_2$ (5 mL), washed with water, brine and saturated $NaHCO_3$. The organic phase was dried over $MgSO_4$ and solvent was removed in vacuo. The crude product was purified by C18 reverse phase HPLC using a water-acetonitrile gradient with 0.1% TFA, the product was eluted with 65% acetonitrile, to obtain (17a-b) as a white solid.

17a: LCMS: RT 2.80 (linear gradient 5-95% of ACN/$H_2O$, 7 min), ESI-MS (m/z): 1310.40 $[M/2+2]^+$.

17b: LCMS: RT 2.53 (linear gradient 5-95% of ACN/$H_2O$, 7 min), ESI-MS ((m/z): 1479.89 $[M/2+H]^+$.

Synthesis of Iodide CT-ABP (18): To a solution of 16 (0.009 mmol, 1 eq.) were added Iodine tag SE (13, 0.14 mmol, 1.0 eq), DIEA (0.027, 3 eq.) in anhydrous DMSO (2 mL) and the solution was stirred at room temperature for 12 h. The reaction mixture was diluted with $CH_2Cl_2$ (5 mL), washed with water, brine and saturated $NaHCO_3$. The organic phase was dried over $MgSO_4$ and solvent was removed in vacuo. The crude product was purified by C18 reverse phase HPLC using a water-acetonitrile gradient with 0.1% TFA, product was eluted with 65% acetonitrile, to obtain (18) as a white solid (0.0051 mmol, 57% yield).

LCMS: RT 12.07 (linear gradient 30-95% of ACN/$H_2O$, 20 min), ESI-MS (m/z): 1181.40 $[M+H]^+$.

Synthesis of 5-benzyl-8-(2-((2,6-dimethylbenzoyl)oxy) acetyl)-3,6,14-trioxo-1-phenyl-2-oxa-4,7,13-triazaheptadecan-17-oic acid (19): To a solution of GB111-$NH_2$ (0.087 mmol, 1 eq.) in $CH_2Cl_2$ (5 mL) were added glutaric anhydride (0.096 mmol, 1.1 eq.) and the solution was stirred at room temperature for 3 h. The reaction mixture was diluted with $CH_2Cl_2$, washed with water and brine. The organic phase was dried over $MgSO_4$ and solvent was removed in vacuo. The crude product was purified by C18 reverse phase HPLC using a water-acetonitrile gradient with 0.1% TFA, the product was eluted with 57% acetonitrile, to obtain (19) as a white solid (0.074 mmol, 95%).

LCMS: RT 2.65 (linear gradient 5-95% of ACN/$H_2O$, 7 min), ESI-MS (m/z): 688.35 $[M+H]^+$, 710.38 $[M+Na]^+$.

Synthesis of GB111NH-SE (20): To a solution of 19 (0.81 mmol, 1 eq.) in anhydrous DMF (5 mL) under argon were added N-hydroxysuccinimide (1.62 mmol, 2 eq.), DIEA (2.43 mmol, 3 eq.) and EDC-HCl (1.62 mmol, 2 eq.). The reaction mixture was stirred for 12 at ambient temperature. Ethyl acetate was added to the crude residue and the resulting organic phase was washed with water, brine and saturated $NaHCO_3$. The organic phase was dried over $MgSO_4$ and solvent was removed in vacuo. The crude product was purified by C18 reverse phase HPLC using a water-acetonitrile gradient with 0.1% TFA, product was eluted with 65% acetonitrile, to obtain (20) as a white solid (0.58 mmol, 82% yield).

LCMS: RT 2.81 (linear gradient 5-95% of ACN/$H_2O$, 7 min), ESI-MS (m/z): 785.08 $[M+H]^+$, 817.00 $[M+N]^+$.

$^1$H-NMR (300 MHz, DMSO-d$^6$): δ 8.50 (d, J=7.2 Hz, 1H, amide NH), 7.79 (s, 1H, amide NH), 7.64 (d, J=7.9 Hz, 1H, amide NH), 7.27 (m, 10H, Ar—H), 7.20 (m, 1H, Ar—H), 7.10 (d, J=15.4 Hz, 2H, Ar—H), 5.09 (d, J=10.1 Hz, 1H, CH Aomk), 4.95 (s, 2H, $CH_2$), 4.84 (m, 2H, $2XCH$), 4.32 (m, 2H), 3.00 (s, 2H, $CH_2$), 2.79 (s, 4H, $2XCH_2$), 2.64 (s, 2H, $CH_2$), 2.29 (s, 6H, $CH_3$), 2.15 (s, 2H, $CH_2$), 1.80 (s, 2H, $CH_2$), 1.54 (m, 2H, $CH_2$), 1.35 (m, 2H, $CH_2$), 1.28 (m, 2H, $CH_2$).

Synthesis of six, seven and eight iodine tagged compounds (22, 23, 24): To a solution of PAMAM G1 (0.009 mmol, 1 eq.) were added IPA-SE (13, 0.14 mmol, 4.0 eq), DIEA (0.027, 3 eq.) in anhydrous DMSO (2 mL) and the solution was stirred at room temperature for 12 h. The reaction mixture was purified by C18 reverse phase HPLC using a water-acetonitrile gradient with 0.1% TFA, product was eluted with 45% acetonitrile, to obtain six, seven and eight iodine tagged products (22, 23, 24 respectively) as a white solid (12, 9, 22% yields receptively).

22: LCMS: RT 2.71 (linear gradient 5-95% of ACN/$H_2O$, 10 min), ESI-MS (m/z): 1250.91 $[M/4+H]^+$, 1000.89 $[M/5+H]^+$.

23: LCMS: RT 2.80 (linear gradient 5-95% of ACN/$H_2O$, 10 min), ESI-MS (m/z): 1399.56 $[M/4+H]^+$.

24: LCMS: RT 2.90 (linear gradient 5-95% of ACN/$H_2O$, 7 min), ESI-MS (m/z): 1548.08 $[M/4+H]^+$.

Synthesis of six iodine tagged probe HG81 (25): To a solution of 22 (0.009 mmol, 1 eq.) were added GB111NH-SE (20, 0.14 mmol, 1.0 eq), DIEA (0.027, 3 eq.) in anhydrous DMSO (2 mL) and the solution was stirred at room temperature for 12 h. The reaction mixture was purified by C18 reverse phase HPLC using a water-acetonitrile gradient with 0.1% TFA, the product was eluted with 41% acetonitrile, to obtain HG81 (25) and HG81a (26) as a white solid.

HG81 (25): LCMS: RT 3.27 (linear gradient 5-95% of ACN/$H_2O$, 10 min), ESI-MS (m/z): 1885.76 $[M/3+H]^+$, 414.71 $[M/4+H]^+$.

HG81a (26): LCMS: RT 3.82 (linear gradient 5-95% of ACN/$H_2O$, 10 min), ESI-MS (m/z): 1578.45$[M/4+H]^+$.

Synthesis of seven iodine tagged probe, HG78 (27): To a solution of 23 (0.009 mmol, 1 eq.) were added GB111NH-SE (20, 0.14 mmol, 1.0 eq), DIEA (0.027, 3 eq.) in anhydrous DMSO (2 mL) and the solution was stirred at room temperature for 12 h. The reaction mixture was purified by C18 reverse phase HPLC using a water-acetonitrile gradient with 0.1% TFA, the product was eluted with 47% acetonitrile, to obtain HG78 (27) as a white solid (0.0074 mmol, 81% yield).

LCMS: RT 3.53 (linear gradient 5-95% of ACN/$H_2O$, 10 min), ESI-MS (m/z): 1563.72 $[M/3+H]^+$.

Synthesis of Cy5 labeled I-CT-ABP, HG92 (28): To a solution of above, six iodine tagged activity based probe (25, 0.009 mmol, 1 eq.) were added Cy5-NHS ester (0.14 mmol, 1.0 eq), DIEA (0.227, 3 eq.) in anhydrous DMSO (2 mL) and the reaction mixture was stirred at room temperature for 12 h. The reaction mixture was purified by C18 reverse phase HPLC using a water-acetonitrile gradient with 0.1% TFA, the product was eluted with 45% acetonitrile, to obtain HG92 (28) as a blue solid (0.007 mmol, 78% yield).

LCMS: RT 3.14 (linear gradient 5-95% of ACN/$H_2O$, 10 min), ESI-MS (m/z): 1577.83 $[M/4+H]^+$.

Synthesis of Cy5 labeled control I-CT-ABP, HG31 (29): To a solution of 23 (0.009 mmol, 1 eq.) were added Cy5-NHS ester (0.14 mmol, 1.0 eq), DIEA (0.027, 3 eq.) in anhydrous DMSO (2 mL) and the solution was stirred at room temperature for 12 h. The reaction mixture was purified by C18 reverse phase HPLC using a water-acetonitrile gradient with 0.1% TFA, the product was eluted with 51% acetonitrile, to obtain (29) as a blue solid (0.0077 mmol, 86% yield).

LCMS: RT 2.92 (linear gradient 5-95% of ACN/$H_2O$, 10 min), ESI-MS (m/z): 1558.83 $[M/4+H]^+$, 1247.25 $[M/5+H]^+$.

Synthesis of PAMAM-G3 conjugated nanometric probes (I-CT-ABP): To a solution of G3 PAMAM dendrimers (($NH_2$)$_{32}$-G3; PAMMA-G3; 100 mg; 0.014 mmol) DIEA (0.46 mmol, 32 eq.) in anhydrous DMSO (3 mL) was added IPA-SE (13, 0.23 mmol, 16.0 eq) and the mixture was stirred at room temperature for 12 h. The resulting mixture was first purified by 8 kD dialysis against Methanol and DI water for 3 runs each and then lyophilized to yield $(IPA)_{16}(NH_2)_{16}$-G3 (30) as a sticky white solid (211 mg; 88%). To the resulting conjugate, $(IPA)_{16}(NH_2)_{16}$-G3 (30, 200 mg, 0.0122 mmol, 1.0 eq)), was added GB111NH-SE (20, 0.0122 mmol, 1.0 eq), DIEA (0.39 mmol, 32 eq) in anhydrous DMSO (2 mL) and the mixture was stirred at room temperature for 2 h. The mixture was then purified by 8 kD dialysis against Methanol and DI water for 3 runs each and then lyophilized to yield $(IPA)_{16}(NH_2)_{15}(GB)_1$-G3 (31) as a sticky white solid (190 mg; 91%). To the protease activated conjugate, $(IPA)_{16}(NH_2)_{15}(GB)_1$-G3 (31, 20 mg, 0.0012 mmol, 1.0 eq), was added acetic anhydride (0.037 mmol, 32 eq), DIEA (0.075 mmol, 64 eq.) in anhydrous DMSO (2 mL) and the mixture was stirred at room temperature for 12 h. The mixture was then purified by 8 kD dialysis against Methanol and DI water for 3 runs each and then lyophilized to yield $(IPA)_{16}(GB)_1(Ac)_{15}$-G3 (32) as a brown solid (19 mg; 91%). To the protease activated conjugate, $(IPA)_{16}(NH_2)_{15}(GB)_1$-G3 (31, 20 mg, 0.0012 mmol, 1.0 eq), was added PEG(4) and PEG750 NHS ester (0.037 mmol, 32 eq), DIEA (0.075 mmol, 64 eq.) in anhydrous DMSO (2 mL) separately and the mixture was stirred at room temperature for 12 h. The each reaction mixture was then purified by 8 kD dialysis against Methanol and DI water for 3 runs each and then lyophilized to yield $(IPA)_{16}(GB)_1(PEG-4)_{15}$-G3 (33) as a white solid (20 mg; 83.9%) and $(IPA)_{16}(GB)_1(PEG-750)_{15}$-G3 (34) as a white solid (28 mg; 89.9%). A negative controls, G3 dendrimers without GB111 synthesis: To the free amine conjugate, $(IPA)_{16}(NH_2)_{16}$-G3 (30, 20 mg, 0.0012 mmol, 1.0 eq), was added acetic anhydride (0.039 mmol, 32 eq), DIEA (0.078 mmol, 64 eq.) in anhydrous DMSO (2 mL) and the mixture was stirred at room temperature for 12 h. The mixture was then purified by 8 kD dialysis against Methanol and DI water for 3 runs each and then lyophilized to yield $(IPA)_{16}(Ac)_{16}$-G3 (35) as a brown solid (18 mg; 86.3%). To the free amine conjugate, $(IPA)_{16}(NH_2)_{16}$-G3 (30, 20 mg, 0.0012 mmol, 1.0 eq), was added PEG(4) and PEG750 NHS ester (0.039 mmol, 32 eq), DIEA (0.078 mmol, 64 eq.) in anhydrous DMSO (2 mL) separately and the mixture was stirred at room temperature for 12 h. The mixture was then purified by 8 kD dialysis against Methanol and DI water for 3 runs each and then lyophilized to yield $(IPA)_{16}(PEG-4)_{16}$-G3 (36) as a white solid (21 mg; 86.6%) and $(IPA)_{16}(PEG-750)_{16}$-G3 (37) as a white solid (29 mg; 89.5%). The number of conjugated IPA molecules per dendrimer was determined to be 16, on average using $^1$H-NMR spectroscopy. The characteristic peaks at δ (ppm) 7-8 belong to the phenyl proton (16 H's) of the aromatic ring of IPA. The number of conjugated GB111 molecules per dendrimer was determined to be one, on average, using 1H-NMR spectroscopy. The characteristic peaks at δ (ppm) 7-8 belong to the dimethyl proton (6 H's) of the aromatic ring of GB111. The number of conjugated Acetyl, PEG(4) and PEG-750 per dendrimer was determined to be on average, using $^1$H-NMR spectroscopy.

HG87 (30): $^1$H-NMR (500 MHz, DMSO-$d_6$): δ 9.89 (bs, 16H, amide NH), 8.31 (s, 16H, Ar—H), δ 7.94-7.70 (brs, 60H, amide protons), 3.23-2.91 (bs, ~120H), 2.71-2.53 (bs, ~184H), 2.42-2.29 (brs, ~58H), 2.23-2.07 (bs, ~120H), 2.03 (s, 48H, CH$_3$), 1.61 (m, 16H, CH), 1.30 (m, 16H, CH), 0.71 (t, 48H, CH$_3$).

HG82 (31): $^1$H-NMR (500 MHz, DMSO-$d_6$): δ 9.93 (bs, 16H, amide NH), 8.35 (s, 16H, Ar—H), δ 7.96-7.76 (brs, 60H, amide protons), 7.34-7.23 (m, 10H, Ar—H), 7.23-7.16 (m, 3H, Ar—H), 7.13-7.07 (m, 3H, Ar—H), 5.78 (m, 2H, CH$_2$), 3.53-2.96 (bs, ~120H), 2.71-2.53 (brs, ~184H), 2.46-2.33 (m, ~58H), 2.31 (s, 8H, CH$_3$), 2.26-2.07 (bs, ~120H), 2.02 (s, 48H, CH$_3$), 1.87 (s, 2H, CH$_2$), 1.68 (m, 16H, CH), 1.54 (m, 2H, CH$_2$), 1.35 (m, 16H, CH), 1.21 (m, 2H, CH$_2$), 0.71 (t, 48H, CH$_3$).

HG86 (32): $^1$H-NMR (500 MHz, DMSO-$d_6$): δ 9.91 (bs, 16H, amide NH), 8.34 (s, 16H, Ar—H), 8.01-7.71 (m, 60H, amide protons), 7.33-7.24 (m, 13H, Ar—H), 7.21-7.17 (m, 3H, Ar—H), 7.11-7.07 ((m, 3H, Ar—H), 4.96 (m, 2H, CH$_2$), 3.25-3.15 (m, ~120H), 3.14-2.99 (brs, ~154H), 2.76-2.53 (m, ~120H), 2.46-2.33 (m, ~58H), 2.30 (s, 9H, CH$_3$), 2.27-2.10 (brs, ~120H), 2.01 (s, 48H, COCH$_3$), 1.79 (s, 42H, COCH$_3$), 1.90 (s, 4H, CH$_2$), 1.66 (m, 16H, CH), 1.52 (m, 4H, CH$_2$), 1.34 (m, 16H, CH), 1.24 (m, 2H, CH$_2$), 0.74 (t, 48H, CH$_3$).

HG95 (33): $^1$H-NMR (500 MHz, DMSO-$d_6$): δ 9.92 (bs, 16H, amide NH), 8.35 (s, 16H, Ar—H), 5 7.95-7.76 (brs, 60H, amide protons), 7.33-7.23 (m, 15H, Ar—H), 7.22-7.18 (m, 4H, Ar—H), 7.12-7.08 (m, 4H, Ar—H), 4.97 (brs, 2H, CH$_2$), 3.52-3.44 (brs, 20H), 3.25-3.15 (brs, 50H), 3.14-2.99 (bs, 120H), 2.72-2.59 (brs, ~108H), 2.45-2.34 (brs, ~58H), 2.33-2.27 (brs, ~40H), 2.26-2.11 (brs, ~120H), 2.01 (s, 48H, CH$_3$), 1.66 (m, 16H, CH), 1.53 (m, 2H, CH$_2$), 1.33 (m, 16H, CH), 1.23 (m, 2H, CH$_2$), 0.75 (t, 48H, CH$_3$).

HG96 (34): $^1$H-NMR (500 MHz, DMSO-$d_6$): δ 9.93 (bs, 16H, amide NH), 8.35 (s, 16H, Ar—H), δ 7.95-7.81 (brs, 60H, amide protons), 7.34-7.24 (m, 16H, Ar—H), 7.22-7.18 (m, 4H, Ar—H), 7.11-7.08 (m, 4H, Ar—H), 4.97 (bs, 2H, CH$_2$), 3.57-3.46 (bs, ~500H), 3.27-3.43 (m, ~400H), 3.25-3.15 (brs, 120H), 3.14-3.01 (brs, ~120H), 2.42-2.35 (brs, ~58H), 2.33-2.27 (brs, ~40H), 2.34-2.19 (brs, ~120H), 2.02 (s, 48H, CH$_3$), 1.66 (m, 16H, CH), 1.54 (m, 2H, CH$_2$), 1.34 (m, 16H, CH), 1.23 (m, 2H, CH$_2$), 0.75 (t, 48H, CH$_3$).

HG33 (35): $^1$H-NMR (500 MHz, DMSO-$d_6$): δ 9.89 (bs, 16H, amide NH), 8.31 (s, 16H, Ar—H), 8.03-7.72 (m, 60H, amide protons), 7.10-7.06 (m, 3H, Ar—H), 3.23-3.16 (m, ~120H), 3.13-2.98 (brs, ~154H), 2.77-2.52 (m, ~120H), 2.47-2.32 (m, ~58H), 2.26-2.11 (brs, ~120H), 2.01 (s, 48H, COCH$_3$), 1.78 (s, 42H, COCH$_3$), 1.64 (m, 16H, CH), 1.32 (m, 16H, CH), 0.75 (t, 48H, CH$_3$).

HG94 (36): $^1$H-NMR (500 MHz, DMSO-$d_6$): δ 9.95 (brs, 16H, amide NH), 8.36 (s, 16H, Ar—H), δ 7.94-7.70 (brs, 60H, amide protons), 3.52-3.46 (brs, ~160H), 3.23-2.91 (brs, ~120H), 2.71-2.53 (brs, ~184H), 2.42-2.29 (brs, ~58H), 2.23-2.07 (brs, ~120H), 2.02 (s, 48H, CH$_3$), 1.68 (m, 16H, CH), 1.35 (m, 16H, CH), 0.75 (t, 48H, CH$_3$).

HG97 (37): $^1$H-NMR (500 MHz, DMSO-$d_6$): δ 9.91 (bs, 16H, amide NH), 8.34 (s, 16H, Ar—H), δ 7.96-7.80 (brs, 60H, amide protons), 3.59-3.45 (bs, ~500H), 3.42-3.25 (m, ~400H), 3.23-3.14 (brs, 120H), 3.12-2.98 (brs, ~120H), 2.41-2.33 (brs, ~58H), 2.31-2.18 (brs, ~120H), 2.01 (s, 48H, CH3), 1.67 (m, 16H, CH), 1.33 (m, 16H, CH), 0.73 (t, 48H, CH3).

Synthesis of Cy5 labelled PAMAM-G3 conjugated I-CT-ABP: To the protease activated conjugate, $(IPA)_{16}(NH_2)_{15}(GB)_1$-G3 (31, 30 mg, 0.0017 mmol, 1.0 eq), was added Cy5-NHS ester (0.0017 mmol, 1.0 eq), DIEA (0.112 mmol, 64 eq.) in anhydrous DMSO (2 mL) and the mixture was stirred at room temperature for 2 h, then acetic anhydride (0.056 mmol, 32 eq), was added to the reaction mixture and stirred at room temperature for 12 h. The reaction mixture was then purified by 8 kD dialysis against methanol and DI water for 3 runs each and then lyophilized to yield $(IPA)_{16}(GB)_1(Cy5)_1(Ac)_{14}$-G3 (38) as a blue solid (25 mg; 78.1%). To the protease activated conjugate, $(IPA)_{16}(NH_2)_{15}(GB)_1$-

G3 (31, 20 mg, 0.0012 mmol, 1.0 eq), was added Cy5-NHS ester (0.0012 mmol, 1.0 eq), DIEA (0.075 mmol, 64 eq.) in anhydrous DMSO (2 mL) and the mixture was stirred at room temperature for 2 h, and then PEG750 NHS ester (0.037 mmol, 32 eq), was added to the reaction mixture and stirred at room temperature for 12 h. The mixture was then purified by 8 kD dialysis against methanol and DI water for 3 runs each and then lyophilized to yield $(IPA)_{16}(GB)_1(Cy5)_1(PEG-750)_{14}$-G3 (39) as a blue solid (27 mg; 86.8%). A negative controls, G3 dendrimers without GB111 synthesis: To the free amine conjugate, $(IPA)_{16}(NH_2)_{16}$-G3 (30, 20 mg, 0.0012 mmol, 1.0 eq), was added Cy5-NHS ester (0.0012 mmol, 1.0 eq), DIEA (0.078 mmol, 64 eq.) in anhydrous DMSO (2 mL) and the mixture was stirred at room temperature for 2 h, then acetic anhydride (0.039 mmol, 32 eq), was added to the reaction mixture and stirred at room temperature for 12 h. The reaction mixture was then purified by 8 kD dialysis against methanol and DI water for 3 runs each and then lyophilized to yield $(IPA)_{16}(Cy5)_1(Ac)_{15}$-G3 (40) as a blue solid 19 mg; 89.3%). To the free amine conjugate, $(IPA)_{16}(NH_2)_{16}$-G3' 30, 20 mg, 0.0012 mmol, 1.0 eq), was added Cy5-NHS ester (0.0012 mmol, 1.0 eq), DIEA (0.078 mmol, 64 eq.) in anhydrous DMSO (2 mL) and the mixture was stirred at room temperature for 2 h and then PEG750 NHS ester (0.039 mmol, 32 eq), was added to the reaction mixture and stirred at room temperature for 12 h. The mixture was then purified by 8 kD dialysis against methanol and DI water for 3 runs each and then lyophilized to yield $(IPA)_{16}(Cy5)_1(PEG-750)_{15}$-G3 (41) as a blue solid (26 mg; 83.3%). The number of conjugated IPA molecules per dendrimer was determined to be 16, on average using 1H-NMR spectroscopy. The characteristic peaks at δ (ppm) 8.1 belong to the phenyl proton (16 H's) of the aromatic ring of IPA. The number of conjugated GB111 molecules per dendrimer was determined to be one, on average, using $^1$H-NMR spectroscopy. The characteristic peaks at δ (ppm) 7-8 belong to the dimethyl proton (6 H's) of the aromatic ring of GB111. The number of conjugated Cy5 dyes per dendrimer was determined to be 1, on average, using spectrophotometry. The number of conjugated Acetyl and PEG-750 per dendrimer was determined to be on average, using 1H-NMR spectroscopy.

HG90 (38): $^1$H-NMR (500 MHz, DMSO-d$_6$): δ 9.93 (bs, 16H, amide NH), 9.86 (m, 6H, cy5H), 9.43 (m, 9H, cy5H), 9.33 (m, 3H, cy5H), 8.35 (s, 16H, Ar—H), 8.24 (m, 4H, cy5H), δ 7.95-7.76 (brs, cOH, amide protons), 7.65 (m, 8H, cy5H), 7.34-7.24 (m, 14H, Ar—H), 7.22-7.18 (m, 3H, Ar—H), 7.11-7.08 (m, 3H, Ar—H), 6.97 (m, 5H, cy5H), 6.79 (m, 9H, cy5H), 6.31 (m, 8H, cy5H), 4.97 (brs, 2H, CH$_2$), 4.33 (m, 12H, cy5H), 3.26-3.15 (bs, ~60H), 3.24 (brs, ~60H), 3.14-3.09 (brs, ~120H), 2.74-2.56 (brs, ~120H), 2.46-2.35 (brs, ~60H), 2.30 (s, 20H), 2.26-2.13 (brs, ~120H), 2.02 (s, 48H, CH$_3$), 1.97 (s, 4H), 1.80 (s, 45H, CH$_3$), 1.69 (m, 16H, CH), 1.54 (m, 2H, CH$_2$), 1.34 (m, 16H, CH), 1.24 (m, 2H, CH$_2$), 1.14 (s, ~20H), 0.75 (t, 48H, CH$_3$).

HG93 (39): $^1$H-NMR (500 MHz, DMSO-d$_6$): δ 9.93 (bs, 16H, amide NH), 9.85 (m, 6H, cy5H), 9.46 (m, 9H, cy5H), 9.34 (m, 3H, cy5H), 8.35 (s, 16H, Ar—H), δ 7.95-7.76 (brs, 60H, amide protons), 7.34-7.24 ((m, 14H, Ar—H), 7.22-7.18 (m, 3H, Ar—H), 7.11-7.08 (m, 3H, Ar—H), 6.95 (m, 5H, cy5H), 6.80 (m, 9H, cy5H), 6.33 (m, 8H, cy5H), 4.97 (brs, 2H, CH$_2$), 3.57-3.46 (bs, ~400H), 3.24 (brs, ~60H), 3.20-3.16 (brs, 120H), 3.14-3.01 (brs, ~120H), 2.64 (brs, ~50H), 2.33-2.27 (brs, ~58H), 2.34-2.19 (brs, ~120H), 2.02 (s, 48H, CH$_3$), 1.68 (m, 16H, CH, 1.54 (m, 2H, CH$_2$), 1.34 (m, 16H, CH), 1.24 (m, 2H, CH$_2$), 1.14 (s, ~20H), 0.75 (t, 40H, CH$_3$).

HG9 (40): $^1$H-NMR (500 MHz, DMSO-d6): δ 9.91 (bs, 16H, amide NH), 9.86 (m, 6H, cy5H), 9.41 (m, 9H, cy5H), 8.34 (s, 16H, Ar—H), 8.21 (m, 4H, cy5H), δ 7.93-7.75 (brs, 60H, amide protons), 6.96 (m, 5H, cy5H), 6.77 (m, 9H, cy5H), 6.30 (m, 8H, cy5H), 4.31 (m, 12H, cy5H), 3.29-3.13 (bs, ~60H), 3.21 (brs, ~60H), 3.13-3.07 (brs, ~120H), 2.73-2.55 (brs, ~120H), 2.47-2.36 (brs, ~60H), 2.27-2.11 (brs, ~120H), 2.03 (s, 48H, CH3), 1.79 (s, 45H, CH3), 1.67 (m, 16H, CH), 1.35 (m, 16H, CH), 1.13 (s, ~20H), 0.73 (t, 48H, CH3).

HG32 (41): $^1$H-NMR (500 MHz, DMSO-d6): δ 9.94 (bs, 16H, amide NH), 9.86 (m, 6H, cy5H), 9.43 (m, 9H, cy5H), 9.35 (m, 3H, cy5H), 8.33 (s, 16H, Ar—H), δ 7.96-7.75 (brs, 60H, amide protons), 6.93 (m, 5H, cy5H), 6.83 (m, 9H, cy5H), 6.31 (m, 8H, cy5H), 3.56-3.41 (bs, ~400H), 3.21 (brs, ~60H), 3.19-3.16 (brs, 120H), 3.13-3.02 (brs, ~120H), 2.63 (brs, ~50H), 2.32-2.26 (brs, ~58H), 2.33-2.19 (brs, ~120H), 2.01 (s, 48H, CH$_3$), 1.67 (m, 16H, CH), 1.35 (m, 16H, CH), 1.13 (s, ~20H), 0.73 (t, 48H, CH$_3$).

Recombinant cathepsin labeling, competition assay: Recombinant human Cathepsin L (0.5 μg), Cathepsin B (0.5 μg) were incubated the indicated concentrations of targeted or control iodinated activity based probes (CT-ABP) in reaction buffer (50 mM acetate, 2 mM DTT and 5 mM MgCl$_2$, pH 5.5) for 120 minutes at 37° C. After probe incubation, residual cathepsin activity was labeled with GB123 for 30 minutes. The reaction was stopped by addition of sample buffer ×4 (40% glycerol, 0.2 M Tris/HCl, pH 6.8, 20% beta-mercaptoethanol, 12% SDS and 0.4 mg/ml bromophenol blue). Samples were then boiled, separated on a 12.5% SDS gel and scanned for fluorescence by a Typhoon scanner FLA 9500 at excitation/emission wavelengths of 645/670 nm.

Recombinant cathepsin direct labeling: Recombinant human Cathepsin L (0.5 μg), Cathepsin B (0.5 μg) were incubated the indicated concentrations of targeted or control Cy5 labelled iodinated activity based probes (CT-ABP) in reaction buffer (50 mM acetate, 2 mM DTT and 5 mM MgCl$_2$, pH 5.5) for 120 minutes at 37° C. The reaction was stopped by addition of sample buffer ×4 (40% glycerol, 0.2 M Tris/HCl, pH 6.8, 20% beta-mercaptoethanol, 12% SDS and 0.4 mg/mi bromophenol blue). Samples were then boiled, separated on a 12.5% SDS gel and scanned for fluorescence by a Typhoon scanner FLA 9500 at excitation/emission wavelengths of 645/670 nm.

Cell cultures: NIH-3T3 mouse fibroblast cells, Raw 264.7 mouse macrophage cells or 4T1 murine mammary gland epithelial cells were cultured in DMEM (Dulbecco's modified eagle's medium) supplemented with 10% fetal bovine serum (FBS), 1% penicillin and 1% streptomycin. Experiments were performed on either day 6 or day 7 after plating in culture. All cells were cultured in a humidified atmosphere of 95% air and 5% CO$_2$ at 37° C.

Evaluation of probes permeability to intact cells, competition assay: NIH-3T3 cells ($100 \times 10^3$ cells/well) were seeded in a twelve-well plate one day before treatment. Cells were treated with indicated concentrations of targeted or control iodinated activity based probes (CT-ABP) that were pre-dissolved in 0.1% DMSO in the culture medium. After 24 hours of probe incubation, residual cathepsin activity was labelled with GB123 (1 μM)(final DMSO concentration was maintained at 0.2%). Cells were washed with PBS and lysed by addition of sample buffer. Lysates were boiled for 5 minutes, centrifuged, and separated by 12.5% SDS-PAGE. Residual labelled proteases in cells were visualized by scanning the gel fluorescence by a Typhoon scanner FLA 9500 at excitation/emission wavelengths of 645/670 nm.

Evaluation of probes permeability to intact cells, direct labelling assay: NIH-3T3 mouse fibroblast cells (100×10³ cells/well) were seeded in a twelve-well plate one day before treatment. Cells were treated with indicated concentrations of targeted or control Cy5 labelled iodinated activity based probes (I-CT-ABP) that were pre-dissolved in 0.1% DMSO in culture medium for 24 hours. Cells were then washed with PBS and lysed by addition of sample buffer. Lysates were boiled for 5 minutes and centrifuged. 100 µg proteins of NIH-3T3 cell lysates or 150 µg of 4T1 cell lysates were then separated by 12.5% SDS-PAGE. Labelled proteases in cells were visualized by scanning the gel fluorescence by a Typhoon scanner FLA 9500 at excitation/emission wavelengths of 645/670 nm.

In vitro Cytotoxicity Assays. Methylene Blue assays were performed in 96-well plates; NIH-3T3 cells (5×10³ cells/well) were seeded in a 96-well plate one day before treatment. Cells were treated with indicated concentrations of targeted IABNs and non-targeted nanomaterials that were pre-dissolved in 0.1% DMSO in the culture medium. Cells were incubated for 24 h and 48 h and cells were fixed with 2.5% glutaraldehyde incubation for 10 min. Cells were washed with water and borate buffer (0.1M, pH=8.5), Cell number was determined by staining cells with the addition of 100 µl per well of 1% Methylene Blue in borate buffer, followed by incubation at room temperature for at least 1 hour. The stain was aspirated and the plates rinsed by immersion in water, followed by immersion in deionized water. The plates were air-dried and then the stain was released from cells by the addition of 200 µl/well 0.1 N HCl solutions. After 1 hour incubation at 37° C., the absorbance of each 11 at 620 nm was determined on a Cytation 3 microplate reader.

In vivo imaging: 4T1 cells were grown to subconfluency, followed by detachment with trypsin, spin down and resuspension in 0.5% BSA in sterile PBS and 25% matrigel. Cells (1×106 per spot in a total volume of 20 µl) were injected subcutaneously at the indicated locations into 3-4 week-old male BALB/c mice under isoflurane anaesthesia. Tumors were typically established 9-11 days after cells injections, the fur was removed from mice and 100 µl of a 0.5 mg/mice solution of targeted or control Cy5 labelled iodinated activity based probes (CT-ABP) were injected intravenously via the tail vein. Mice anesthetized with isoflurane were then imaged at indicated time points after probe injection using the IVIS kinetic equipped with a 645/670 nm excitation/emission filter.

In vivo imaging of Iodine tagged CT-ABP: in vivo studies were initiated by investigating the probes pharmacokinetics in tumor-bearing mice. This was done to establish the non-invasive imaging capabilities of iodinated activity based probes. 4T1 cells were grown to sub-confluency, followed by detachment with trypsin, and resuspension in 0.5% BSA in sterile PBS and 25% matrigel. Cells (9×105 per spot in a total volume of 20 µl) were injected subcutaneously on the back of 3-4 week-old male BALB/c mice under isoflurane-anesthesia. Tumors were established 9-11 days after cells injections. A solution of targeted I-CT-ABP and control contrast agent were injected intravenously via the tail vein as follows: HG90 or HG99 (exp1), HG92 or HG31 (exp2) dissolved in 10% DMSO in PBS in a total volume of 100 µl of a iodine concentration 0.5 mg/mice. Mice anesthetized with isoflurane were imaged before, at 5 and 24 hours post injection. Micro-CT scanner (Skyscan High Resolution Model 1176) equipped with 64 detectors with a nominal resolution of 35 µm was used. For exp1, the following were used 0.2 mm aluminum filter, a tube voltage of 40 kV and 500 mA, for exp2 the following were used 0.5 mm aluminum filter, 60 kV and 350 mA. Reconstruction was performed using SkyScanNRecon software. Ring artifact reduction, Gaussian smoothing (3%), and beam hardening correction (25%) were applied in both experiments. Volume rendered three-dimensional (3D) images were generated using SkyScan CT-Volume ("CTVol") software.

Evaluation of the probe's ability to induce apoptosis in vivo after PDT: BALB/c mice bearing two tumor spots of 4T1 cells (see above for details) were injected via the tail vein with Iodine tagged probes (as described above). After 24 hours, post targeted or control Iodine tagged probes injection, mice were anesthetized with isoflurane and sacrificed by cervical dislocation. Tumors, liver, kidneys, and spleen were surgically excised and imaged ex vivo using the same IVIS kinetic as above; fluorescence intensity was calculated by dividing fluorescence signal intensity by area. Tissues were either frozen in liquid nitrogen and lysed using bead beater or bounced in RIPA buffer. Proteins were quantified by Bradford assay; total protein extracts (100 µg) were separated by 12.5% SDS-PAGE and visualized by scanning the gel with a Typhoon scanner FLA 9500 at excitation/emission wavelengths of 645/670 NM, or tumors was incubated for 4 hours with 4% paraformaldehyde, followed by an overnight incubation with 30% sucrose at 4° C. Samples were then embedded in OCT and frozen at −80° C. Tissue was sectioned into 10 µm thick slices using a CM 1900 cryotome (Leica Microsystems, Wetzlar, Germany). The samples were mounted with DAPI Fluoromount-G (Southern Biotech, AL, USA). Fluorescent pictures were taker, with an Olympus FV10i confocal microscope (Olympus, Tokyo, Japan) equipped with Cy5 and DAPI filters.

Results

Iopanoic acid (IPA) and 2,3,5-triiodobenzoic acid (TBA) used as an Iodine tag and linker as an ethylenediamine core PAMAM dendrimer, which may have requisite hydrophilic interaction for good physiological aqueous solubility, which will clear very quickly from bloodstream after intravenous inoculation. Iodide tag were synthesized starting from commercially available 2,3,5-triiodobenzoic acid and Iopanoic acid. The Succinamide Ester (SE) of 2,3,5-triiodobenzoic acid and acetylated Iopanoic acid generated by using N-hydroxysuccinamide and N-(3-Dimethylaminopropyl)-N'-ethylcarbodiimide (EDC) in basic conditions (Scheme 2). Iodine tagged Computed Tomography-Activity Based Probe (I-CT-ABP) (14a-b) were synthesized by reaction of 3 with SE of iodide tag in basic conditions. Two and three tagged Iodide CT-ABP (17a-b) were synthesized starting from 3, which on reaction with succinic anhydride followed by coupling with ethylenediamie core PAMAM-G0 and then reaction with SE of iodide tag in basic conditions (Scheme 3). Further IPA was chosen as an iodine tag for the synthesis of multiple tagged I-CT-ABP because it has good hydrophilic properties and high cell permeability. Six rid seven tagged Iodide CT-ABP (25, 26, 27) were synthesized starting from ethylenediamie core PAMAM-G1 reaction with SE of iodide tag in basic conditions to give six, seven and eight tagged compounds (22, 23, 24), which on reaction with GB111NH-SE in basic conditions to give 25, 26, 27 (Scheme 4).

Scheme 2
Synthesis of iodine tag Succinamide Ester (SE).
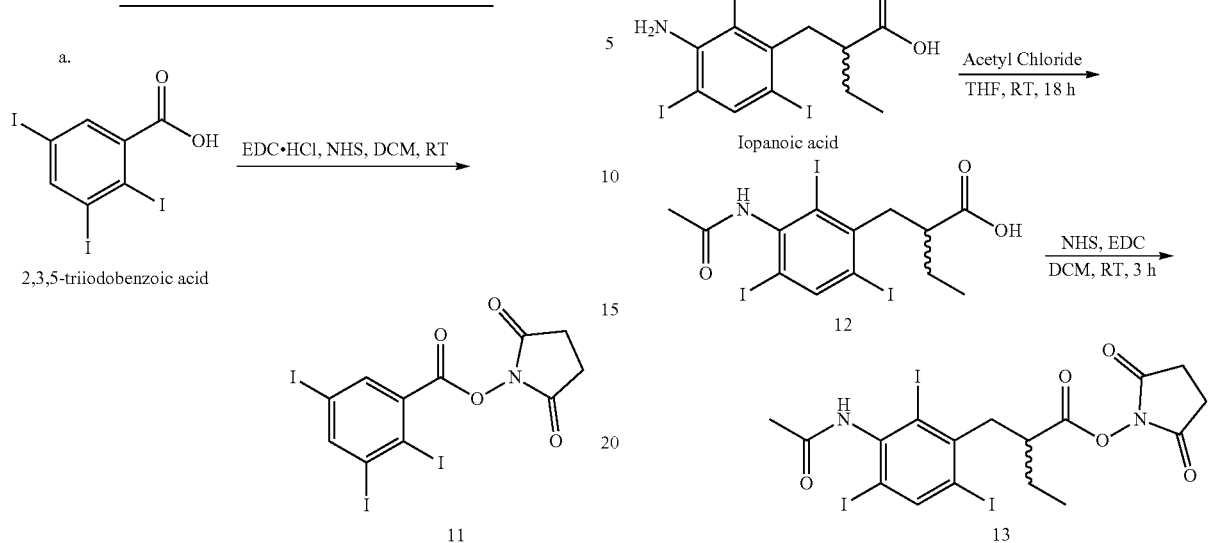
Scheme 3
Synthesis of iodine tagged activity based probe (CT-ABP), single tag
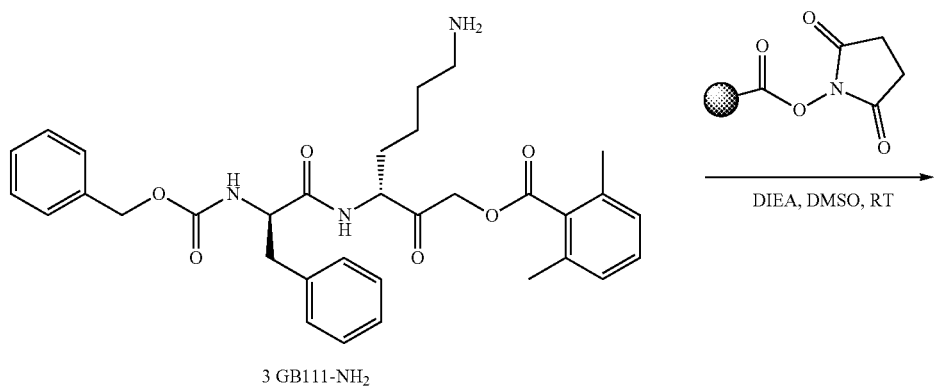
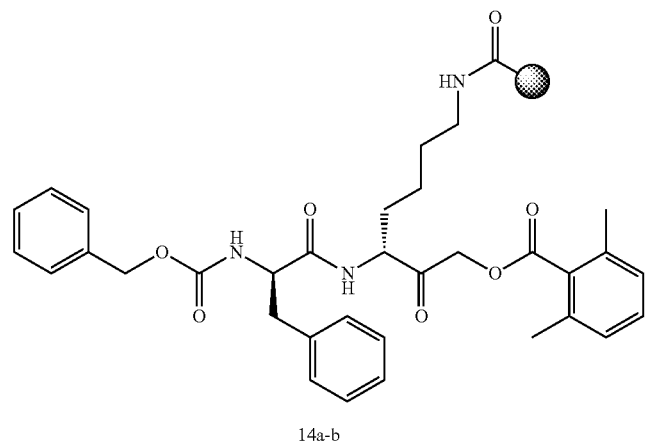

Where:
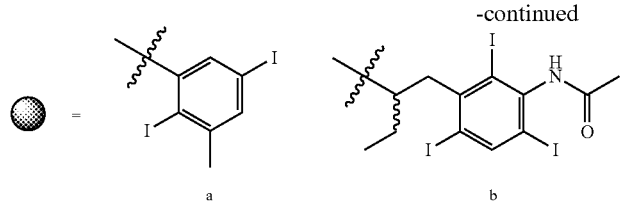
Synthesis of iodine tagged activity based probe (CT-ABP). Synthesis of Iodine CT-ABP (three tagged).
b.
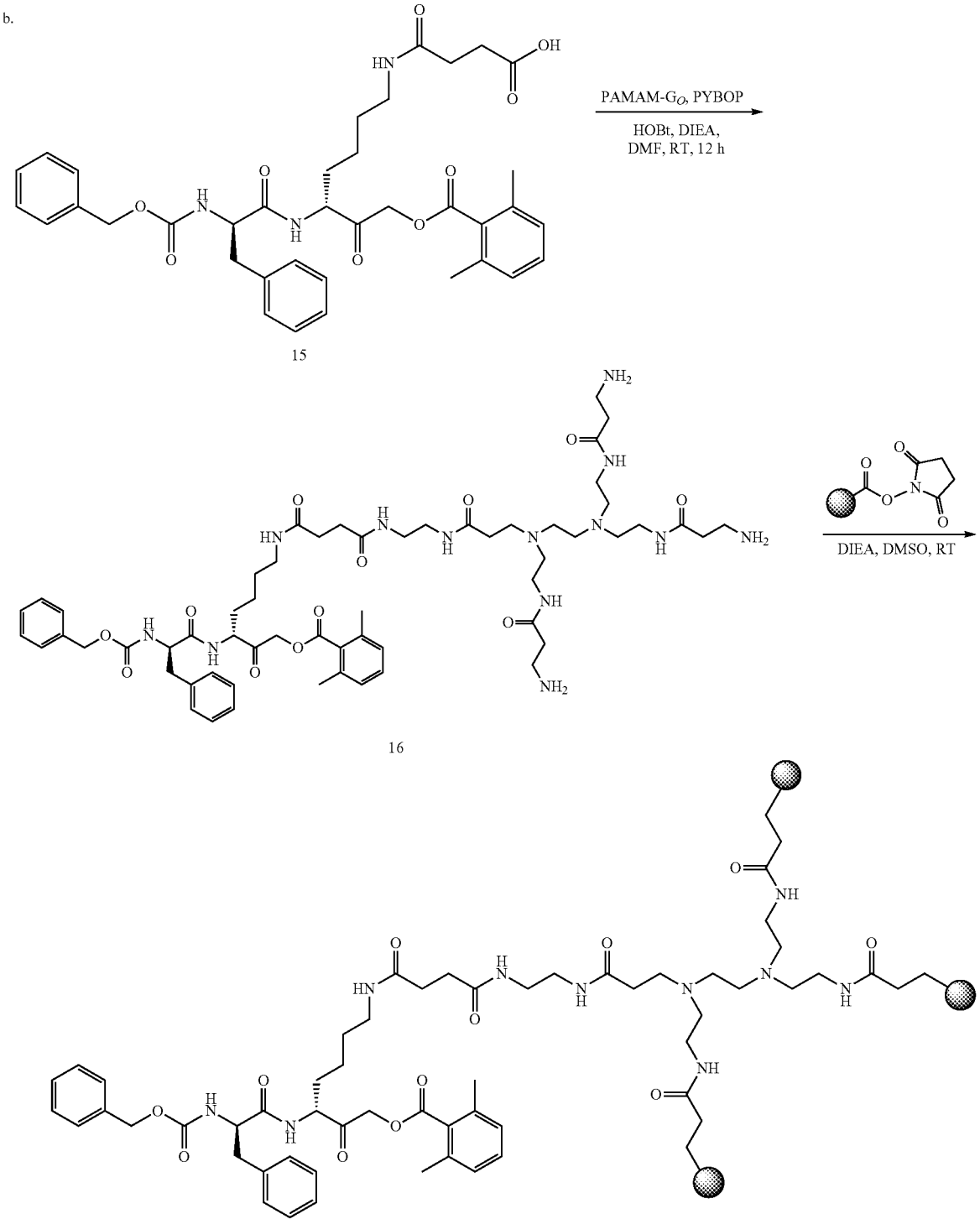

Where, 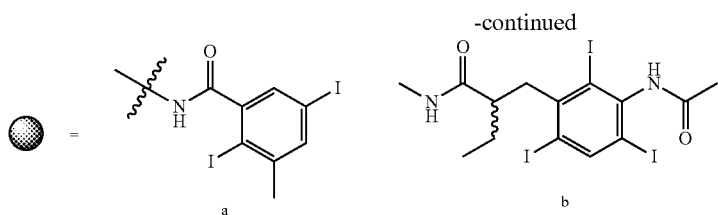
Synthesis of iodine tagged activity based probe (CT-ABP). Synthesis of Iodine CT-ABP (two tagged).
c.
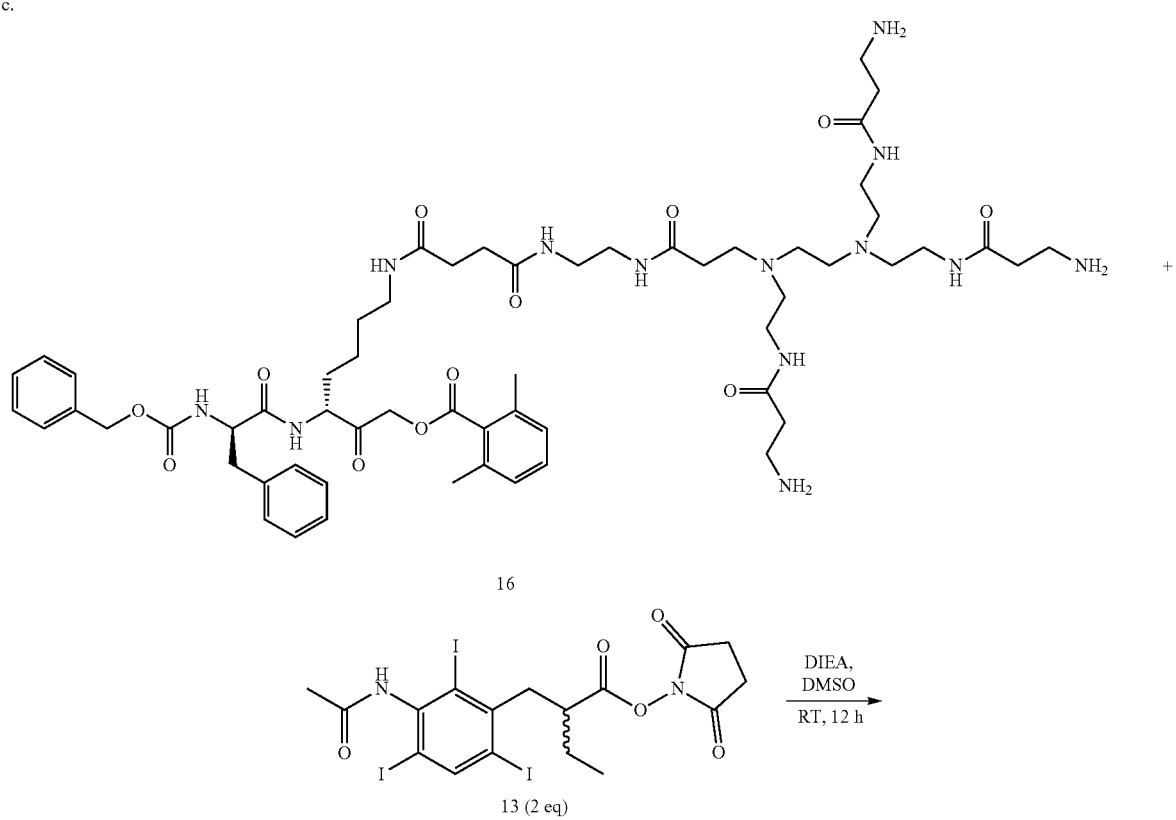
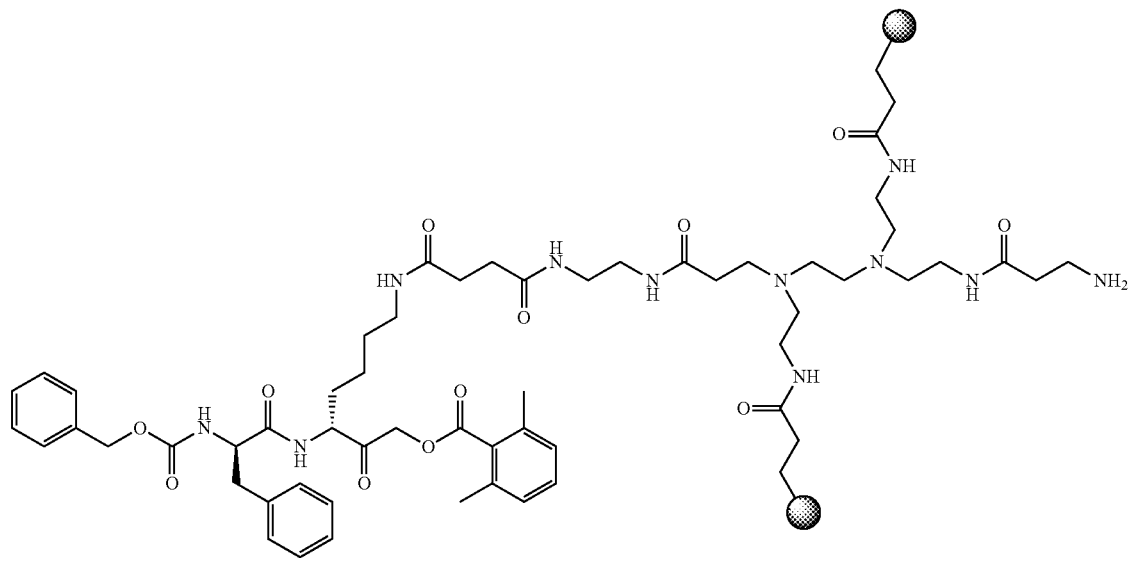
18 (HG77)

Where, 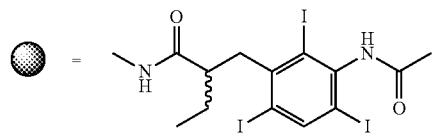
-continued
Scheme 4
Synthesis of mutiple iodine tagged activity based probe (CT-ABP). Synthesis of GB111NH-SE
a.
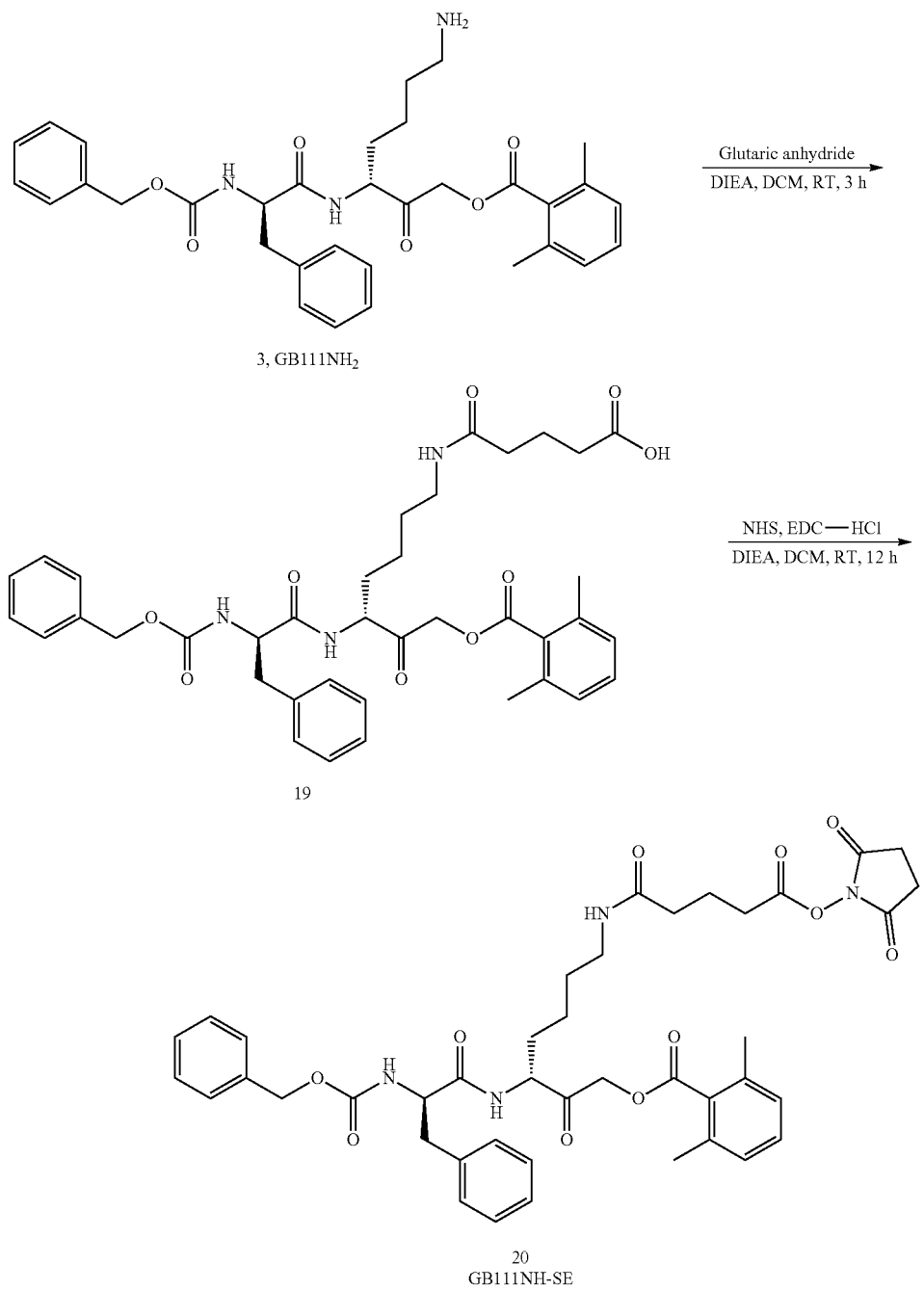

-continued
Synthesis of mutiple iodine tagged activity based probe (CT-ABP). PAMA-G1 conjugated with Iodine tag.
b.
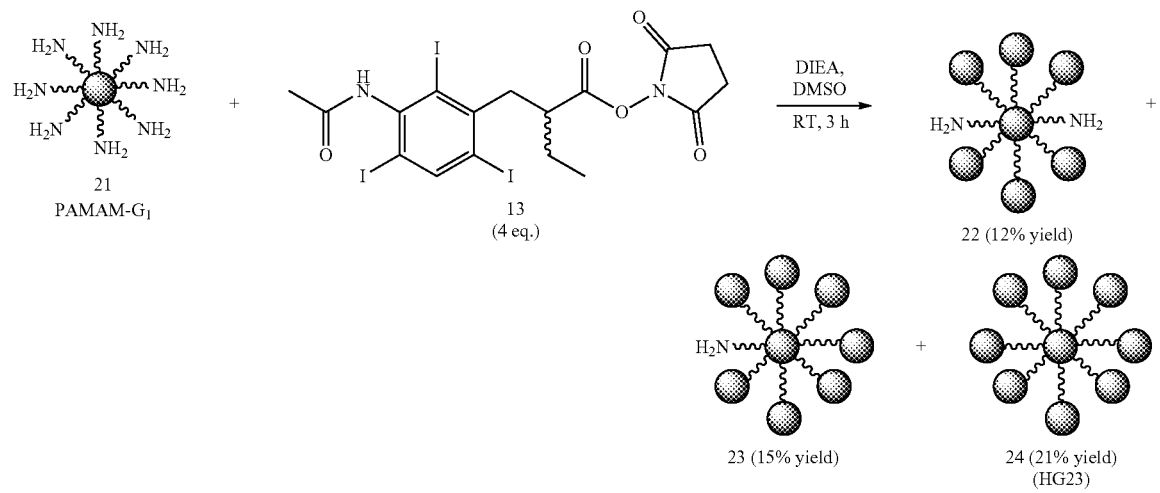
Synthesis of mutiple iodine tagged activity based probe (CT-ABP). c) Synthesis of Iodine CT-ABP (Six tagged). d) Synthesis of Iodine CT-ABP (Seven tagged).
c.
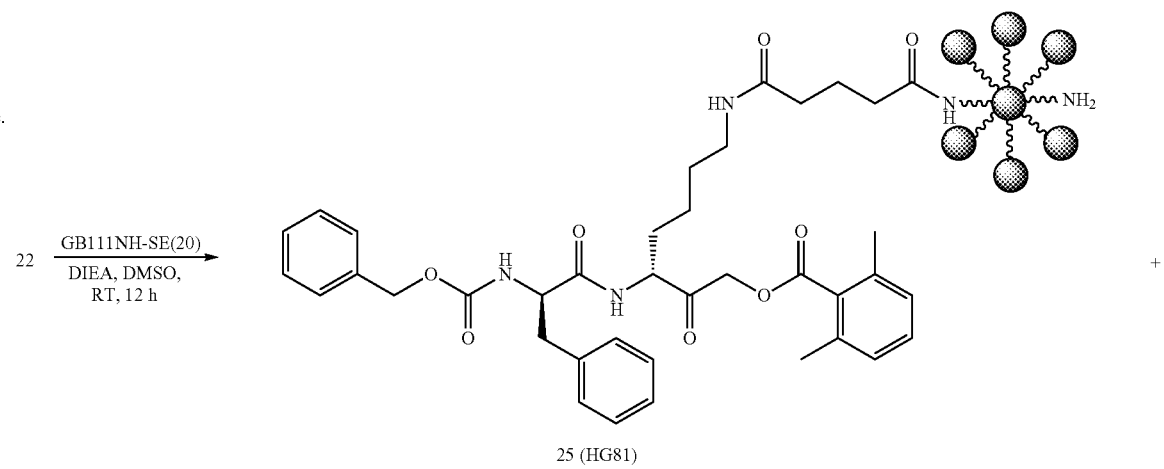
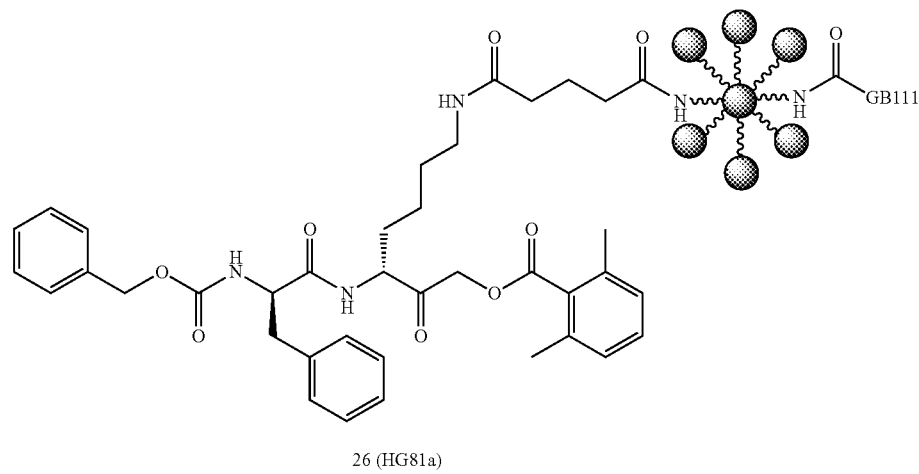

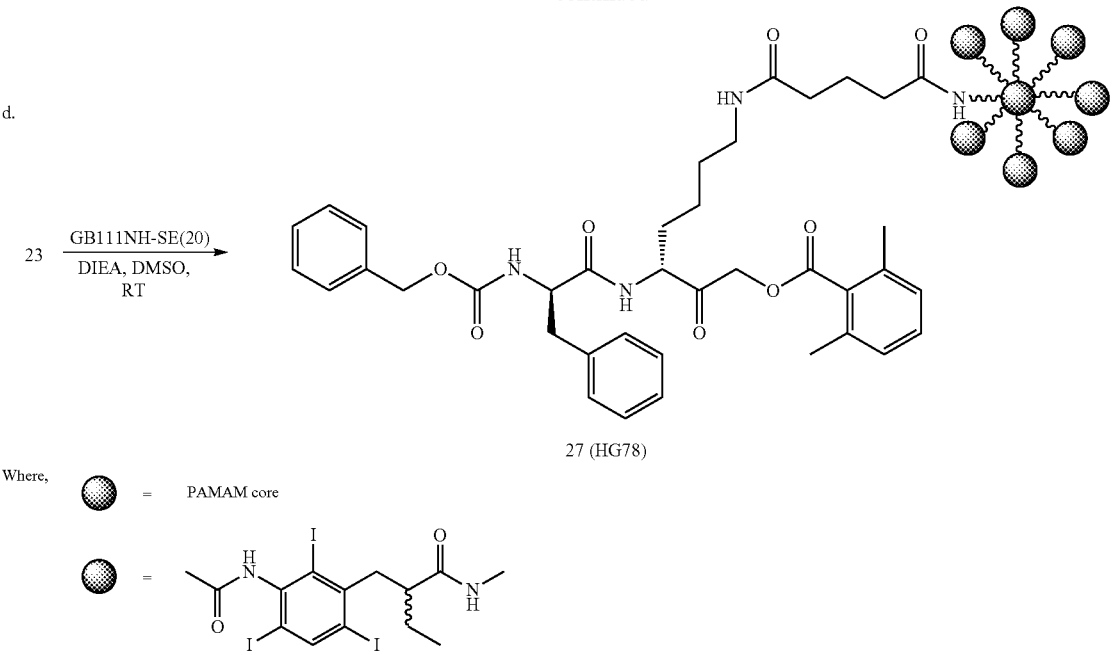

27 (HG78)

Where,
● = PAMAM core

● = [acetylated triiodo benzyl structure]

TABLE 3

List of the probes synthesized

| Probe Code | PAMAM gen. | No. of Iodine tag | No. of Iodine | No. of GB111NH— | No. of free NH₂ | Molecular weight |
|---|---|---|---|---|---|---|
| 14a (HG39) | — | 1 | 3.00 | 1.0 | — | 1055.00 |
| 14b (HG41) | — | 1 | 3.00 | 1.0 | — | 1168.08 |
| 17a (HG49) | G0 | 3 | 9.00 | 1.0 | — | 2616.82 |
| 17b (HG51) | G0 | 3 | 9.00 | 1.0 | — | 2956.08 |
| 18 (HG77) | G0 | 2 | 6.00 | 1.0 | 1.0 | 2361.28 |
| 24 (Control) | G1 | 8 | 24.00 | — | — | 6187.42 |
| 25 (HG81) | G1 | 6 | 18.00 | 1.0 | 1.0 | 5653.11 |
| 26 (HG81a) | G1 | 6 | 18.00 | 2.0 | — | 6308.40 |
| 27 (HG78) | G1 | 7 | 21.00 | 1.0 | — | 6247.91 |

Biochemical Evaluations

Figure 11C:
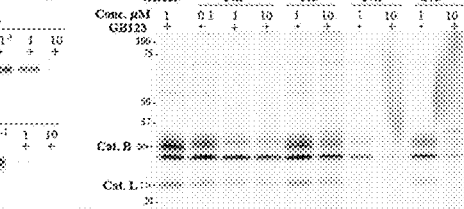
Figure 11F:
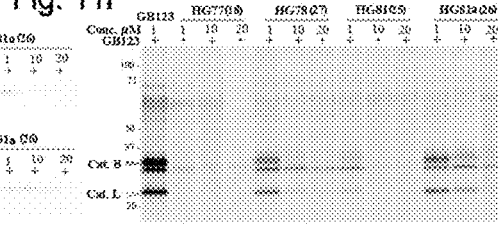

The biochemical evaluation of the new probes started with evaluation for their ability to bind recombinant human cathepsins B or Cathepsin L. Recombinant human cathepsins B was incubated with increasing concentrations of the probes for 2 hour. Residual activity was detected by a fluorescently labeled cathepsin ABP GB 123 that was added to samples for 30 minutes at r.t. The free probe was separated from the enzyme-probe complex by SDS PAGE, the detection of the probe-enzyme complex was done by a fluorescent scanning of the gel at Cy5 fluorescence, I-CT-ABP 14a, 17a, 14b, 17b, 18, HG78, HG81 and HG81a, were found to bind the cathepsins in a dose respond manner (FIGS. 11A, 11B, 11D and 11E). Evaluation of the probes cell permeability and capability of labeling cellular cathepsin enzymes was performed using competitive inhibition assay as well. The competitive inhibition assay was carried out by incubation of NIH-3T3 cells with all iodine tagged probes for 24 hours. Next, residual cathepsins activity was labeled by GB123 1 μM during 2 hours. Cell lysates were separated on SDS-PAGE followed by scanning the gel for fluorescence to visualize labeling of residual cathepsins activity by GB123 (FIGS. 11C and 11F). Encouragingly, all iodine derivatives showed high cell permeability. For three, six and seven iodine tagged probe showed higher inhibition.

The synthesis of the Cy5 labelled I-CT-ABP were performed using six tagged compounds (25), which on reaction with Cy5 NHS ester in basic conditions to give 28 (HG92). As negative controls, seven tagged compound were on reaction with Cy5 NHS ester to give 29 (HG31) (Scheme 5). The design of the iodine conjugated, generation 3 (G3), ethylenediamine core PAMAM dendrimers used in this study, for the purpose of the designed conjugate was for targeted molecular imaging of cancer and atherosclerosis disease, the conjugate contrast agent is the Iodine, the tumor targeting molecule GB111. In this study, the inventors also evaluated the conjugate contrast agent is the Iopanic acid, the tumor targeting molecule GB111 and the fluorescent molecule Cy5 to achieve the most sensitive detection of targeted cathepsin labelling.

The synthesis, purification, and analysis of the conjugates were performed following standard methods. The NHS ester of acetylated Iopanic acid Iopanoic acid was first conjugated to the ethylenediamine core PAMAM-G3 dendrimer at a mean stoichiometric ratio of 16.0 per dendrimer as determined by 1H NMR. Next, the GB111 was conjugated to the PAMAM-G3, dendrimer at a mean stoichiometric ratio of 1-2 targeting molecule per dendrimer, as determined by 1H NMR. Finally, the remaining surface groups on the dendrimer, initially primary amines, were neutralized by the addition of acetylation, or PEG NHS ester, as previous studies have found that highly cationic PAMAM dendrimers disrupt cellular membranes. As negative controls, conjugates PAMAM-G3 dendrimers without GB111 were synthesized in parallel with HG, with the exemption of the GB111 conjugation steps. Therefore, the only chemical difference between these dendrimers and HG33, HG94, HG97 is the presence of GB111 (Scheme 6). The synthesis, purification, and analysis of the Cy5 labelled conjugates were performed following standard methods. The NHS ester of acetylated Iopanic acid was first conjugated to the PAMAMG3 dendrimer core at a mean stoichiometric ratio of 16.0 per dendrimer as determined by $^1$H NMR. Next, the GB 111 was conjugated to the PAMAM-G3, dendrimer at a mean stoichiometric ratio of 1-2 targeting molecule per dendrimer and then Cy5 was conjugated to the conjugated dendrimer at a mean stoichiometric ratio of 1-2 fluorophores per dendrimer, as determined by $^1$H NMR. Finally, the remaining surface groups on the dendrimer, primary amines were neutralized by the addition of acetylation, or PEG NHS ester. As negative controls, conjugates of PAMAM-G3 dendrimers without GB111 were synthesized in parallel with HG99 and HG32, with the exemption of the GB111 conjugation steps. Therefore, the only chemical difference between these dendrimers and HG is the presence of GB 11 (Scheme 7).

Scheme 5
Synthesis of Cy5 labelled Iodine CT-ABP. a) Synthesis of Cy5 labelled
Iodine CT-ABP (Six tagged). b) Synthesis of Cy5 labelled control Iodine CT-ABP (Seven tagged).

a.

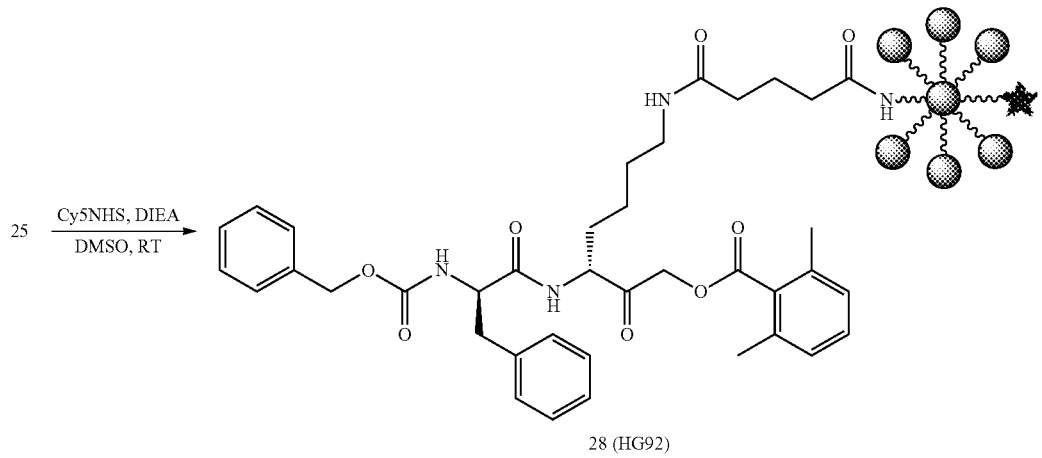

b.

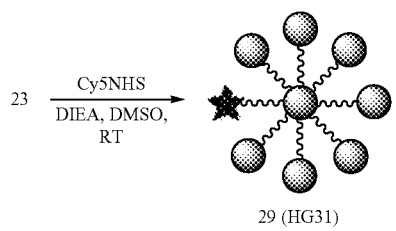

Where,  = PAMAM core

 = Cy5 fluorophore

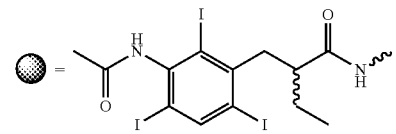

Scheme 6

Figure 28:
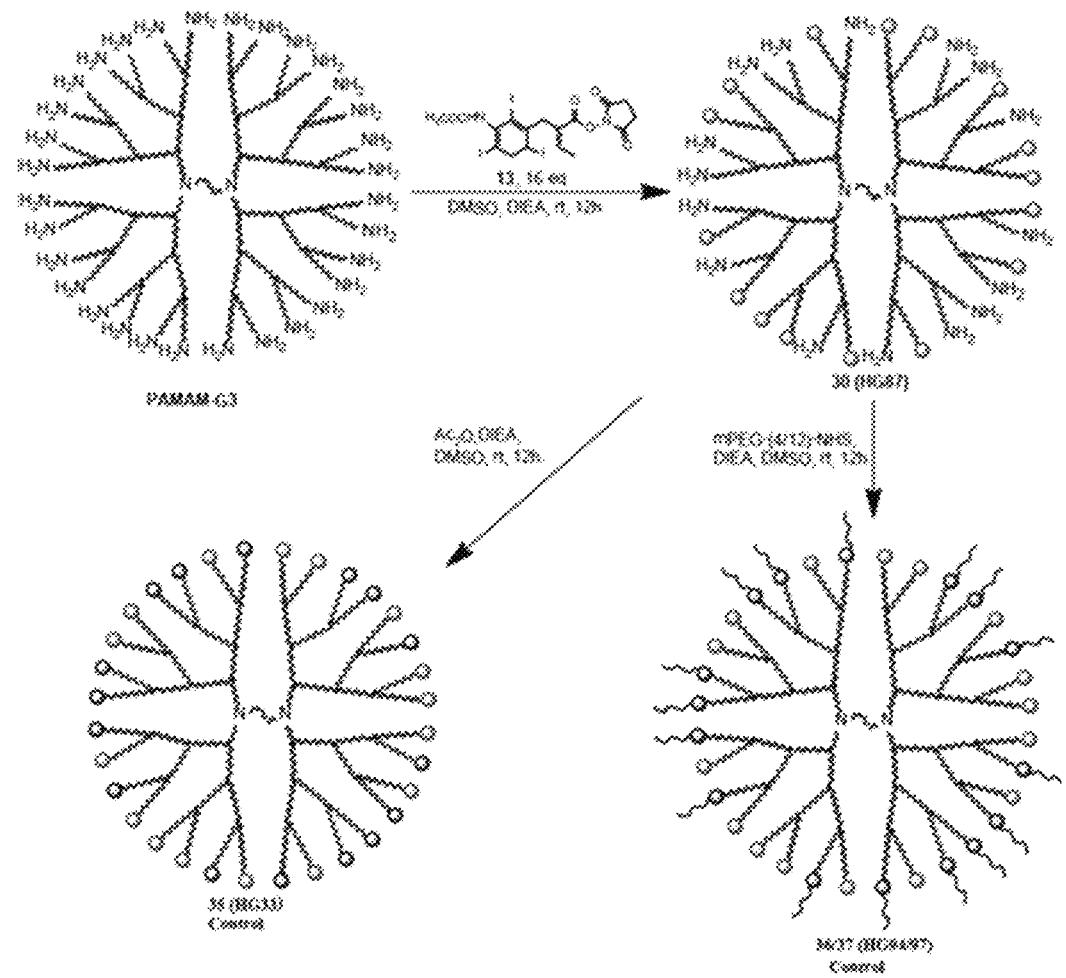
FIG. 28 is an synthesis of multiple iodine tagged CT-ABP (Acetylated and PEGylated).

Synthesis of multiple iodine tagged CT-ABP (Acetylated and PEGylated). as seen in FIG. 28

Scheme 6 (cont.)

Figure 29:
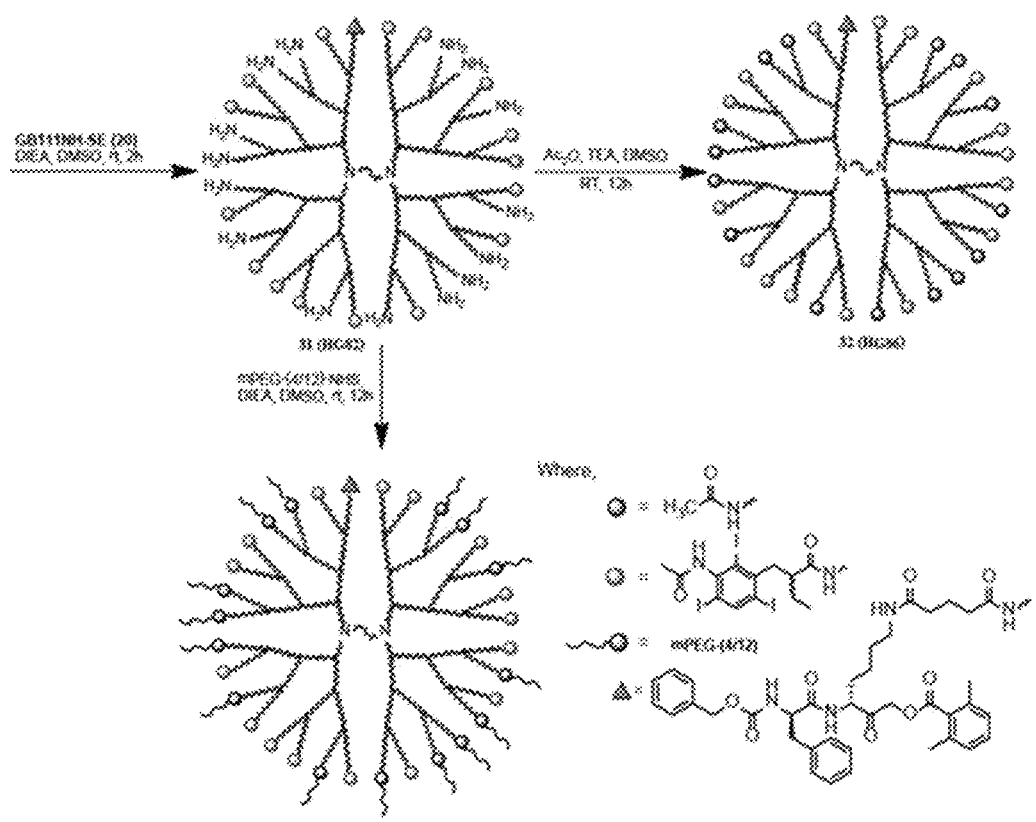
FIG. 29 is a synthesis of multiple iodine tagged CT-ABP (Acetylated and PEGylated).

Synthesis of multiple iodine tagged CT-ABP (Acetylated and PEGylated). as seen in FIG. 29

Scheme 7

Figure 30:
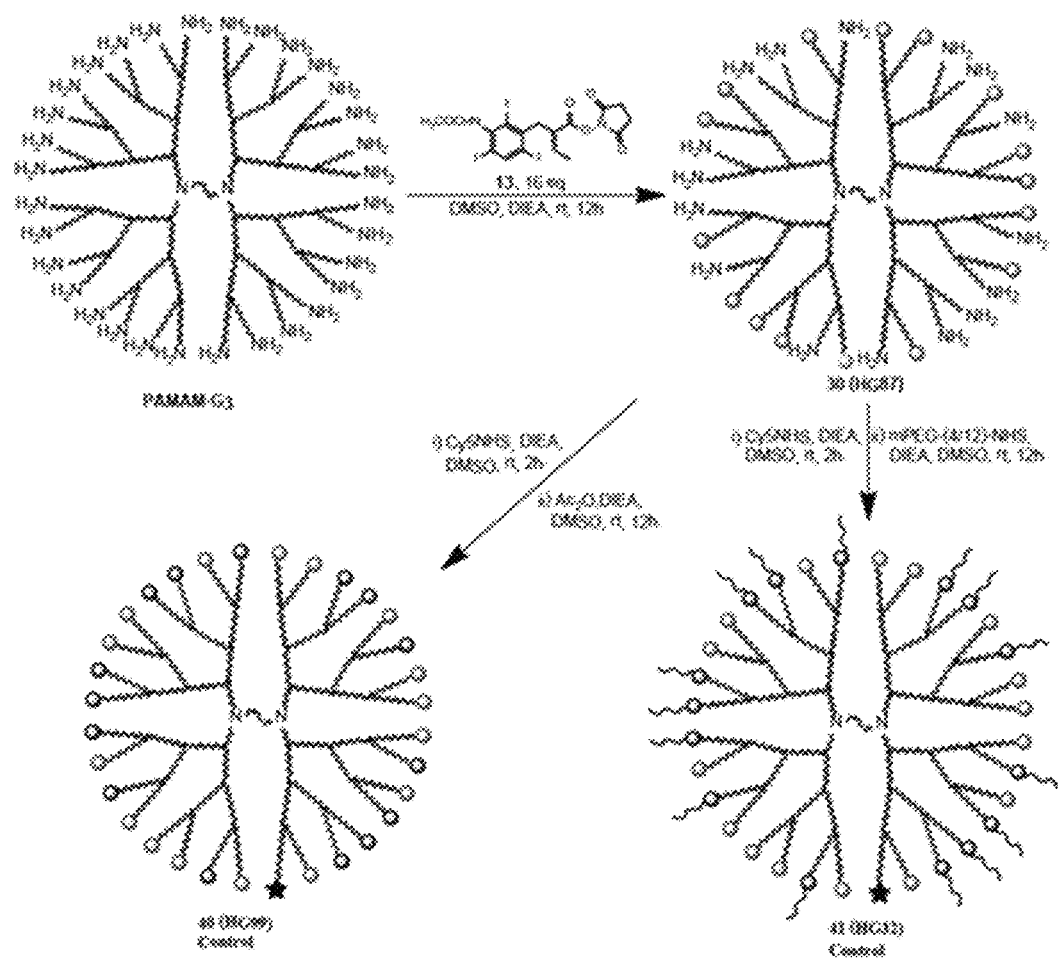
FIG. 30 is a synthesis of multiple iodine tagged CT-ABP (Acetylated, PEGylated and Cy5 labelled).

Synthesis of multiple iodine tagged CT-ABP (Acetylated, PEGylated and Cy5 labelled), as seen in FIG. 30

Scheme 7 (Cont.)

Figure 31:
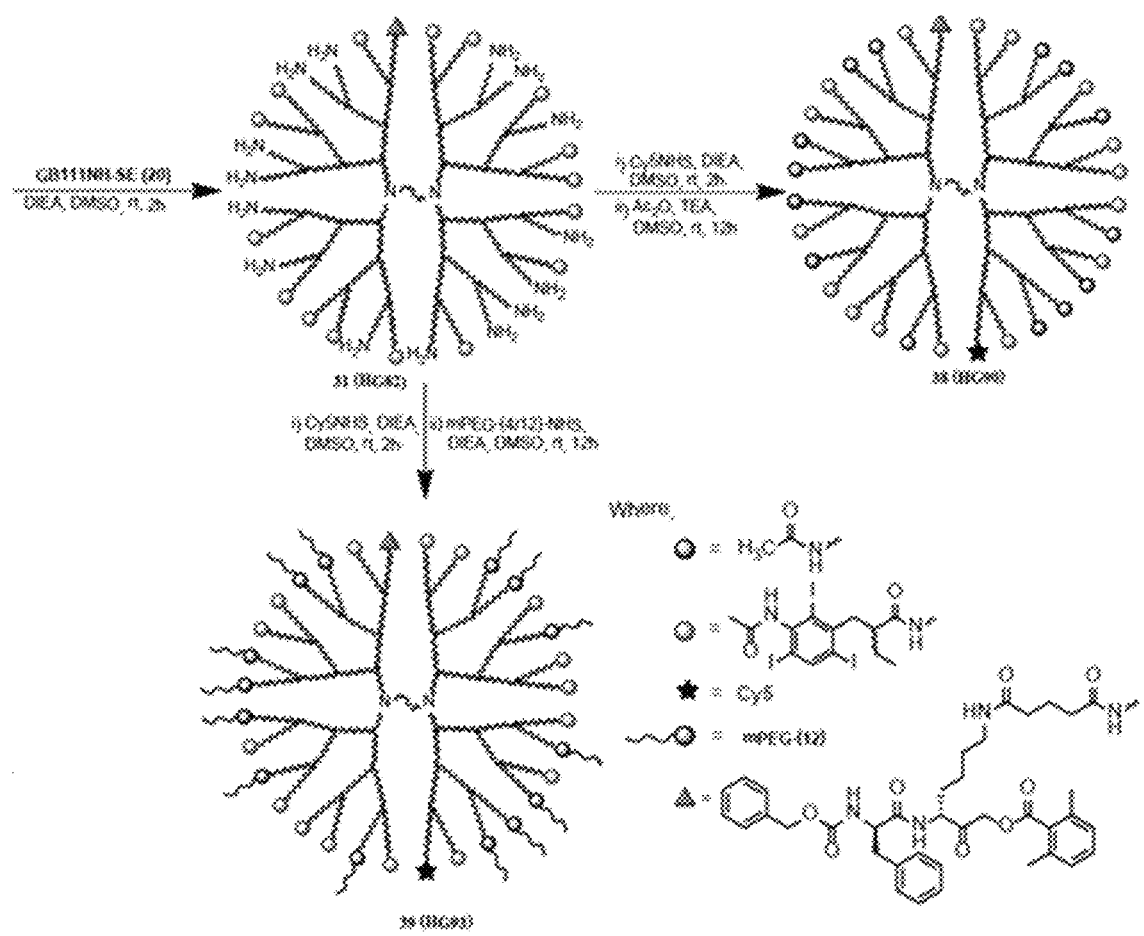
FIG. 31 is a synthesis of multiple iodine tagged CT-ABP (Acetylated, PEGylated and Cy5 labelled).

Synthesis of multiple iodine tagged CT-ABP (Acetylated, PEGylated and Cy5 labelled), as seen in FIG. 31

TABLE 4

List of activity based probes (CT-ABP) synthesized.

| Probes | PAMAM gen. | No. of Iodine tag | No. of Iodine | No. of GB111NH- |
|---|---|---|---|---|
| HG82 | G3 | 16 | 48.00 | ~1.0 |
| HG86 | G3 | 16 | 48.00 | ~1.0 |
| HG95 | G3 | 16 | 48.00 | ~1.0 |
| HG96 | G3 | 16 | 48.00 | ~1.0 |
| HG87 | G3 | 16 | 48.00 | — |
| HG33 | G3 | 16 | 48.00 | — |
| HG94 | G3 | 16 | 48.00 | — |
| HG97 | G3 | 16 | 48.00 | — |
| HG92 | G1 | 6 | 18.00 | 1.0 |
| HG90 | G3 | 16 | 48.00 | ~1.0 |
| HG93 | G3 | 16 | 48.00 | ~1.0 |
| HG31 | G1 | 7 | 21.00 | — |
| HG32 | G3 | 16 | 48.00 | — |
| HG99 | G3 | 16 | 48.00 | — |

| Probes | No. of Acetyl | No. of PEG-4 (333) | No. of PEG-12 (750) | No. of Cy5 | Molecular weight |
|---|---|---|---|---|---|
| HG82 | — | — | — | — | ~17098 |
| HG86 | ~15.00 | — | — | — | ~17743 |
| HG95 | — | ~15.00 | — | — | ~20368 |
| HG96 | — | — | ~15.00 | — | ~26623 |
| HG87 | — | — | — | — | ~16429 |
| HG33 | ~16.00 | — | — | — | ~17117 |
| HG94 | — | ~16.00 | — | — | ~19917 |
| HG97 | — | — | ~16.00 | — | ~26621 |
| HG92 | — | — | — | 1.0 | 6307 |
| HG90 | ~14.00 | — | — | ~1.0 | ~18253 |
| HG93 | — | — | ~14.00 | ~1.0 | ~26623 |
| HG31 | — | — | — | 1.0 | 6241 |
| HG32 | — | — | ~15.00 | ~1.0 | ~25989 |
| HG99 | ~15.00 | — | — | ~1.0 | ~25989 |

Biochemical Evaluations

Figure 12A:
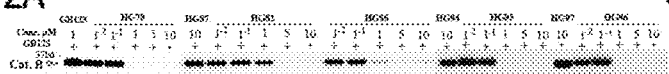
FIGS. 12A-12F show biochemical evaluation of Iodine-based compounds (IN-ABP)
Figure 12C:
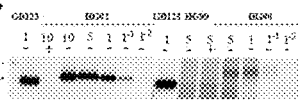
Figure 12B:
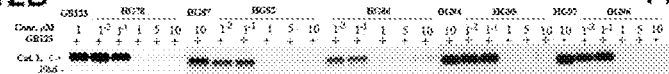
Figure 12D:
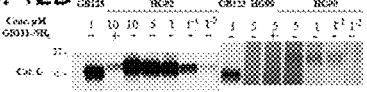
Figure 12E:
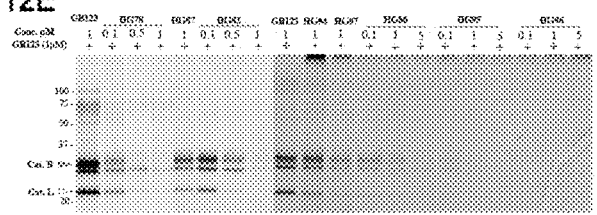
Figure 12F:
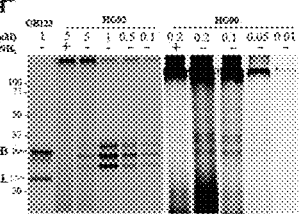

Recombinant human cathepsins B was incubated with increasing concentrations of the probes for 2 hour. Residual activity was detected by a fluorescently labeled cathepsin ABP that was added to samples for 30 minutes at r.t. The free probe was separated from the enzyme-probe complex by SDS PAGE, the detection of the probe-enzyme complex was done by a fluorescent scanning of the gel at Cy5 fluorescence, FIG. 12. HG82, HG86, HG95 and HG96 were found to bind the cathepsins in a dose respond manner. To assure that the binding is dependent on protease activity, a control were performed HG87, HG94 and HG97 lacking the reactive moiety. Since no inhibition was detected, it was conclude that the binding of the probes occur in an activity-dependent manner (FIGS. 12A and 12B). Evaluation of I-CT-ABPs in intact cells. The competitive inhibition assay was carried out by incubation of NIH-3T3 cells with all iodine tagged probes for 24 hours. Next, residual cathepsins activity was labeled by GB123 1 µM during 2 hours. Cell lysates were separated on SDS-PAGE followed by scanning the gel for fluorescence at: 645/670 nm to visualize labeling of residual cathepsins activity by GB123 (FIG. 12E). Encouragingly, all iodine derivatives showed high cell permeability. For acetylated and PEGylated probe showed higher inhibition. For control probe, no inhibition was detected, the binding of the probes occur in an activity-dependent manner. Recombinant human cathepsins B was incubated with increasing concentrations of the Cy5 labelled probes for 2 hour. The free probe was separated from the enzyme-probe complex by SDS PAGE, the detection of the probe-enzyme complex was done by a fluorescent scanning of the gel at Cy5 fluorescence. HG92, and HG90, were found to bind the cathepsins in a dose respond manner (FIGS. 12C and 12D). The binding of the all the Cy5 labelled probes occur in an activity-dependent manner. Direct labeling in intact cells. The assay was carried out by incubation of NIH-3T3 cells with Cy5 labelled iodine tagged probes for 24 hours. Cell lysates were separated on SDS-PAGE followed by scanning the gel for fluorescence at: 645/670 nm to visualize labeling of residual cathepsins activity by GB123. Encouragingly, all Cy5 labelled iodine derivatives showed high cell permeability and binding to cellular cathepsins (FIG. 12F). For the PEGylated I-CT-ABP HG93 and HG32 also observed that recombinant cathepsin activity and cell permeability, it's difficult to quantify the selective inhibition due to enhanced permeation and retention (EPR) effect.

Cytotoxicity

Figure 13A:
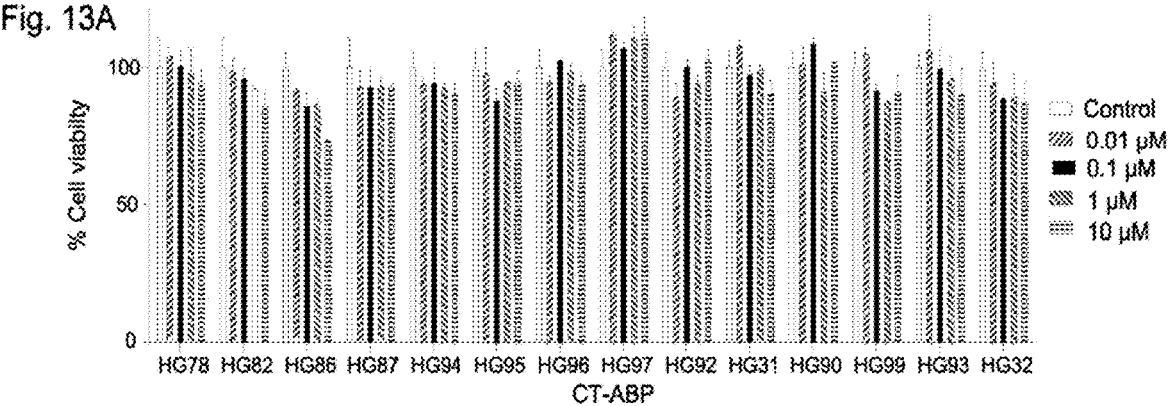
FIGS. 13A and 13B are bar representations showing viability assay of Iodine tagged probes at 24 h (FIG. 13A) and 48 h (FIG. 13B), no toxicity was found in any of the probes check in the first 24 hours while a slight toxicity was observed at 10 μM of HG 82, 86, and 87 after 48 hours.
Figure 13B:
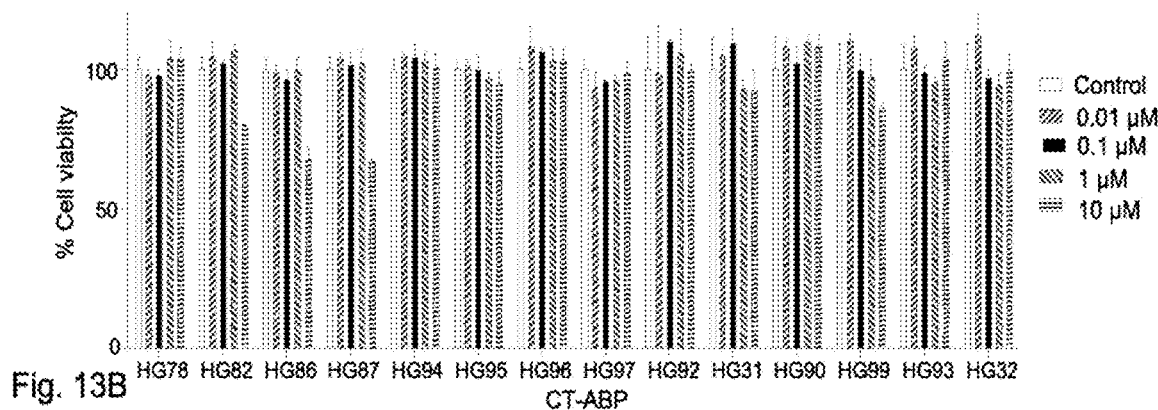

Cytotoxicity study of the I-CT-ABPs, the toxic response to the systematically varied physico-chemical properties of successive PAMAM dendrimers. In vitro cytotoxicity of I-CT-ABPs to NIH-3T3 cell lines was investigated. Viability assay was performed for assessment of the cytotoxicity of each I-CT-ABP to the NIH-3T3 cell lines using the methylene blue method. All the I-CT-ABPs shows low toxicity with NIH-3T3 cells in a concentration range from 0.01 to 10 µM after 24 h and 48 h incubation. All the I-CT-ABP does not block the cellular uptake and only shows specific uptake of covalently conjugation to Cathepsin B and L (FIGS. 13A and 173). No toxicity was found in any of the probes check in the first 24 hours (FIG. 13A) while a slight toxicity was observed at 10 µM of HG 82, 86, and 87 after 48 hours (FIG. 13B).

Pharmacokinetic Properties of Cy5 Labelled Iodine Probes In Vivo by Non-Invasive Fluorescence Imaging The in vivo studies were initiated by investigating the pharmacokinetics of Cy5 labelled I-CT-ABP, HG92, HG90, and respective control in tumor-bearing mice. This was done to establish the non-invasive imaging capabilities of these contrast media. 4T1 cells were grown to sub-confluency, followed by detachment with trypsin, and resuspension in 0.5% BSA in sterile PBS and 25% matrigel. Cells ($9 \times 10^5$ per spot in a total volume of 20 µl) were injected subcutaneously on the back of 3-4 week-old male BALB/c mice under isoflurane anesthesia. Tumors were established 9-11 days after cells injections. Each mouse received 100 µl probe solution containing 75 nmol compound by tail vain injection. The pharmacokinetics of HG92, and HG90 in tumor-bearing mice relative to control probes lacking the GB111 moiety (HG31, HG99 and HG32 respectively) was evaluated. After I-CT-ABP injection, the fluorescent I-CT-ABP rapidly circulated throughout the animal and high fluorescent signals could be seen in virtually all tissues, including the tumors. A clear signal from the tumor could be detected after 0.5 hours together by the fluorescence of the I-CT-ABP distributed throughout the body. This non-specific fluorescence diminished over time with clearance of the un-bound PAMAM nanomaterics from the body of the mouse, resulting in a tumor-specific signal increases. This specific signal increased over time and reached a maximum at 6-8 hours post I-CT-ABP injection. The HG92 targeted I-CT-ABP first shows an accumulation over 6-8 hours, then a slow decrease, whereas non-targeted contrast agent HG31 shows monoexponetial decay (FIGS. 14A and 14B). For the HG90 targeted I-CT-ABP shows an accumulation over 5-7 hours, then a slow decrease, whereas non-targeted contrast agent HG99 shows monoexponetial decay (FIGS. 14C and 14D). Due to the covalent nature of the targeted I-CT-ABP a significant amount retained in the tumor up to 24 hours post injection. The targeted Cy5 labelled I-CT-ABP circulation in mice was monitored in organ harvested after 24 hour injection, quantified by fluorescence of Cy5 labelled I-CT-ABP. In the targeted I-CT-ABP mice organs, liver, kidney, spleen and tumor shows strong fluorescence intensity, than the non-targeted contrast agent. The fluorescence images indicated strong accumulation of targeted I-CT-ABP in the tumor tissues than non-targeted contrast agent. It then evaluated the probe of HG92 and HG90 demonstrating excellent correlation with the in vivo data. Based on these results, the optimal time for the treatment was determined to be 5-7 hour after administration of the targeted I-CT-ABP (FIG. 14).

Figure 17:
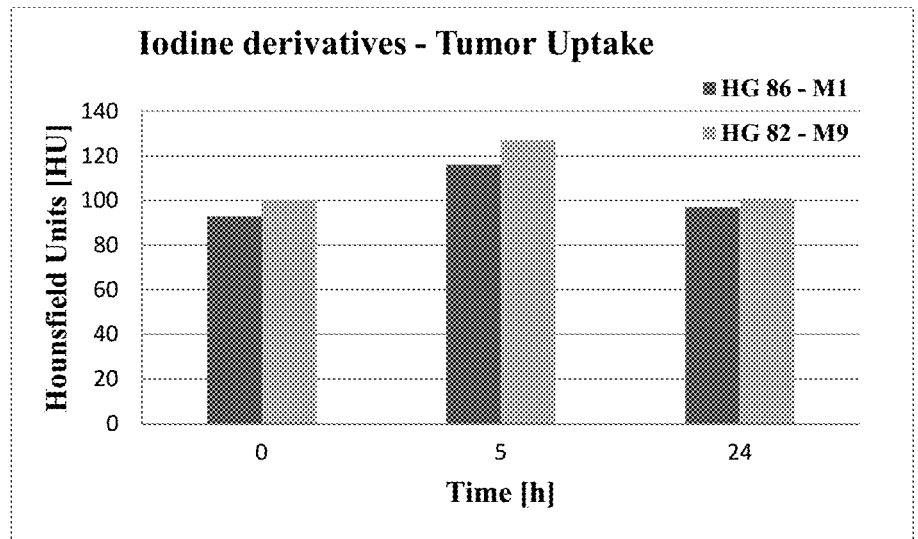
FIG. 17 is a bar graph showing in vivo X-ray computed tomography pharmacokinetic comparative study of IN-ABP HG82 and HG86.
Figure 18A:
FIGS. 18A-18D are in vivo X-ray computed tomography, a representative picture of a mouse 5 h post-injection of HG82 that specifically targets cathepsin activity within the tumor, FIG. 18A coronal plane, FIG. 18B transverse plane and FIG. 18C sagittal Plane, FIG. 18D tomographic view, tumor detected was colored gray.
Figure 18D:
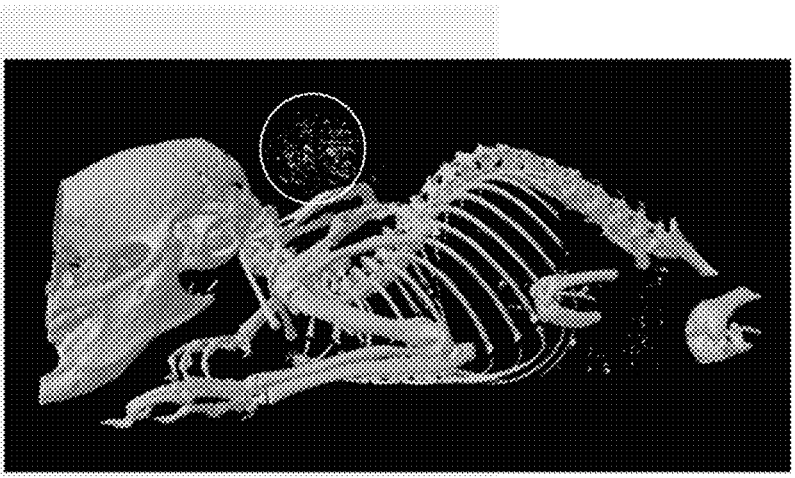
Figure 18B:
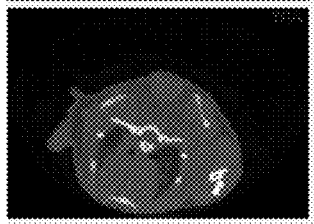
Figure 18C:
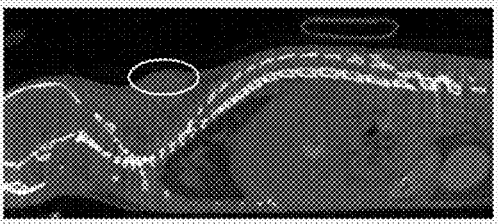

CT In Vivo Imaging of Iodine Tagged I-CT-ABP:

The X-ray CT pharmacokinetic behavior of I-CT-ABPs (HG92, HG90 and respective controls) in tumor bearing mice. The single contrast agents' experiment required two CT scan separated by several hours for complete blood clearance of contrast agents in order to quantify and differentiate vascular signal from probe labelled tumor signal. This was done to establish the non-invasive imaging capabilities of targeted I-CT-ABPs. The choosing the ideal targeted contrast agent, the inventors aim to maximize both tumor specificity and total tumor uptake and retention of the I-CT-ABPs. CT images were acquired with subsequent scan obtained at 0 h 5 h and 24 h after injection. The mice were pre scanned before injection by a CT scanner equipped with 64 detectors, 55 kVp & 500 mAs was used for all scans. A CT signal from the tumor could be detected after 5 hours for targeted I-CT-ABP was distributed evenly throughout the body. Images obtained after 24 h injection revealed significant removal of I-CT-ABP from the blood pool and accumulation in the liver, spleen, kidney and tumor observed. The tumor is readily visible in the data for the targeted I-CT-ABP relative to non-targeted. Quantitative analysis of the CT contrast in Hounsfield unit (HU) with tumor size indicated that the tumor labelling of targeted I-CT-ABP (HG9) is more significant than non-targeted nanomaterial (HG99), after 24 h (FIG. 157). While the targeted I-CT-ABP (HG92) shows an insignificant difference to non-targeted nanomaterials (HG31) due to the low number of iodine and low sensitivity X-ray CT (FIG. 15A). After 5 h and 24 h, targeted I-CT-ABP HG92 and HG90 remained visible within the tumor tissues in the CT images, indicating prolonged retention of the I-CT-ABP within tissues (FIGS. 15A and 15B). Here, accumulation of I-CT-ABP in the tumor tissues induces X-ray absorption and increase in density. The kinetics of accumulation of targeted I-CT-ABP HG90 is also different that of the non-targeted one, this specific signal at the time 5 hours and it increased at 24 hours post I-CT-ABP injection. It was noted that this signal in the mouse's body is likely due to a combination of labeling of active cathepsins in organs that have high cathepsin activity and retention of the I-CT-ABP in tissues (FIGS. 16A and 16B). The data shown here are consistent and with increasing efficacy of I-CT-ABP s of tumor that express elevated levels of cathepsin activity, and its extent this theme for a new class of targeted X-ray contrast agent. Similarly to describe above the I-CT-ABP HG82 and HG86 were evaluated as in vivo CT contrast agents. Mice received 100 µl of a 10 mg/ml solution of targeted I-CT-ABPs by tail vain injection. The mice were scanned before, at 5 and 24 hours post injection by a Micro-CT scanner equipped with 64 detectors, 80 kVp & 500 mAs was used for all scans. A CT signal from the tumor could be detected 5 hours post injection of the I-CT-ABP HG82, as seen in FIG. 17. This specific signal was higher at the time 5 h and was reduced at 24 hours post probe injection as seen in FIG. 18D. A clear CT signal was detected within the tumor tissue.

Figure 19:
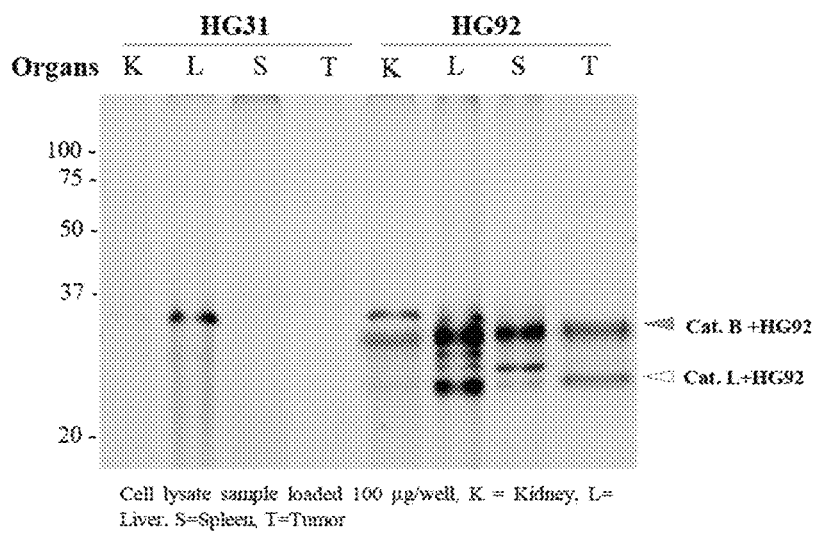
FIG. 19 presents SDS of tumors and organs being lysed and equal protein samples were spread by SDS-PAGE, followed by fluorescent scanning of the gel. Specific labeling of cathepsins by HG92 is detected in kidney, liver, spleen and tumor tissues.
Figure 20:
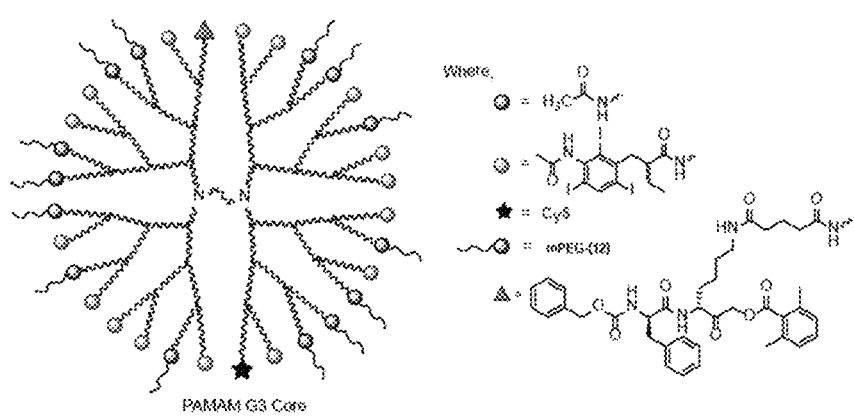
FIG. 20 is an exemplary compound of the invention in some embodiments.
Figure 21:
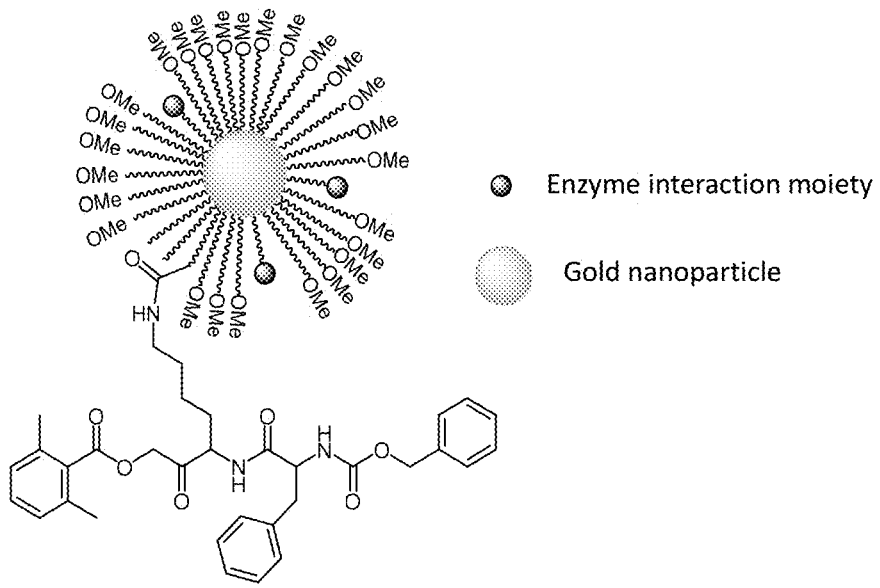
FIG. 21 is a carrier moiety.
Figure 22:
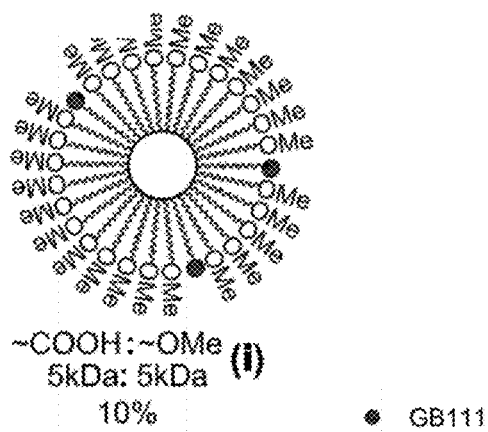
FIGS. 22-26 are examples of a 5 kDa PEG-OMe moiety.
Figure 23:
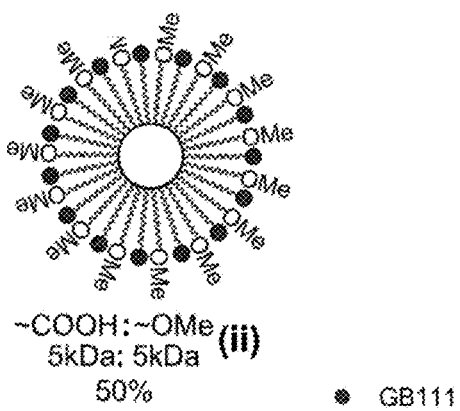
Figure 24:
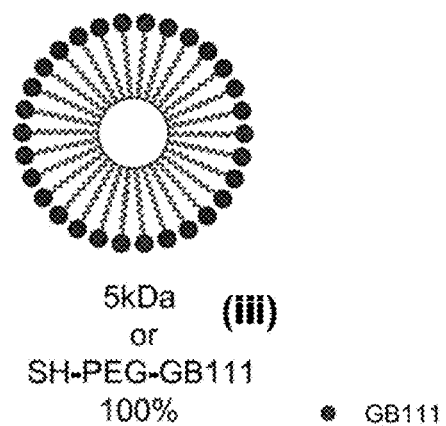
Figure 25:
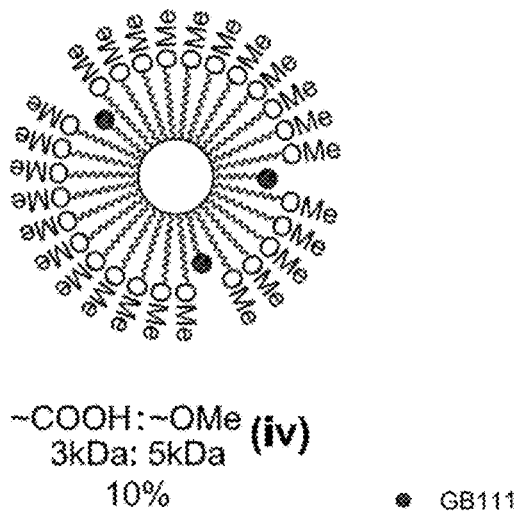
Figure 26:
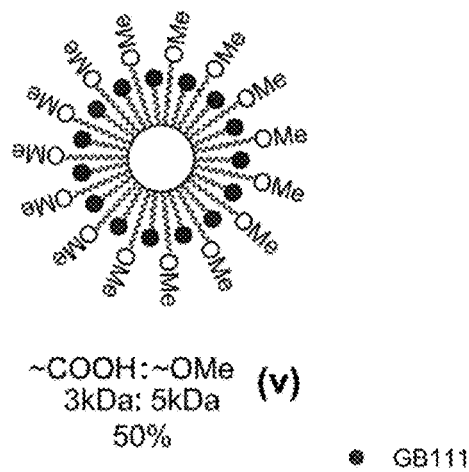
Figure 27:
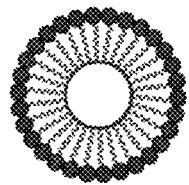
FIG. 27 is an example of a 3 kDa PEG moiety.

Biodistribution and Cathepsin Labeling of I-CT-ABP and Control:

The tumor tissues was analyzed, as well as tissue from liver, kidney, and spleen. The Cy5 labelled targeted I-CT-ABP (HG92) and non-targeted contrast agent (HG31) treated mouse organ, tissue lysates were prepared and separated by SDS-PAGE, Labeling profiles in all tissues from both Cy5 labelled targeted I-CT-ABP and non-targeted contrast agent treated mice showed the different pattern of activity, cathepsins specific labeling was detected with the higher shift of fluorescent bands between 20-35 kDa, characteristic band for labelled I-CT-ABP-cathepsin enzyme complex. For non-targeted contrast agent, no labeling of cathepsin was detected, the binding of the probes occur in an activity-dependent manner (FIG. 19). The inventors did see I-CT-ABPs cathepsin activity in the tumor, and also saw significant cathepsin activity in other tissue, including spleen, liver, and kidney activity is also presented confirmed by pharmacodynamics therapy. However, the Cy5 labelled targeted I-CT-ABP (HG90, HG93) and non-targeted contrast agent (HG99, HG32) were couldn't separate by SDS-PAGE, due to aggregation of tissue. The microscopy images of tumor tissues show significant difference in fluorescence intensity signal. This additional signal from Cy5 labelled targeted I-CT-ABP HG90 and HG92 is likely to be the pro form of a cysteine cathepsin that can be labeled by the active site I-CT-ABP if it accumulates at sufficient concentrations (data not shown).

The invention claimed is:

1. A compound comprising at least one carrier moiety bound to a plurality of CT imaging moieties, and with at least one enzyme interacting moiety,
    wherein the plurality of CT imaging moieties are selected from gold-based moieties, and
    wherein the at least one carrier is a nanoparticle, is attached to a
    (a) gold-based moiety comprising a plurality of gold nanoparticles (GNPs);
    and
    (b) the at least one enzyme interacting moiety is acyloxymethyl ketone (AOMK);
    wherein the GNPs and the at least one enzyme interacting moiety are linked to an oligomer or a polymer CM:

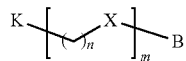
(CM)

wherein
K is a point of connectivity to GNP and is S—;
B is a point of covalent connectivity to the at least one enzyme interacting moiety and is —C(O)O
X is a heteroatom selected from —NH—, O and S;
n is 2; and
m is an integer from 60 to 120.

2. The compound according to claim 1, wherein the GNP has an average diameter of between 5 nm and 200 nm, or between 10 nm and 100 nm, or of 10 nm, 30 nm and 100 nm.

3. A diagnostic formulation comprising at least one compound according to claim 1.

4. The compound according to claim 1, wherein m is between 65 and 70.

5. The compound according to claim 1, wherein X is —O—.

6. The compound according to claim 1, wherein the GNPs have an average size of between 5 nm and 200 nm.

7. The compound according to claim 1, wherein the GNPs are surface-modified with ligands.

8. The compound according to claim 7, wherein the ligands are antibodies or peptides.

* * * * *